US012636097B2

(12) United States Patent
Cheung et al.

(10) Patent No.: US 12,636,097 B2
(45) Date of Patent: May 26, 2026

(54) REDUCTION OF FALSE POSITIVE HAPTIC INPUTS IN A ROBOTIC SURGICAL SYSTEM

(71) Applicant: Auris Health, Inc., Redwood City, CA (US)

(72) Inventors: Nicholas Cheung, Redwood City, CA (US); Colin Allen Wilson, Burlingame, CA (US); Ellen Klingbeil, Mountain View, CA (US); Karan Handa, San Francisco, CA (US); Chembian Parthiban, Fremont, CA (US)

(73) Assignee: Auris Health, Inc., Redwood City, CA (US)

( * ) Notice: Subject to any disclaimer, the term of this patent is extended or adjusted under 35 U.S.C. 154(b) by 620 days.

(21) Appl. No.: 17/970,506

(22) Filed: Oct. 20, 2022

(65) Prior Publication Data

US 2023/0125107 A1 Apr. 27, 2023

Related U.S. Application Data

(60) Provisional application No. 63/270,557, filed on Oct. 21, 2021.

(51) Int. Cl.
*A61B 34/30* (2016.01)
*A61B 34/00* (2016.01)
*A61B 90/00* (2016.01)

(52) U.S. Cl.
CPC .............. *A61B 34/30* (2016.02); *A61B 34/76* (2016.02); *A61B 90/361* (2016.02)

(58) Field of Classification Search
CPC ......... A61B 34/20; A61B 34/30; A61B 34/35; A61B 34/37; A61B 34/74; A61B 34/76; A61B 90/361; A61B 2034/742
See application file for complete search history.

(56) References Cited

U.S. PATENT DOCUMENTS

| | | | |
|---|---|---|---|
| 5,606,346 A | 2/1997 | Kai et al. | |
| 8,181,540 B2 | 5/2012 | Loeb et al. | |
| 9,592,093 B2 | 3/2017 | Johnson et al. | |
| 9,763,741 B2 | 9/2017 | Alvarez et al. | |
| 10,543,050 B2 | 1/2020 | Itkowitz et al. | |
| 10,639,117 B2 | 5/2020 | Johnson et al. | |
| 11,690,685 B2 | 7/2023 | Savall et al. | |
| 11,712,314 B2 | 8/2023 | Thompson et al. | |
| 2006/0017701 A1 | 1/2006 | Marten et al. | |
| 2008/0091072 A1 | 4/2008 | Omori et al. | |
| 2010/0139418 A1 | 6/2010 | Loeb et al. | |
| 2013/0085511 A1 | 4/2013 | Johnson et al. | |
| 2017/0128148 A1* | 5/2017 | Johnson ................. A61B 90/10 |

(Continued)

*Primary Examiner* — Shaun L David
*Assistant Examiner* — Cherie M Poland
(74) *Attorney, Agent, or Firm* — FBT Gibbons LLP

(57) ABSTRACT

A medical system may include an input device for controlling a medical instrument. The input device may include a grasper for receiving user input and a sensor coupled to the grasper for generating sensor information related to a user presence at the grasper. The medical system may also include a processor and memory that stores instructions for receiving secondary information associated with the grasper and determining a user presence at the grasper based on the sensor information and the secondary information. A method for operating the medical system with the input device is also disclosed herein.

18 Claims, 51 Drawing Sheets

(56) References Cited

U.S. PATENT DOCUMENTS

| 2018/0161108 A1 | 6/2018 | Savall et al. | |
|---|---|---|---|
| 2018/0214223 A1 | 8/2018 | Turner | |
| 2019/0380802 A1* | 12/2019 | Savall | A61B 34/20 |
| 2020/0390510 A1 | 12/2020 | Thompson et al. | |
| 2022/0137113 A1 | 5/2022 | Luptak | |
| 2022/0382364 A1 | 12/2022 | Verner et al. | |
| 2023/0126506 A1* | 4/2023 | Wilson | A61B 34/35 |
| | | | 606/130 |

* cited by examiner 338-1

338-2

340-1

340-2

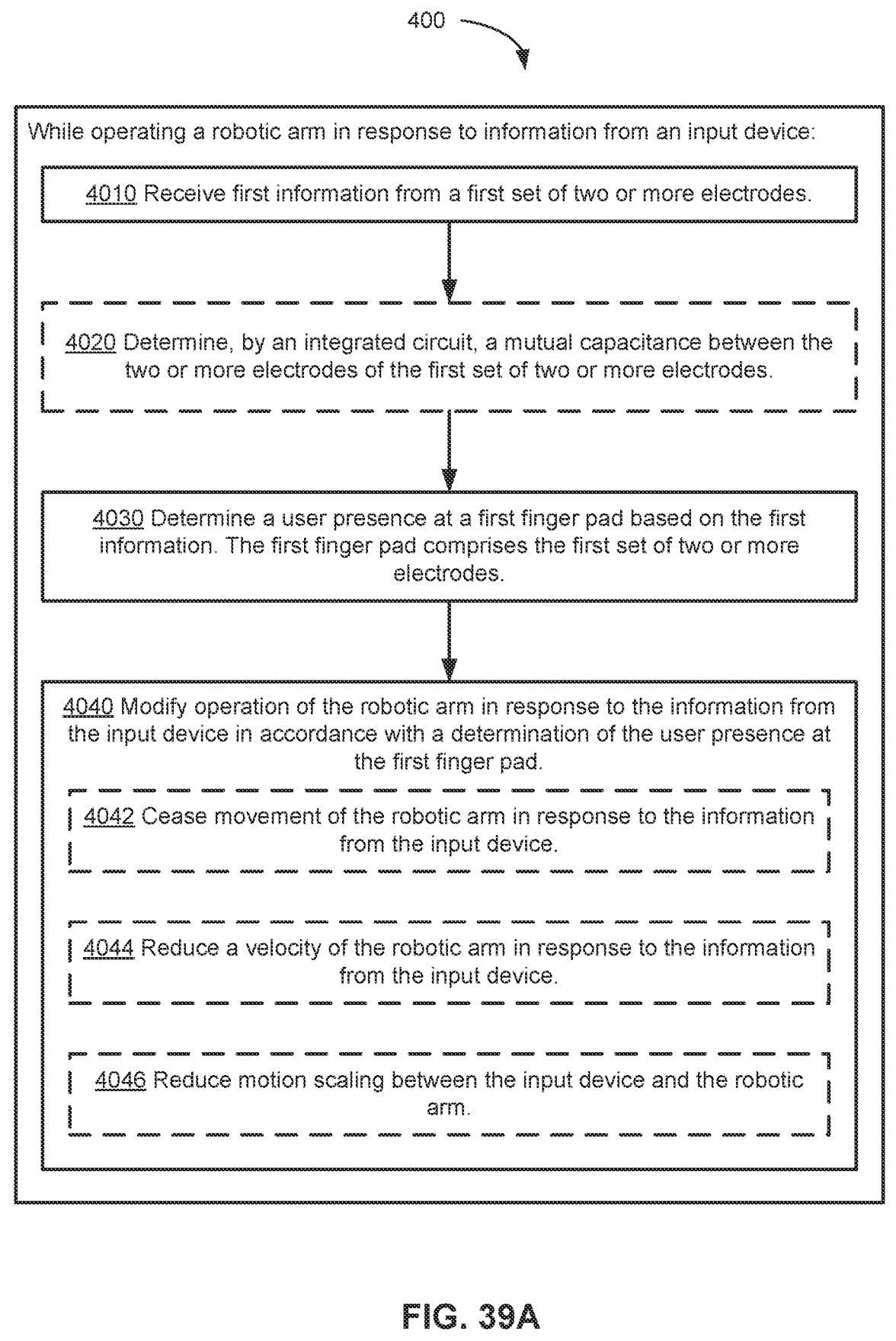

400

While operating a robotic arm in response to information from an input device:

4010 Receive first information from a first set of two or more electrodes.

4020 Determine, by an integrated circuit, a mutual capacitance between the two or more electrodes of the first set of two or more electrodes.

4030 Determine a user presence at a first finger pad based on the first information. The first finger pad comprises the first set of two or more electrodes.

4040 Modify operation of the robotic arm in response to the information from the input device in accordance with a determination of the user presence at the first finger pad.

4042 Cease movement of the robotic arm in response to the information from the input device.

4044 Reduce a velocity of the robotic arm in response to the information from the input device.

4046 Reduce motion scaling between the input device and the robotic arm.

FIG. 39A

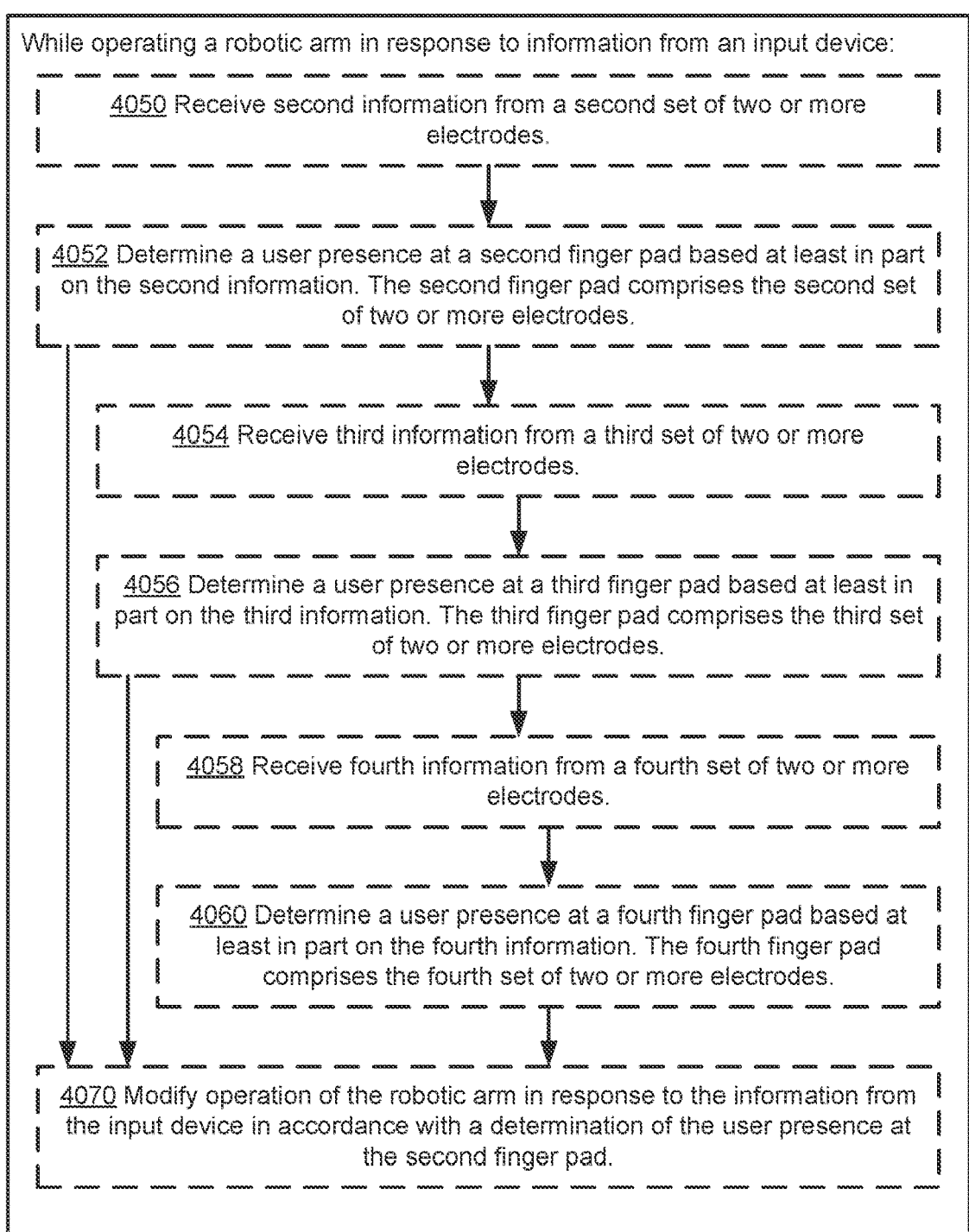

400

While operating a robotic arm in response to information from an input device:

4050 Receive second information from a second set of two or more electrodes.

4052 Determine a user presence at a second finger pad based at least in part on the second information. The second finger pad comprises the second set of two or more electrodes.

4054 Receive third information from a third set of two or more electrodes.

4056 Determine a user presence at a third finger pad based at least in part on the third information. The third finger pad comprises the third set of two or more electrodes.

4058 Receive fourth information from a fourth set of two or more electrodes.

4060 Determine a user presence at a fourth finger pad based at least in part on the fourth information. The fourth finger pad comprises the fourth set of two or more electrodes.

4070 Modify operation of the robotic arm in response to the information from the input device in accordance with a determination of the user presence at the second finger pad.

FIG. 39B

410

4110 Receive, from a sensor coupled to a grasper of the input device, sensor information related to a user presence at the grasper.

4120 Receive secondary information associated with the grasper.

4130 Determine user control at the grasper based on the sensor information and the secondary information.

4132 The secondary information includes a time threshold, and determining the user presence at the grasper includes comparing a duration over which the sensor information indicates a lack of the user presence and the time threshold.

4134 The secondary information includes information indicating a change in a configuration of the input device at a first time and a second time that is subsequent to the first time, and determining the user presence determining the user presence at the grasper includes comparing the change in the configuration of the input device and a configuration change threshold.

4136 The secondary information includes information indicating a change in a configuration of the medical instrument at a first time and a second time that is subsequent to the first time, and determining the user presence at the grasper includes comparing the change in the configuration of the medical instrument and a configuration change threshold.

Figure 41:
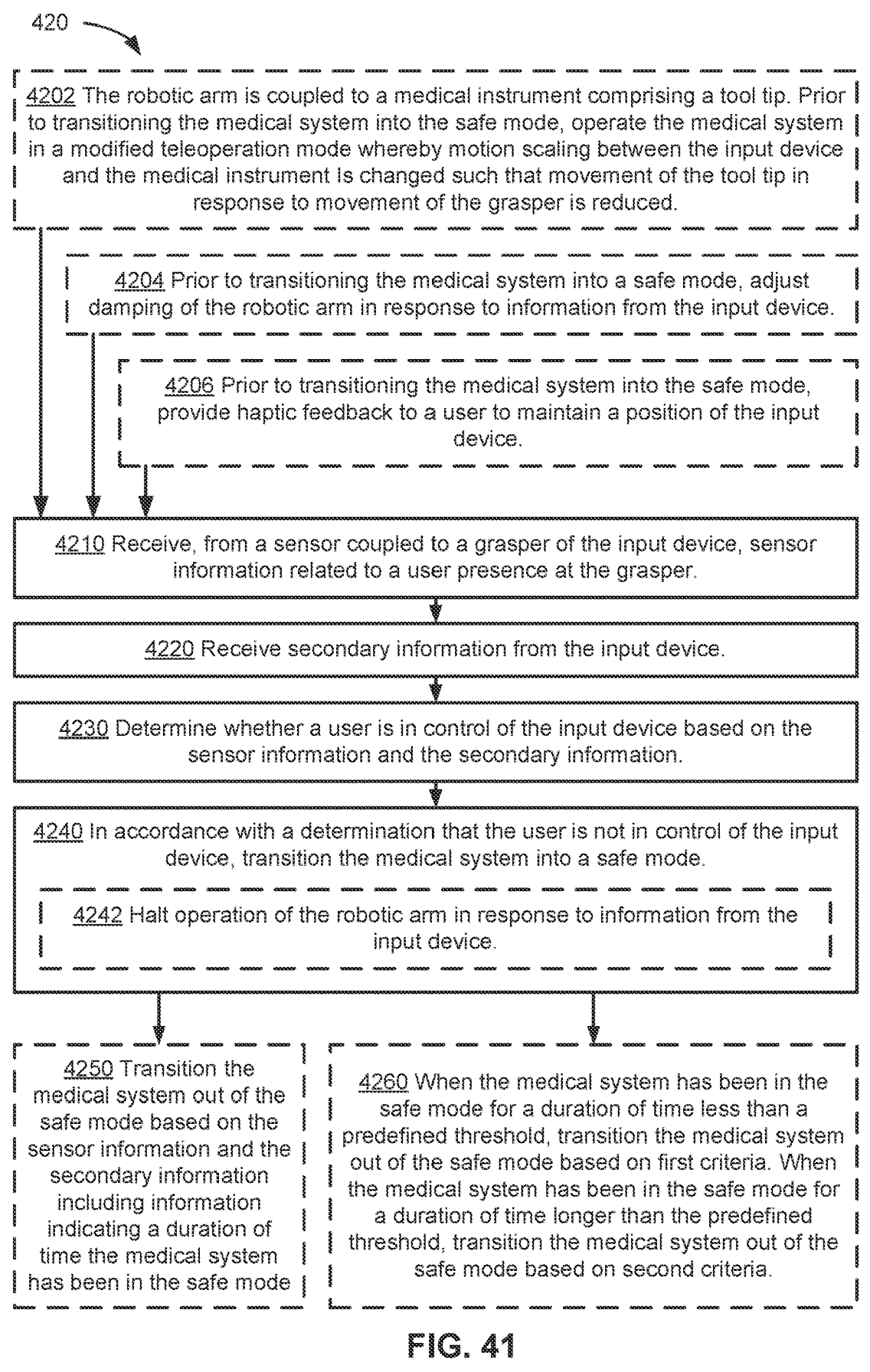

4202 The robotic arm is coupled to a medical instrument comprising a tool tip. Prior to transitioning the medical system into the safe mode, operate the medical system in a modified teleoperation mode whereby motion scaling between the input device and the medical instrument Is changed such that movement of the tool tip in response to movement of the grasper is reduced.

4204 Prior to transitioning the medical system into a safe mode, adjust damping of the robotic arm in response to information from the input device.

4206 Prior to transitioning the medical system into the safe mode, provide haptic feedback to a user to maintain a position of the input device.

4210 Receive, from a sensor coupled to a grasper of the input device, sensor information related to a user presence at the grasper.

4220 Receive secondary information from the input device.

4230 Determine whether a user is in control of the input device based on the sensor information and the secondary information.

4240 In accordance with a determination that the user is not in control of the input device, transition the medical system into a safe mode.

4242 Halt operation of the robotic arm in response to information from the input device.

4250 Transition the medical system out of the safe mode based on the sensor information and the secondary information including information indicating a duration of time the medical system has been in the safe mode

4260 When the medical system has been in the safe mode for a duration of time less than a predefined threshold, transition the medical system out of the safe mode based on first criteria. When the medical system has been in the safe mode for a duration of time longer than the predefined threshold, transition the medical system out of the safe mode based on second criteria.

REDUCTION OF FALSE POSITIVE HAPTIC INPUTS IN A ROBOTIC SURGICAL SYSTEM

CROSS-REFERENCE TO RELATED APPLICATION(S)

This application claims the benefit of U.S. Provisional Application No. 63/270,557, filed on Oct. 21, 2021, entitled "Reduction of false Positive Haptic Inputs in a Robotic Surgical System," which is hereby incorporated by reference in its entirety.

This application is related to U.S. patent application Ser. No. 17/970,505, filed on Oct. 20, 2022, issued as U.S. Pat. No. 12,484,983 on Dec. 2, 2025, entitled "Drift Detection of a Haptic Input Device in a Robotic Surgical System," which is hereby incorporated by reference in its entirety.

TECHNICAL FIELD

The systems and methods disclosed herein are directed to input devices, and more particularly to input devices for robotic surgical systems.

BACKGROUND

A robotically enabled medical system is capable of performing a variety of medical procedures, including both minimally invasive procedures, such as laparoscopy, and non-invasive procedures, such as endoscopy (e.g., bronchoscopy, ureteroscopy, gastroscopy, etc.).

Such robotic medical systems may include robotic arms configured to control the movement of medical tool(s) during a given medical procedure. The robotic medical system may also include an input device used to control the positioning and/or actuation of the medical tool(s) during the medical procedure.

SUMMARY

The systems, methods and devices of this disclosure each have several innovative aspects, no single one of which is solely responsible for the desirable attributes disclosed herein.

In one aspect, an input device for controlling a robotic surgical tool is provided. The input device can include a first pair of opposing links and a second pair of opposing links. The first pair of opposing links and the second pair of opposing links can be arranged radially symmetrically. The input device can be configured to control operation of the robotic surgical tool.

In some configurations, the first pair of opposing links is longer than the second pair of opposing links. The first pair of opposing links can be of equal length as the second pair of opposing links. Each of the first pair of opposing links can include a finger pad. Each of the second pair of opposing links can include a clutch button. The clutch button can be a push button. The clutch button can include a protruding ledge. The input device can include at least one clutch button. The at least one clutch button, when actuated, can be configured to decouple the input device from controlling operation of the robotic surgical tool. Each of the first pair of opposing links and each of the second pair of opposing links can be coupled to a central longitudinal member. The proximal ends of each of the first pair of opposing links and each of the second pair of opposing links can be configured to radially move relative to the central longitudinal member. Each of the first pair of opposing links can be configured to move together. Each of the second pair of opposing links can be configured to move together. The first pair of opposing links and the second pair of opposing can be are configured to move together. Each of the first pair of opposing links can be configured to move together, such that proximal ends of the first pair of opposing links are positioned equally distant from the central longitudinal member. The first pair of opposing links can be constrained to move together. The second pair of opposing links can be constrained to move together. The central longitudinal member can include a hall effect sensor.

In another aspect, an input device for controlling a robotic surgical tool can be provided. The input device can include a multi-link grasper comprising three or more links coupled to a central longitudinal member. The three or more links can be spaced less than 180 degrees from one another about the central longitudinal member. The multi-link grasper can be configured for controlling operation of the robotic surgical tool. The three or more links can be equally spaced from each other. Each of the three or more links can be configured to move from an open position where proximal ends of each of the three or more links are positioned radially away from the central longitudinal member to a closed position where the proximal ends of each of the three or more links are positioned radially close to the central longitudinal member. Each of the three or more links can be biased in the open position.

In yet another aspect, an input device for controlling a surgical tool can be provided. The input device can include a multi-link grasper comprising two or more links about a central longitudinal member for controlling operation of the surgical tool.

In some configurations, the at least one of the two or more links can include a finger input. The finger input can be capable of operating in a first mode and in a second mode. In the first mode, the finger input can operate as a finger clutch and, in the second mode, the finger clutch operates as a selecting tool. The finger input can include a push input. The finger input can include a rotary input. The central longitudinal member can include a sensor for detecting a mode of the finger input. The sensor can be coupled to the central longitudinal member. Each of the two or more links can include a curved face at a proximal end. The curved face can wrap around the central longitudinal member. The input device can include a rack gear. The rack gear can include gear teeth configured to mate with each of the two or more links. Each of the two or more links can be configured to rotate relative to the rack gear, wherein each of the two or more links are configured to engage with the rack gear such that rotation of one of the two or more links causes rotation of remaining links of the two or more links. Each of the two or more links can include bevel gear teeth configured to connect motion of each of the two or more links to the remainder of the two or more links.

In yet another aspect, a physician console can be provided. The physician console can include an input device including a first grasper and a second grasper. The input device can be configured to control a surgical tool. At least one of the first and second grasper can include a four-link radially symmetrical grasper for controlling operation of the surgical tool.

In accordance with some embodiments, an input device for controlling operation of a robotic arm is provided. The input device can include a first finger pad that includes a first set of two or more electrodes for determining a user presence at the first finger pad. The input device can also include a processor for modifying operation of the robotic arm in response to information from the input device in accordance with a determination of the user presence at the first finger pad.

In accordance with some embodiments, a method for operating a surgical tool via an input device is performed by one or more processors executing instructions store in memory. The method includes, while operating a robotic arm in response to information from an input device: (i) receiving first information from a first set of two or more electrodes, (ii) determining a user presence at a first finger pad based on the first information, and (iii) modifying operation of the robotic arm in response to the information from the input device in accordance with a determination of the user presence at the first finger pad. In some embodiments, modifying teleoperation of the robotic arm in response to the information from the input device may include any of: ceasing movement of the robotic arm in response to the information from the input device, reducing a velocity of the robotic arm in response to the information from the input device, or reducing motion scaling between the input device and the robotic arm.

In accordance with some embodiments, a medical system includes an input device for controlling operation of a robotic arm. The input device includes a grasper, the grasper includes a first finger pad, and the first finger pad includes two or more electrodes. The input device also includes an integrated circuit for measuring a mutual capacitance between the two or more electrodes of the first set of two or more electrodes for determining a user presence at the first finger pad.

In accordance with some embodiments, a medical system includes an input device for controlling a medical instrument. The input device includes a grasper for receiving user input and a sensor coupled to the grasper for generating sensor information related to a user presence at the grasper. The input device includes a processor and memory storing instructions for execution by the processor. The stored instructions include instructions for receiving secondary information associated with the grasper and determining a user presence at the grasper based on the sensor information and the secondary information.

In accordance with some embodiments, an input device for controlling operation of a robotic arm includes a grasper and a sensor coupled to the grasper for generating sensor information related to a user presence at the grasper. The input device also includes a processor and memory storing instructions for execution by the processor. The stored instructions include instructions for receiving secondary information from the input device, determining whether a user is in control of the input device based on the sensor information and the secondary information, and in accordance with a determination that the user is not in control of the input device, transitioning the medical system into a safe mode.

In accordance with some embodiments, a medical system includes an input device for controlling operation of a robotic arm. The input device includes a grasper and a sensor coupled to the grasper for generating sensor information related to a user presence at the grasper. The medical system also includes a processor and memory storing instructions for execution by the processor. The stored instructions include instructions for receiving secondary information from the input device, determining whether a user is in control of the input device based on the sensor information and the secondary information, and in accordance with a determination that the user is not in control of the input device, transitioning the medical system into a safe mode.

In accordance with some embodiments, a method for operating a medical system that includes an input device for controlling a medical instrument is performed by one or more processors executing instructions stored in memory. The method includes receiving, from a sensor coupled to a grasper of the input device, sensor information related to a user presence at the grasper. The method also includes receiving secondary information associated with the grasper and determining user control at the grasper based on the sensor information and the secondary information.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 39A and 39B are a flowchart illustrating a method for operating a surgical tool via the input device of FIG. 21 in accordance with some embodiments.

FIG. 40 is a flowchart illustrating a method of operating a medical system for controlling a medical instrument using the input device of FIG. 21 in accordance with some embodiments.

FIG. 41 is a flowchart illustrating a method of operating a medical system that includes the input device of FIG. 21 in accordance with some embodiments.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
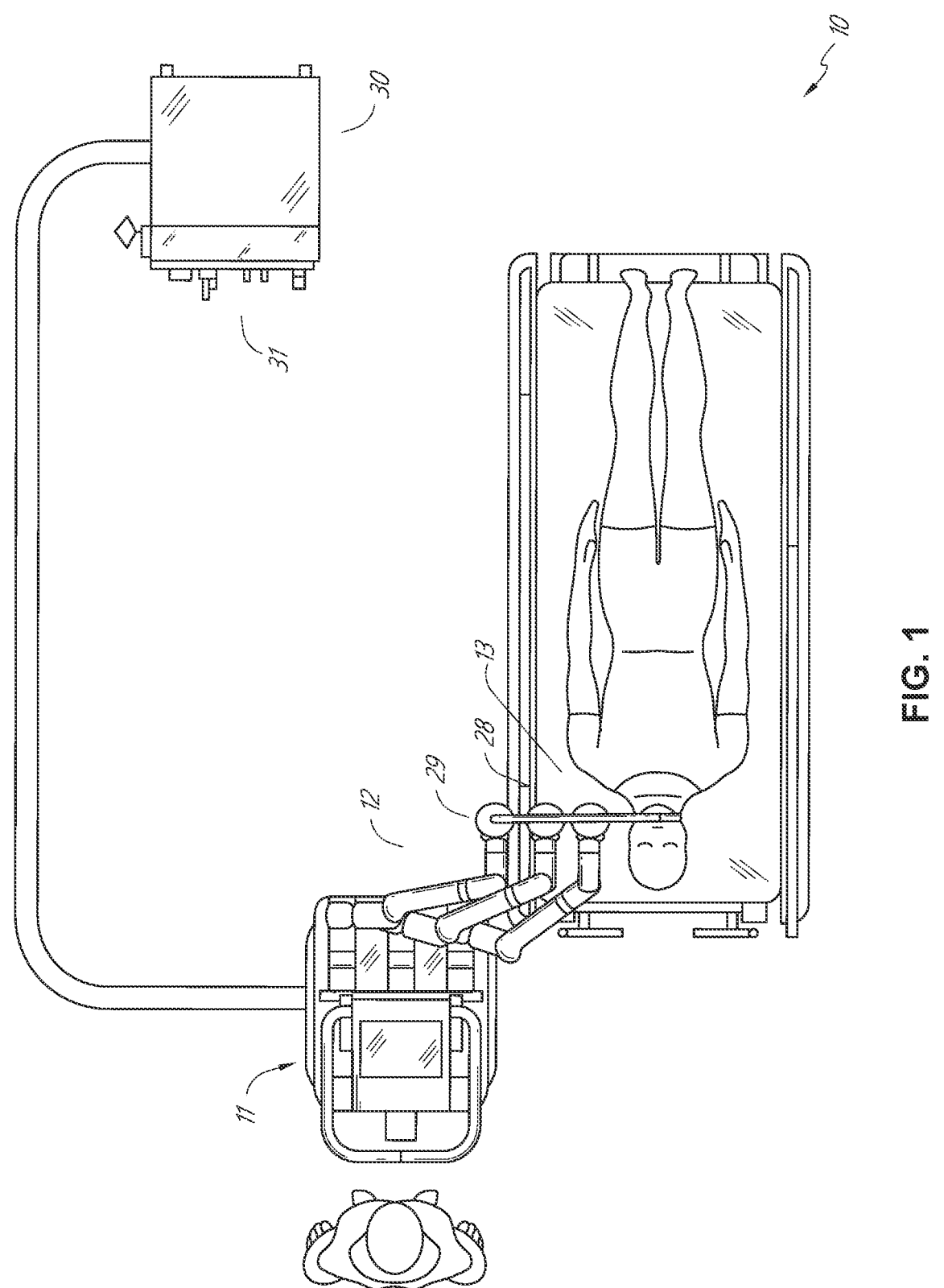
FIG. 1 illustrates an embodiment of a cart-based robotic system arranged for diagnostic and/or therapeutic bronchoscopy.
Figure 2:
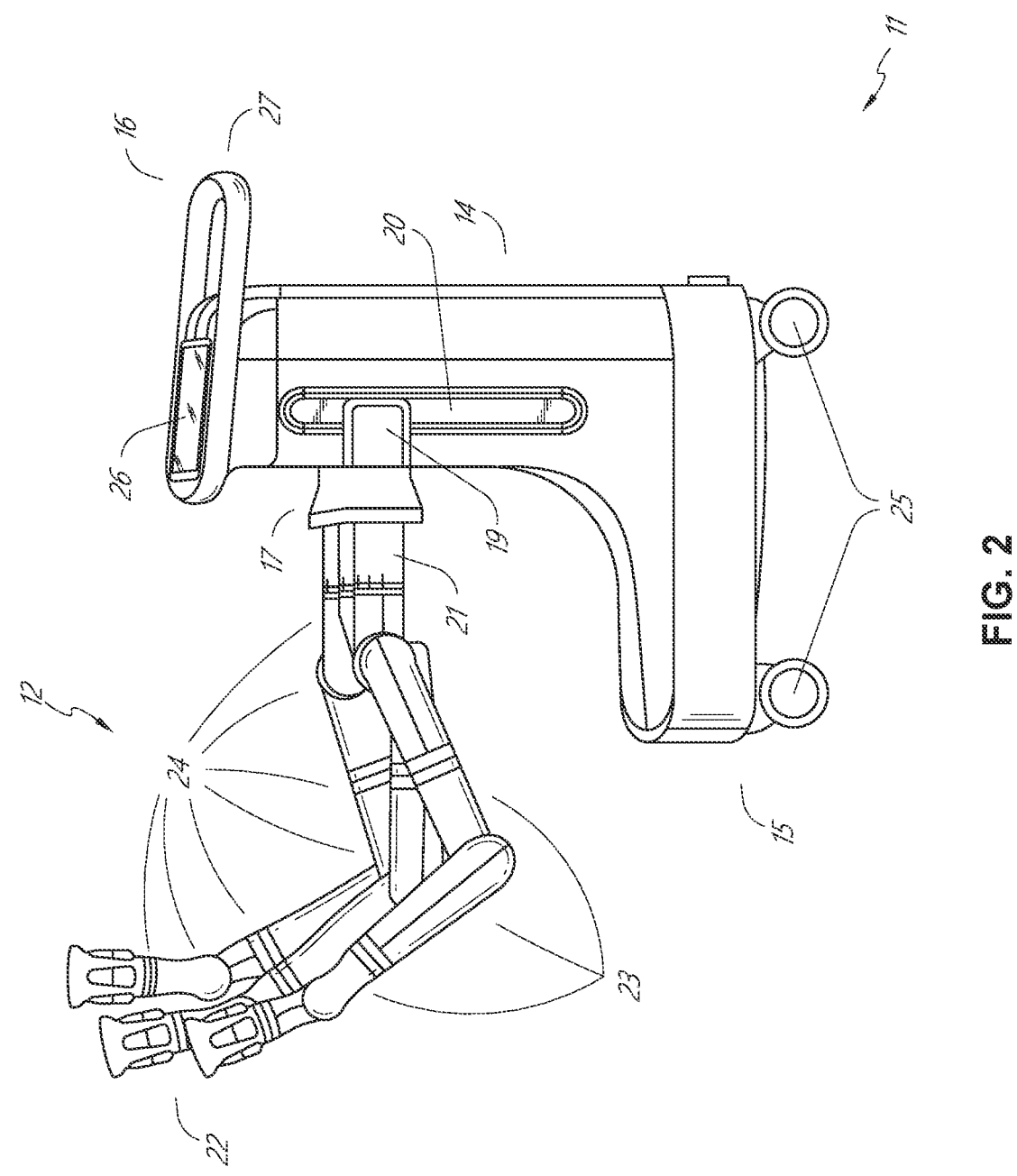
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
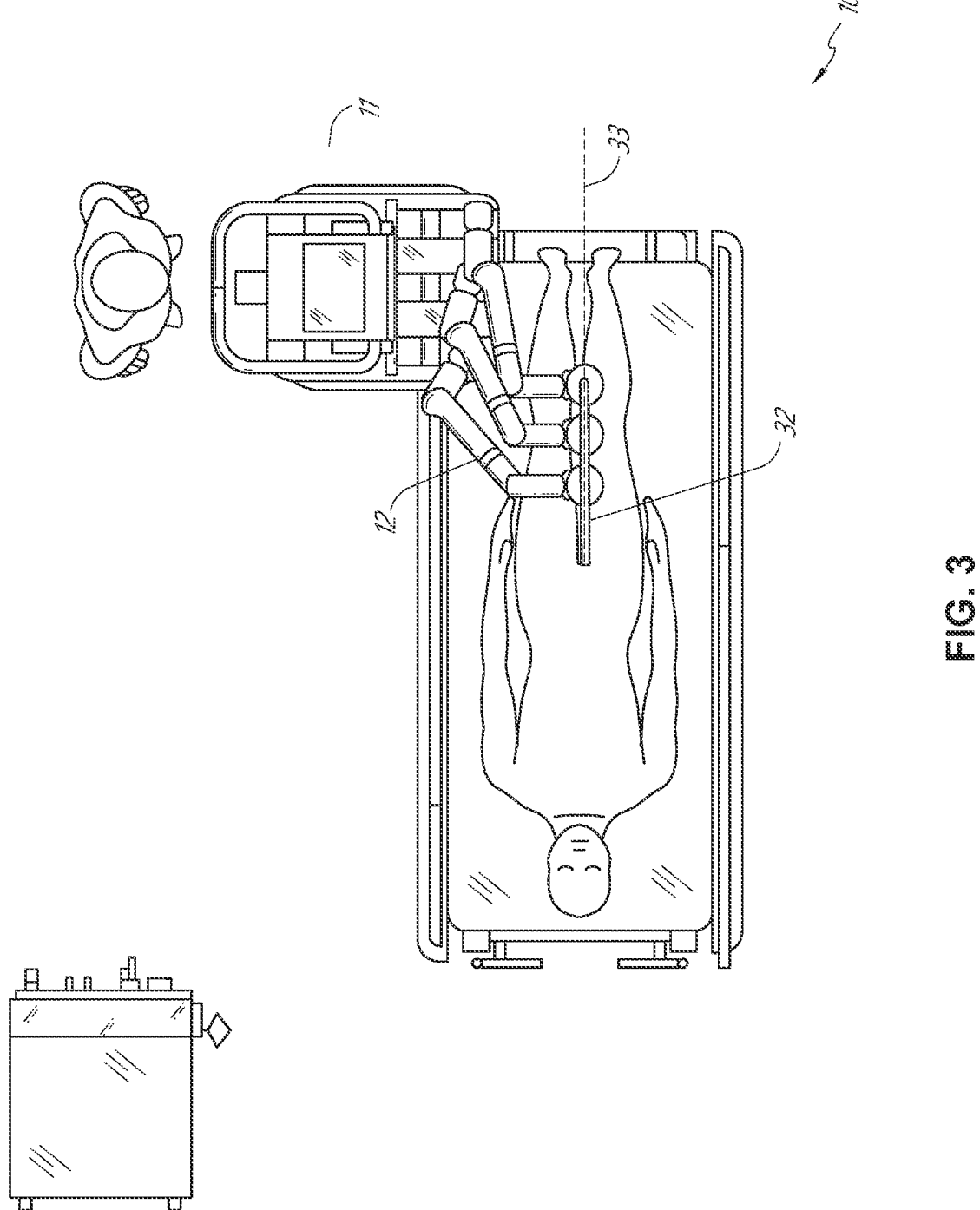
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
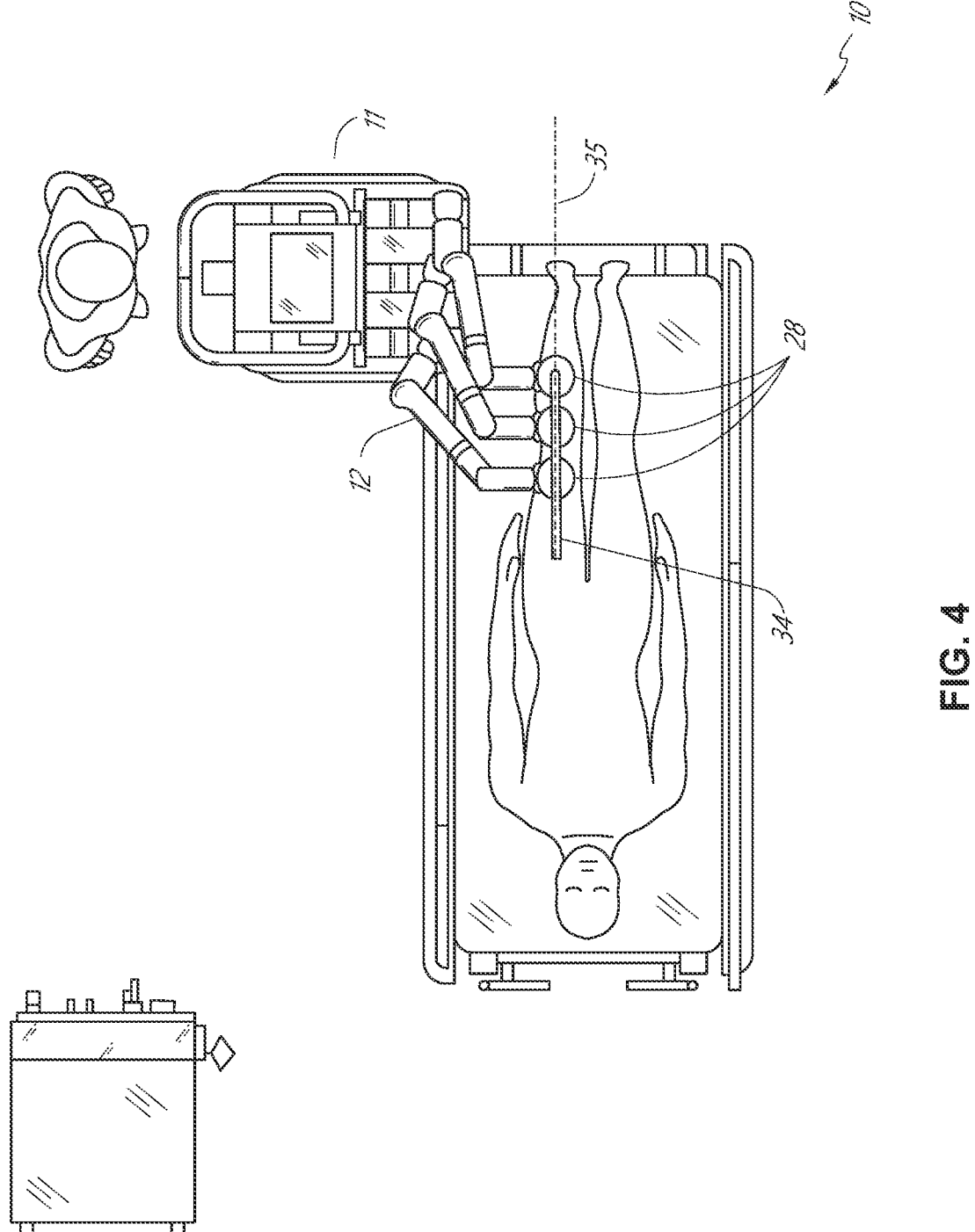
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
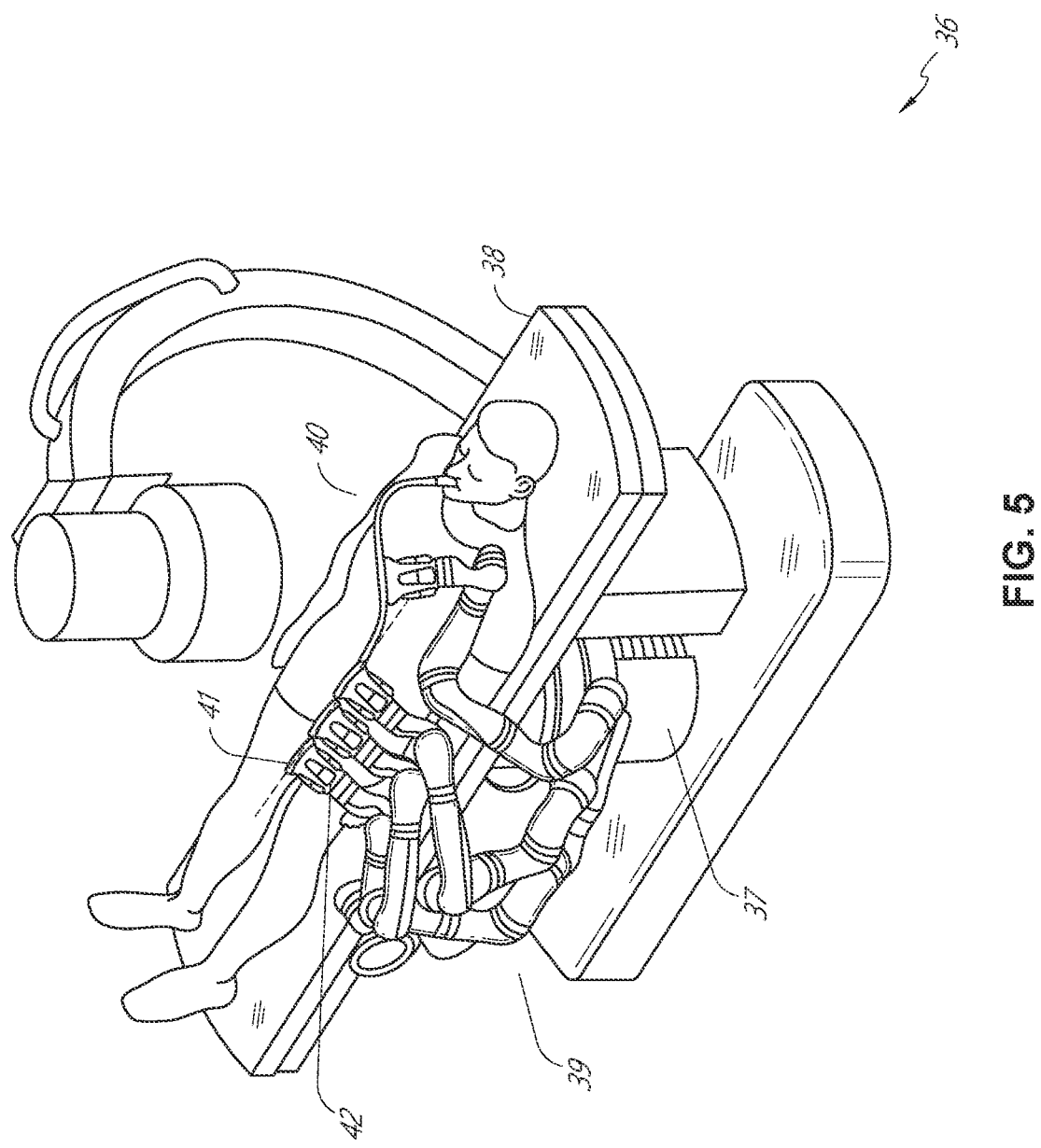
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a broncho-scopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipu-late an elongated medical instrument, such as a broncho-scope 40 in FIG. 5, through or along a virtual rail 41 formed from the linear alignment of the instrument drivers 42. In practice, a C-arm for providing fluoroscopic imaging may be positioned over the patient's upper abdominal area by plac-ing the emitter and detector around the table 38.

Figure 6:
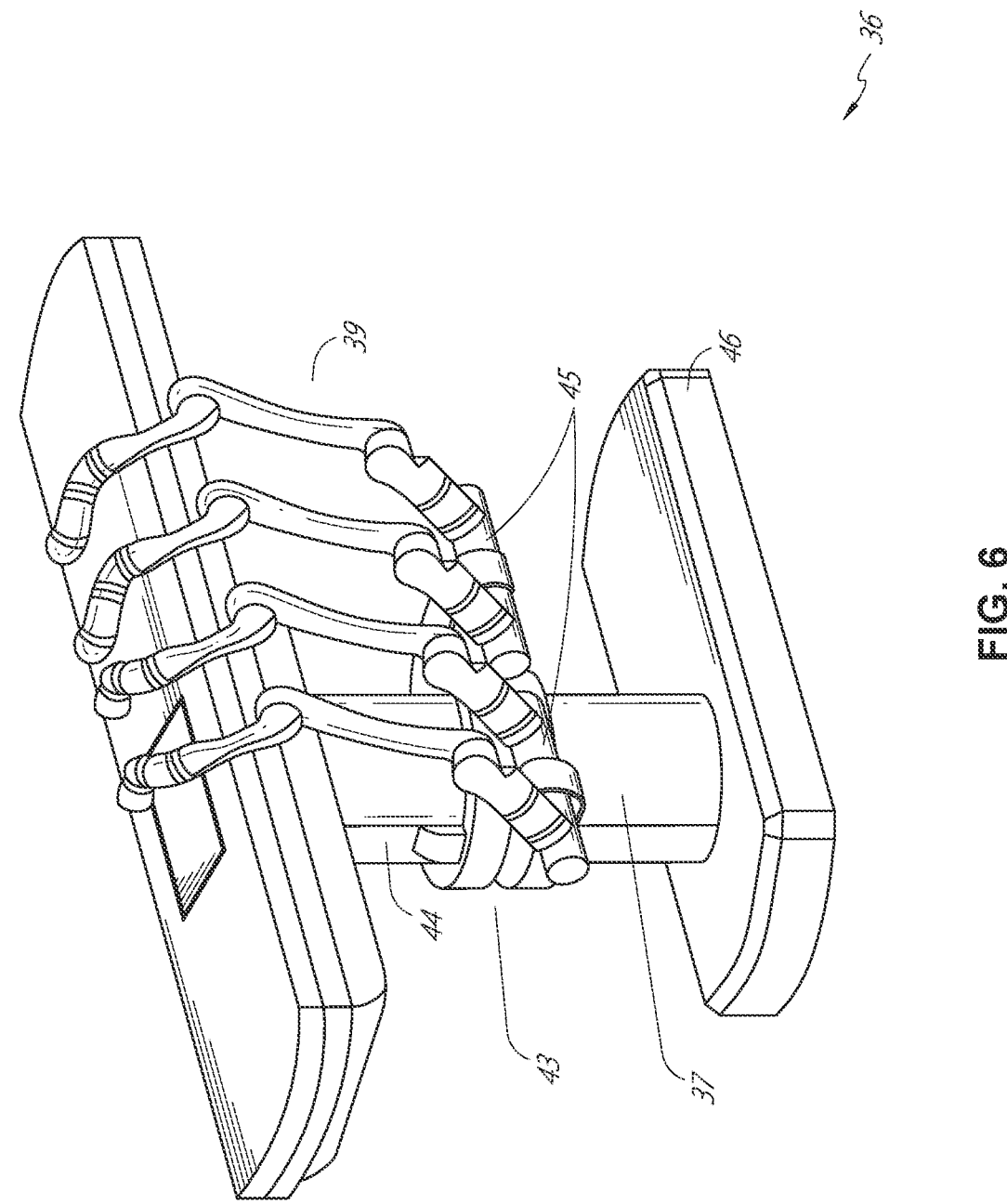
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually posi-tioned on the column and may translate and/or rotate inde-pendently of the other carriages. While the carriages 43 need not surround the column 37 or even be circular, the ring-shape as shown facilitates rotation of the carriages 43 around the column 37 while maintaining structural balance. Rota-tion and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
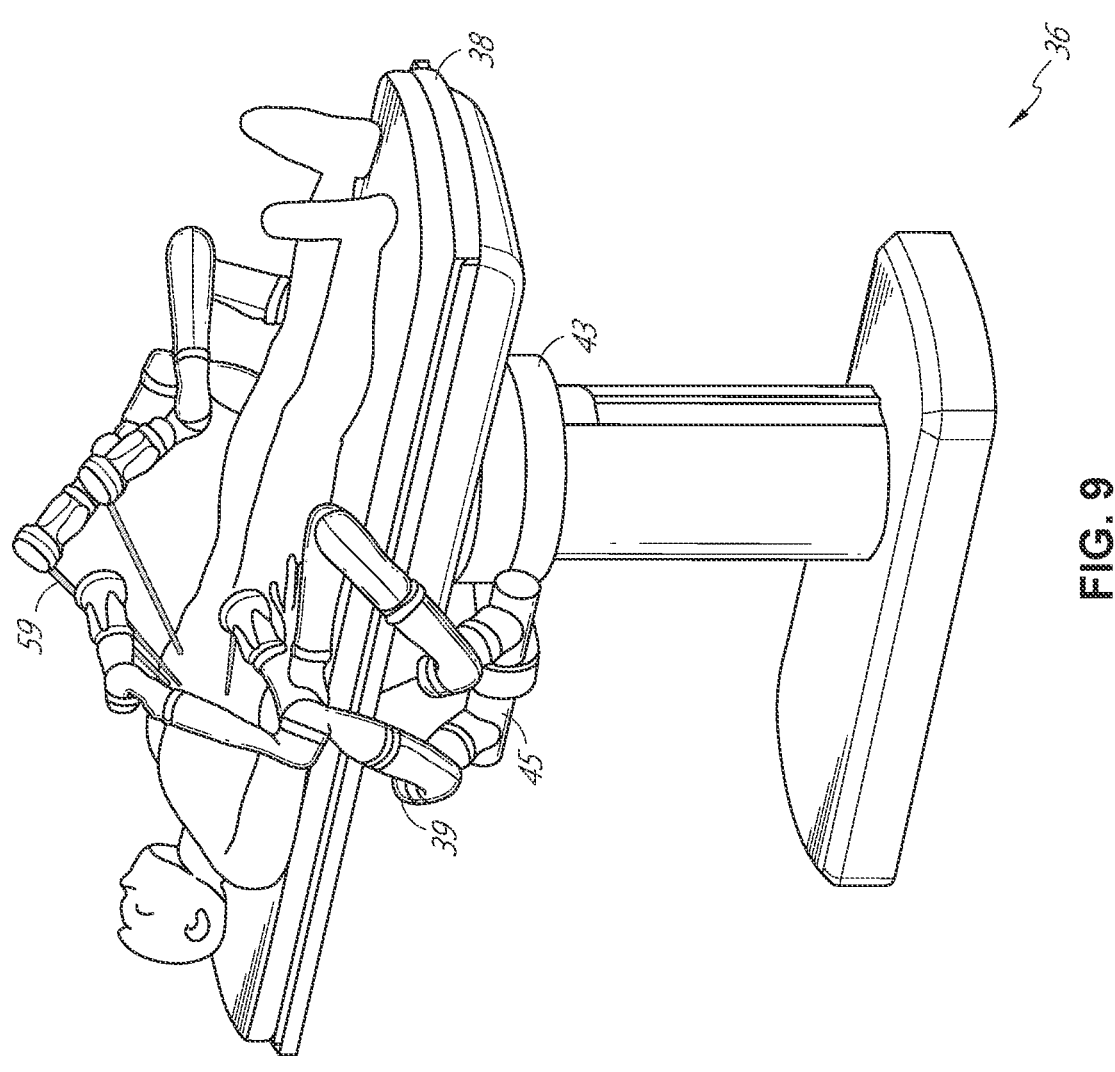
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropri-ately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier compo-nents to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the function-ality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Addi-tionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, naviga-tion, and tracking information. In some embodiments, the tower may also contain holders for gas tanks to be used for insufflation.

Figure 7:
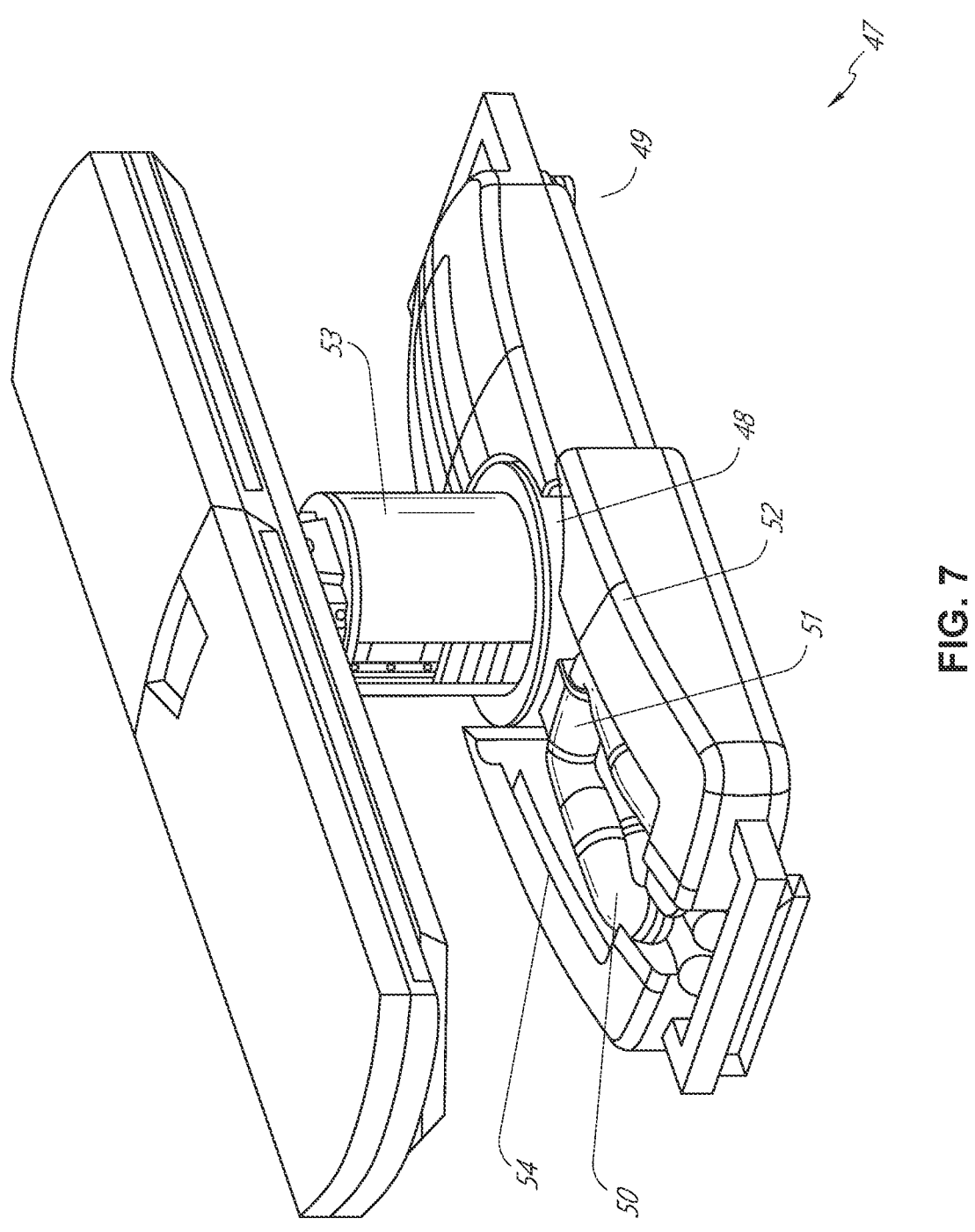
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
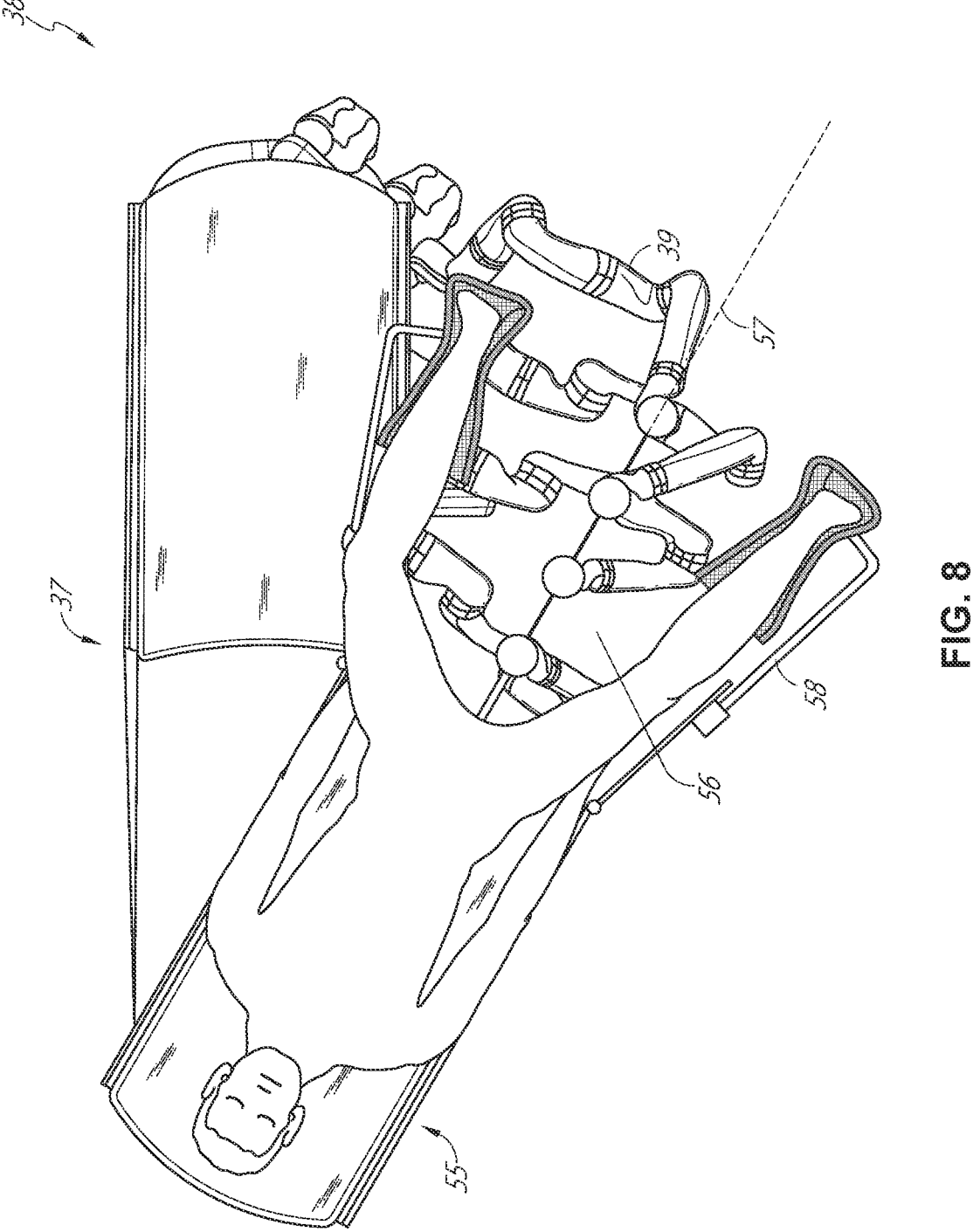
FIG. 8 illustrates an embodiment of a table-based robotic system configured for a ureteroscopic procedure.

FIG. 8 illustrates an embodiment of a robotically-enabled table-based system configured for a ureteroscopic proce-dure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
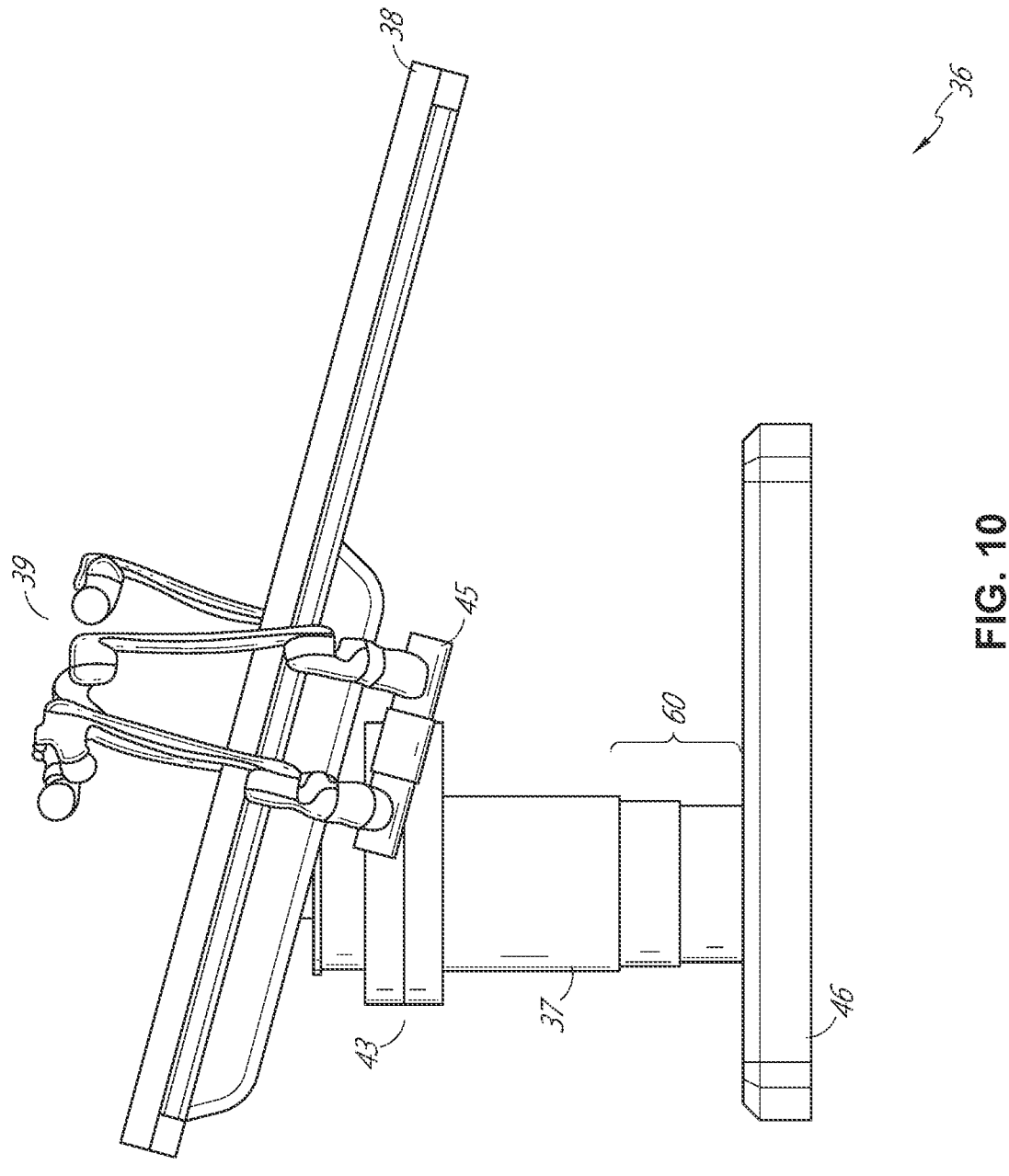
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
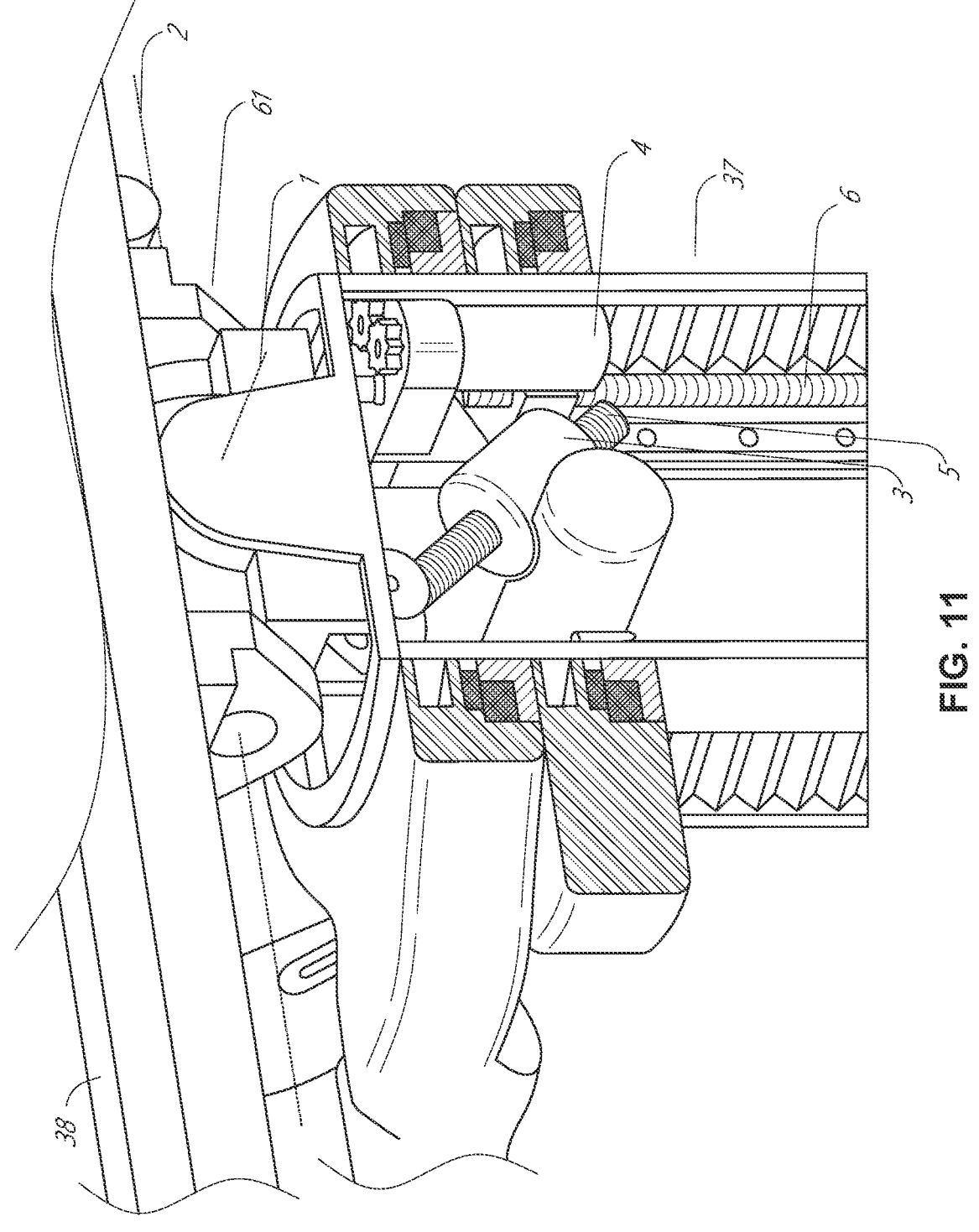
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw S would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
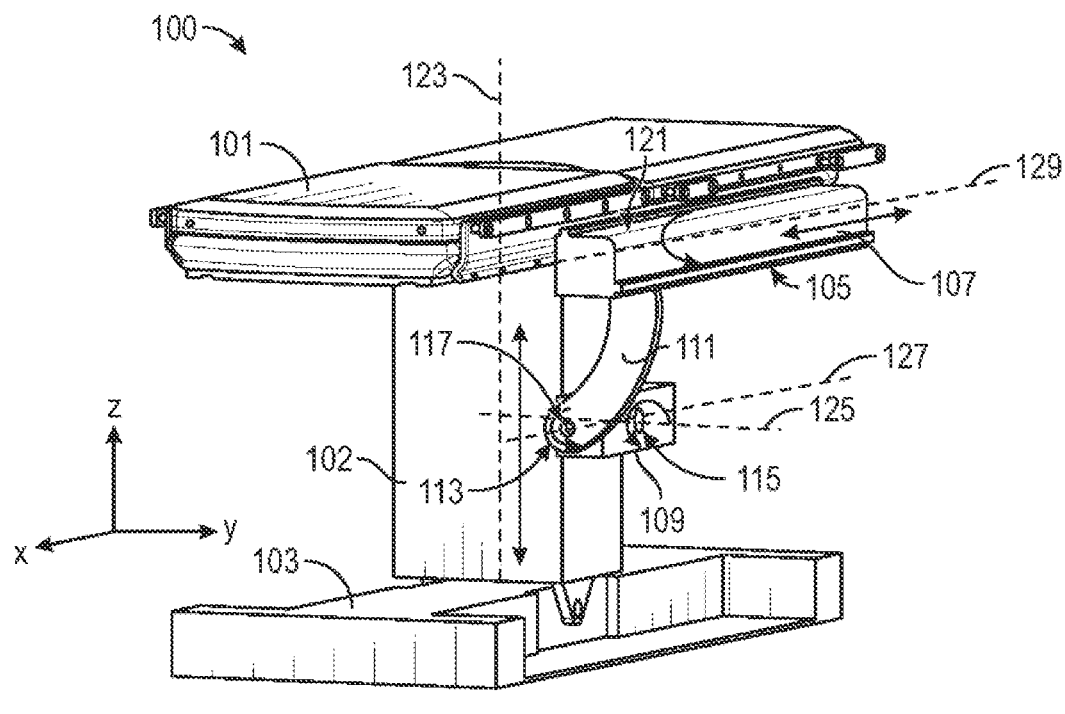
FIG. 12 illustrates an alternative embodiment of a table-based robotic system.
Figure 13:
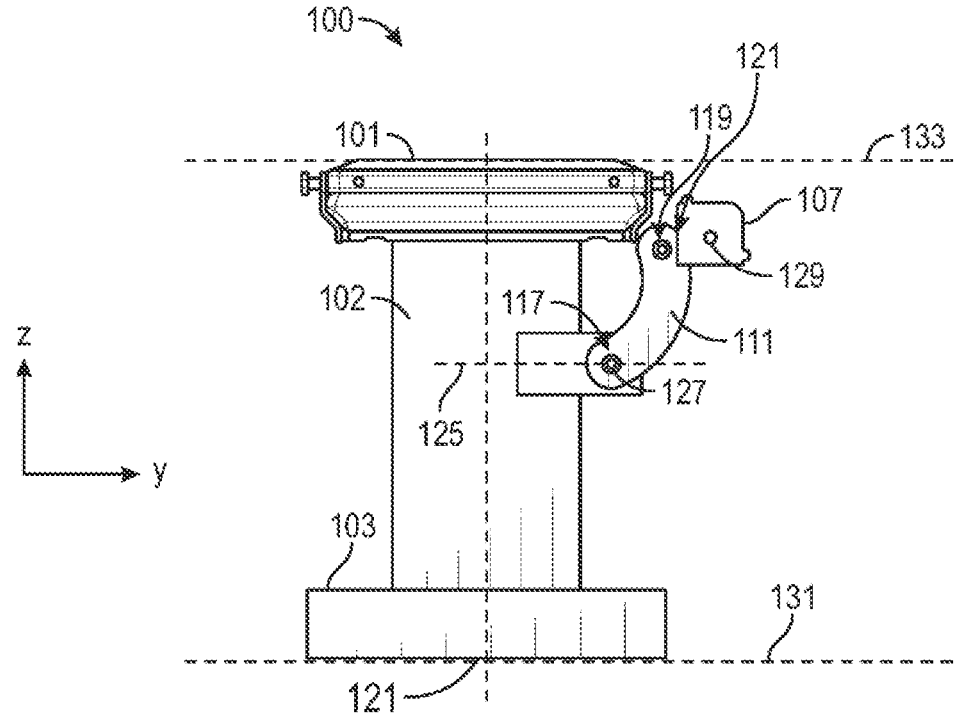
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
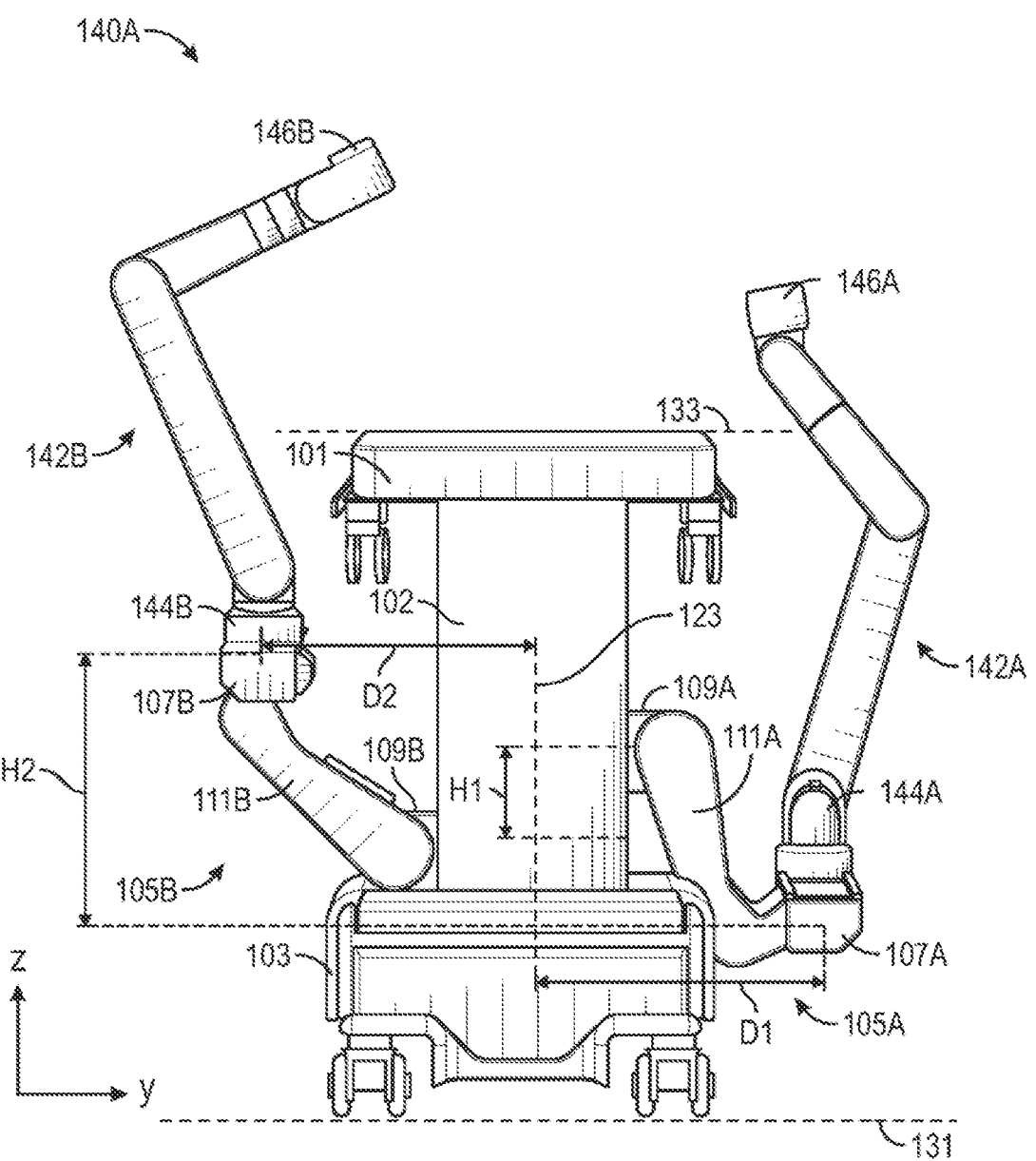
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
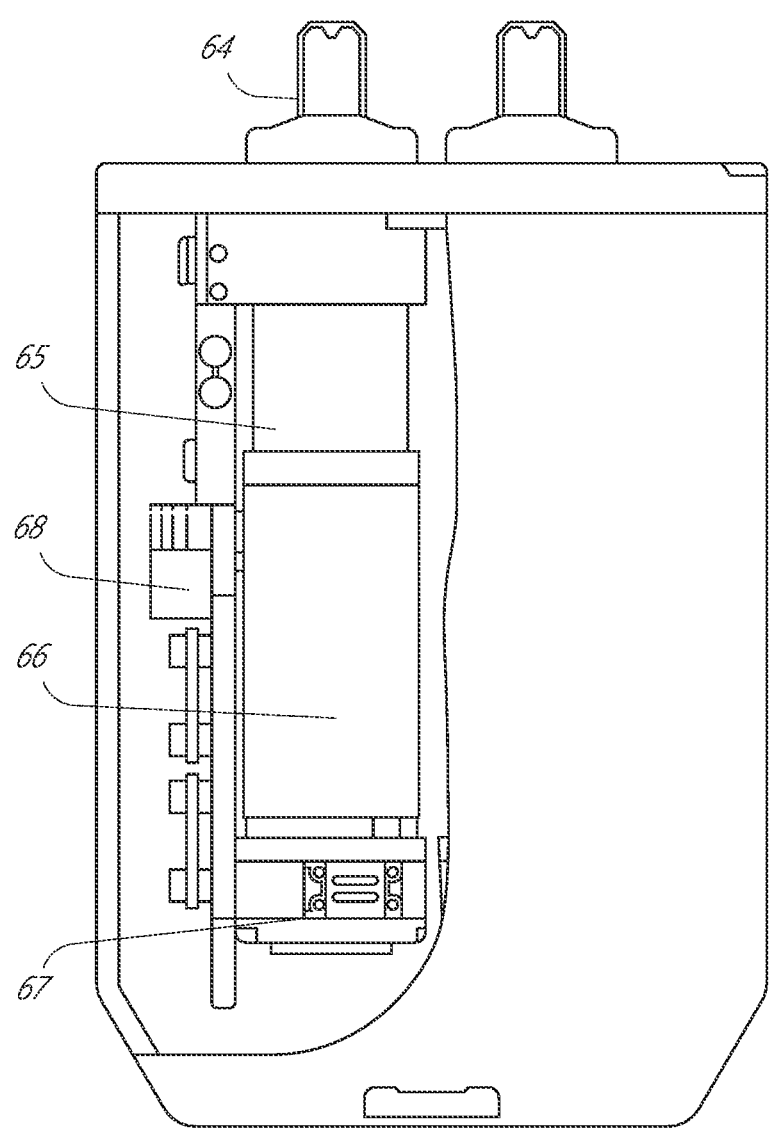
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
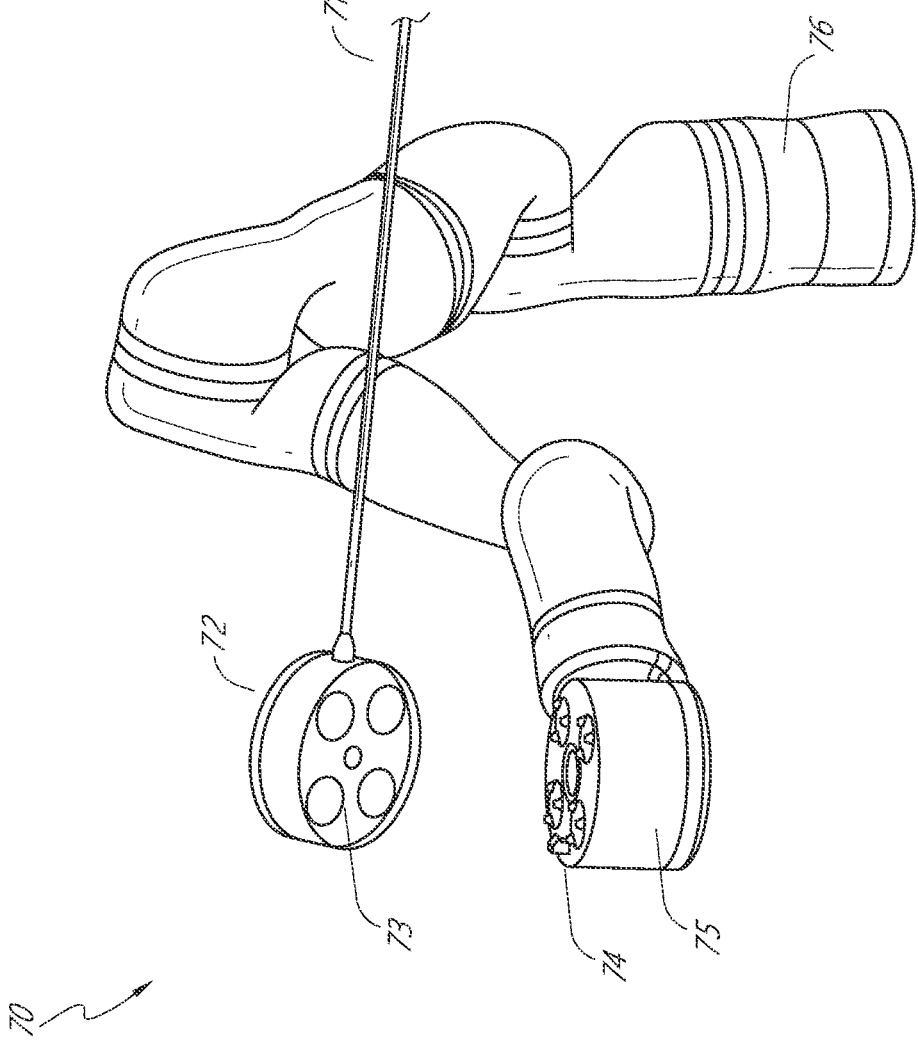
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
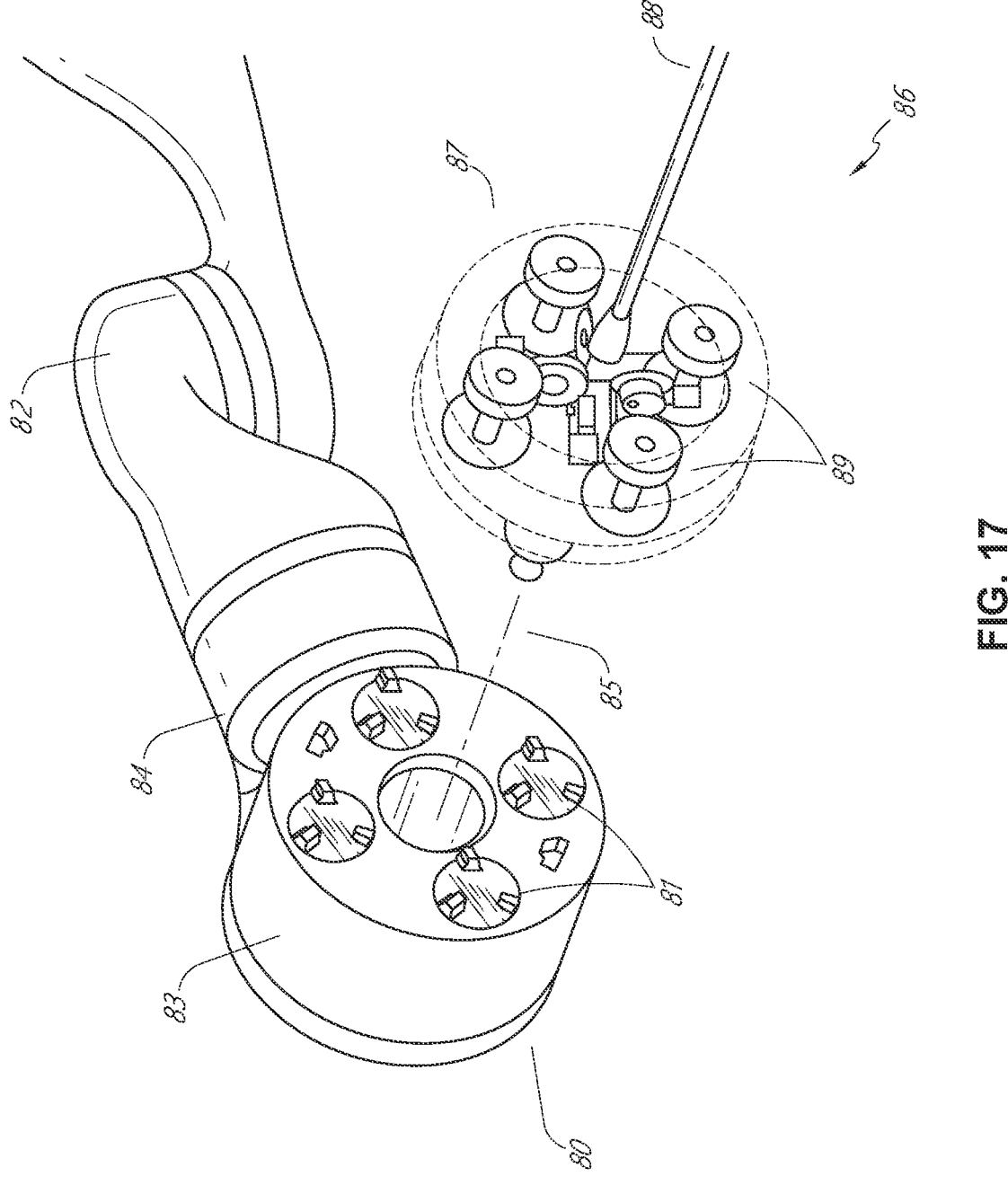
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument.

As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
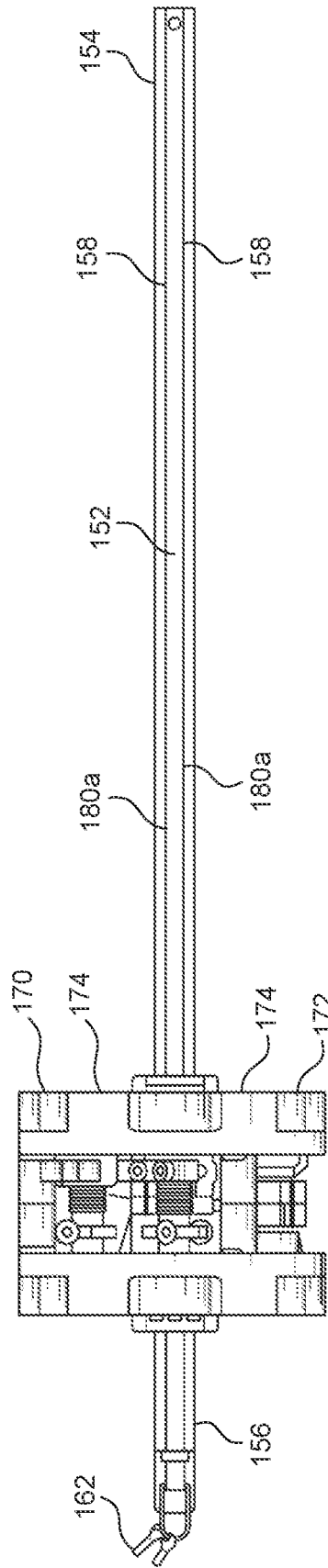
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
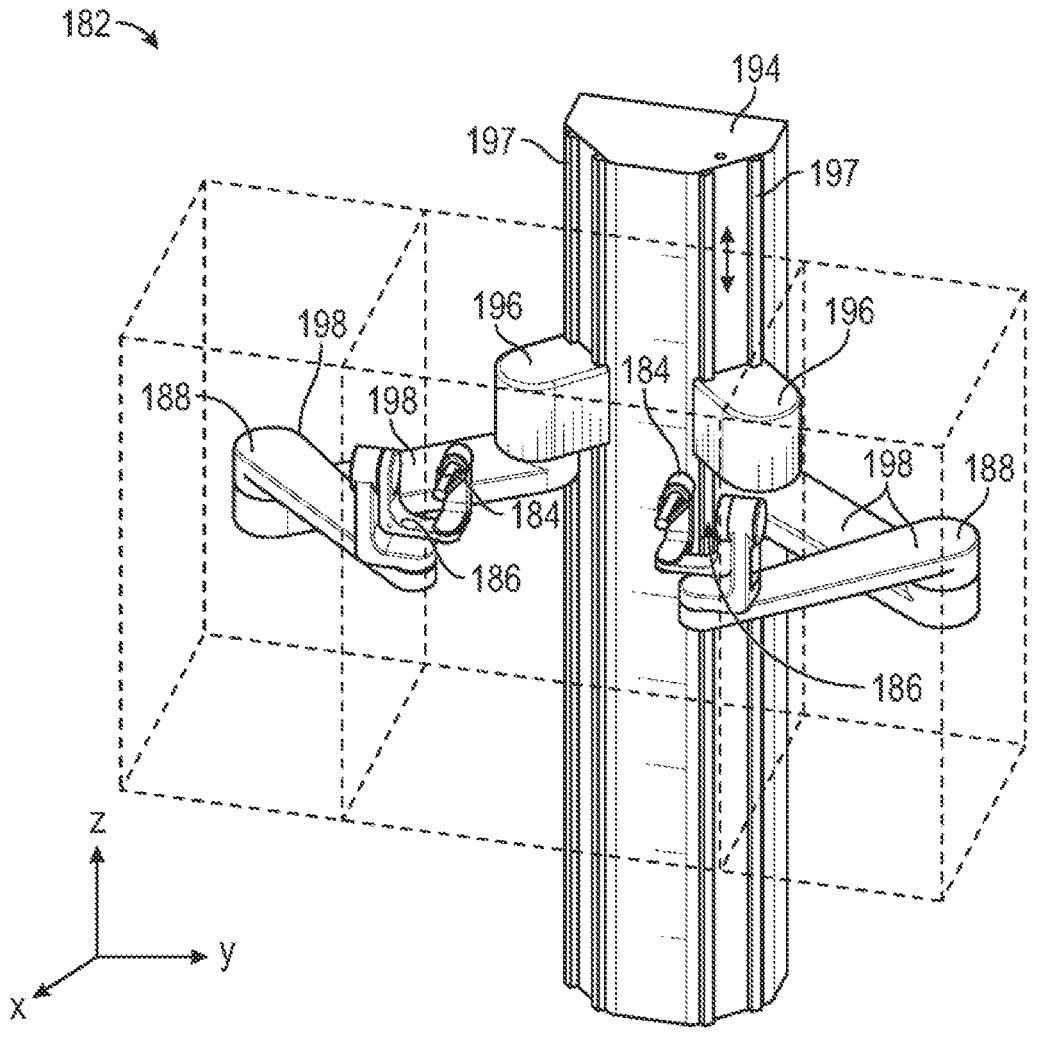
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
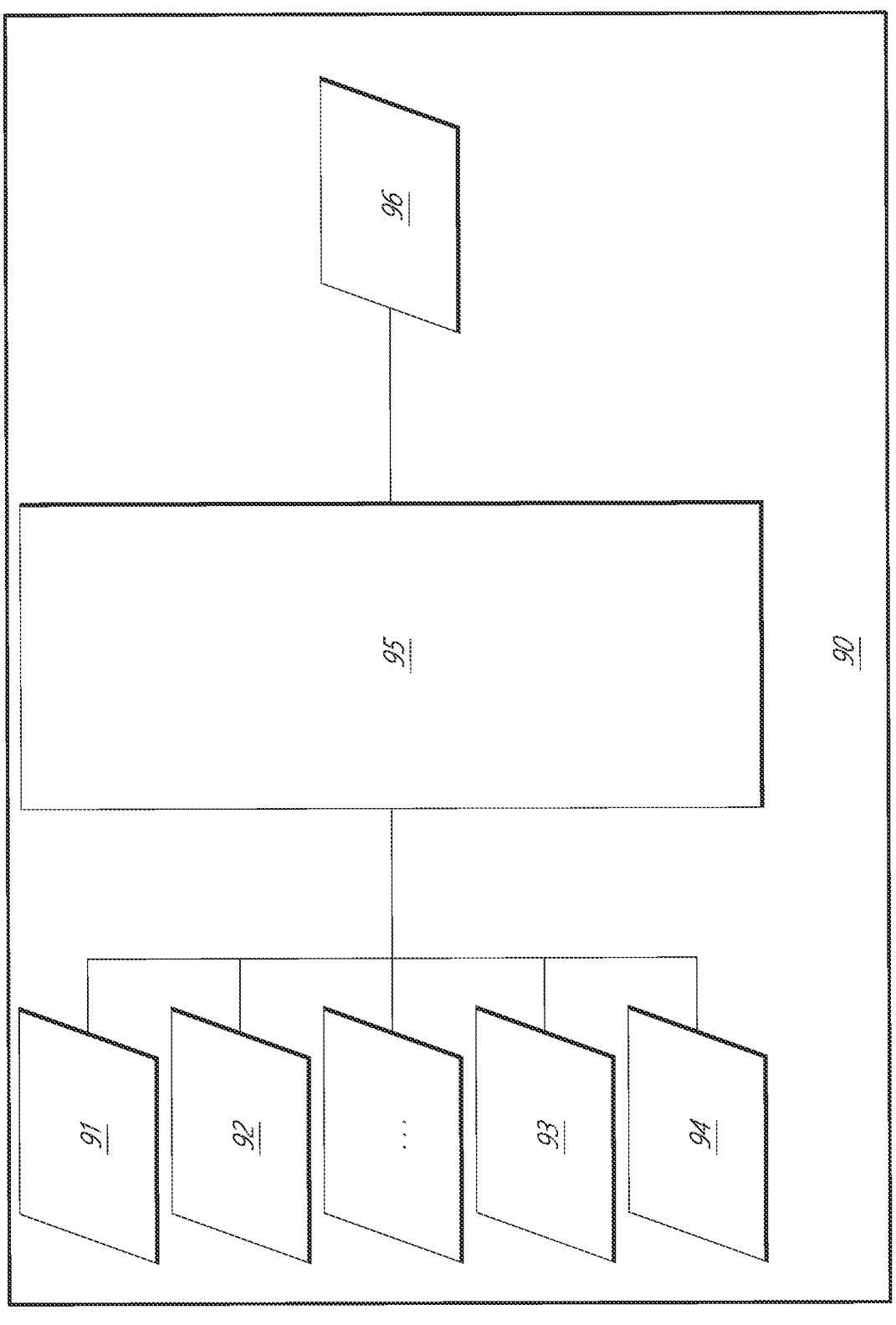
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Hand Manipulated Input Devices for Robotic Systems.

Embodiments of the disclosure relate to systems and techniques for input devices for operating robotic medical systems and/or one or more medical instruments with such robotic medical systems.

Robotic medical systems, such as the systems described above, can include an input device that is configured to allow an operator (e.g., a physician performing a robotically-enabled medical procedure) to manipulate and control one or more instruments. In some embodiments, the robotic medical system can include an input device for operating one or more medical tools. In some examples, the input device can operate one or more medical tools remotely, such as via teleoperation or telesurgery.

One skilled in the art will appreciate that the input devices described herein can be applied in non-medical contexts as well. For example, the input devices can be useful for manipulating tools that involve hazardous substances. In addition, in some embodiments, the input devices described herein can be useful in grabbing objects in both physical and virtual environments. In some configurations, the input devices can be self-sufficient as service robots interacting with human operators. In some configurations, the input device can be coupled (e.g., communicatively, electronically, electrically, wirelessly and/or mechanically) with a medical instrument such that manipulation of the input device causes a corresponding manipulation of the medical instrument. In some configurations, the input device and the medical instrument are arranged in a master-slave pair. In some configurations, the input device can be configured to control operation of a robotic surgical tool. In some configurations, the input device can be referred to as a manipulator, emulator, master, controller, interface, etc.

The input device can serve as an input for an operator to control the actions of a medical instrument, such as in an endoscopic, endoluminal, laparoscopic, or open surgery. Movement of the input device by the operator can direct the movement of the medical instrument. For example, when an operator translates the input device in three-dimensional space (e.g., up, down, left, right, backwards, forwards), the system can cause a corresponding translation of the medical instrument. Similarly, if the operator rotates the input device (e.g., around any of three orthogonal axes) the system can cause a corresponding rotational movement of the medical instrument. The input device can also include one or more inputs that allow the operator to actuate the medical instrument. As one example, if the medical instrument includes a grasper instrument, the input device can include one or more inputs that allow the operator to open and close the grasper instrument.

In some embodiments, robotic medical systems include input devices with seven degrees of freedom that follow the operator's hand movement, with the seven degrees of freedom including three positional degrees of freedom (e.g., translational movement in x, y, z space), three rotational degrees of freedom (e.g., rotational movement around pitch, roll, and yaw axes), and one (or more) instrument actuation degree of freedom (e.g., an angular degree of freedom). In some embodiments, the instrument actuation degree of freedom can control the opening and closing of an end effector of the medical instrument, such as a gripper or grasper instrument to hold an object. In some embodiments, input devices can include greater or fewer numbers of degrees of freedom. For example, in some embodiments, the input device can include more than three positional degrees of freedom or more than three rotational degrees of freedom to provide one or more redundant degrees of freedom. In some embodiments, redundant degrees of freedom can provide additional mechanical flexibility for the input device, for example, to avoid singularities caused by the mechanical structure of the input device.

FIG. 19 shows an embodiment of an input device or controller 182 that can be used by a user to control one or more instruments. As noted above, the controller can include two handles 184 that can be used to control instrumentation. Each of the handles 184 can be connected to a gimbal 186. Both of the handles 184 can serve as a grasper.

The grasper can be the portion of the input device that the operator (e.g., a physician, a user, etc.) touches and holds to allow the operator to control the components of the robotic system, such as the medical instruments. The grasper can be the operator's primary input into the system during surgery.

A. Multi-Link Grasper

Figure 21A:
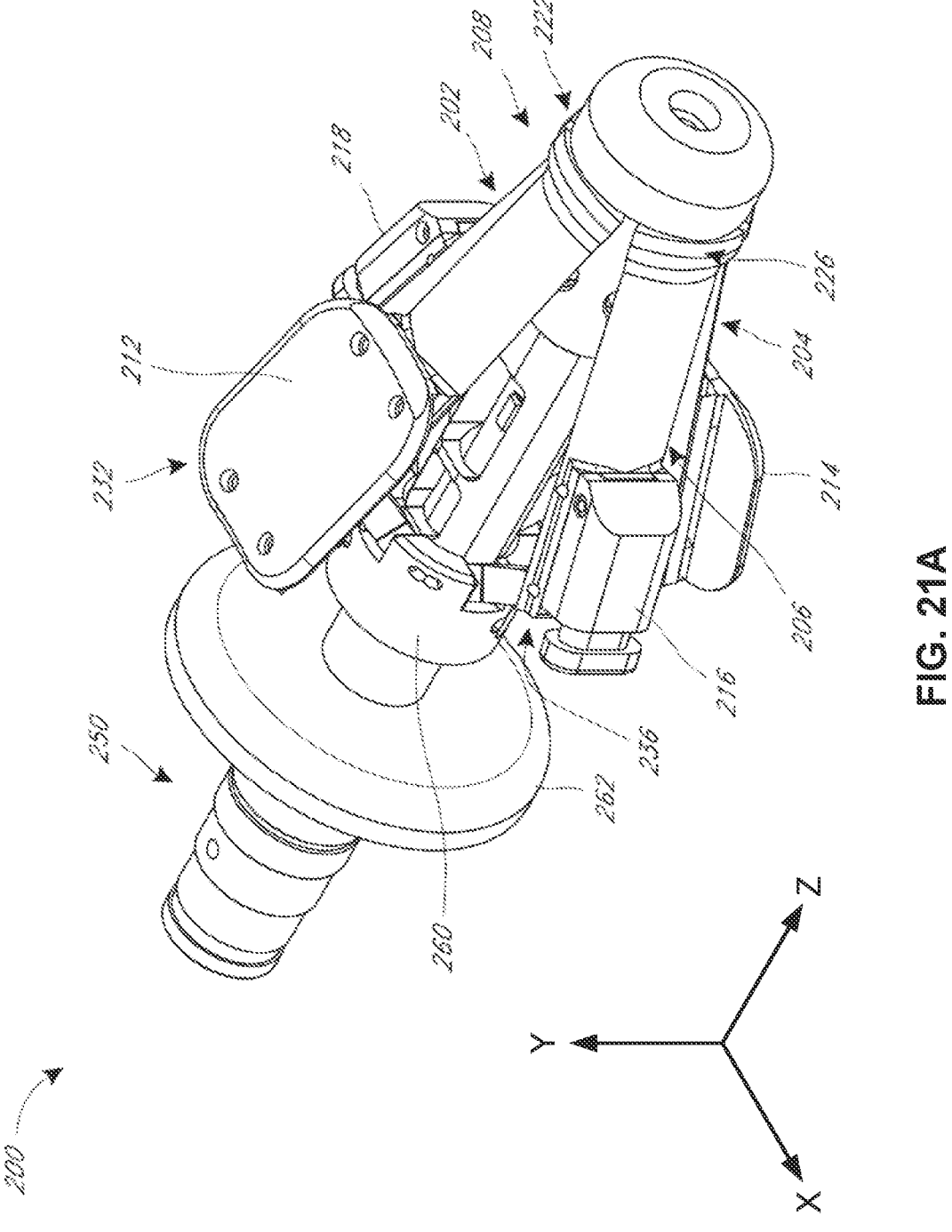
FIG. 21A illustrates an input device in an open position in accordance with some embodiments.
Figure 21B:
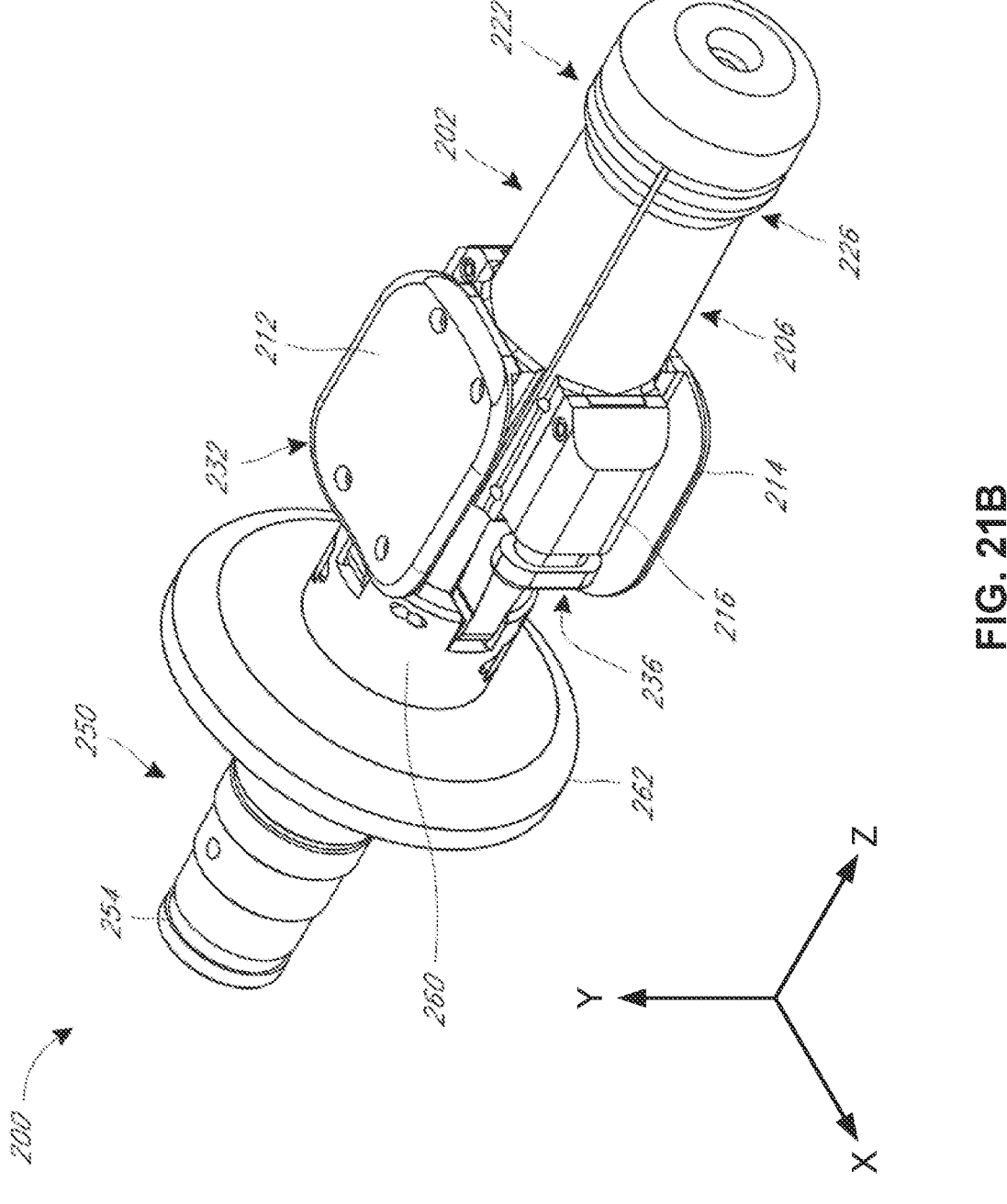
FIG. 21B illustrates the input device of FIG. 21A in a closed position in accordance with some embodiments.
Figure 22:
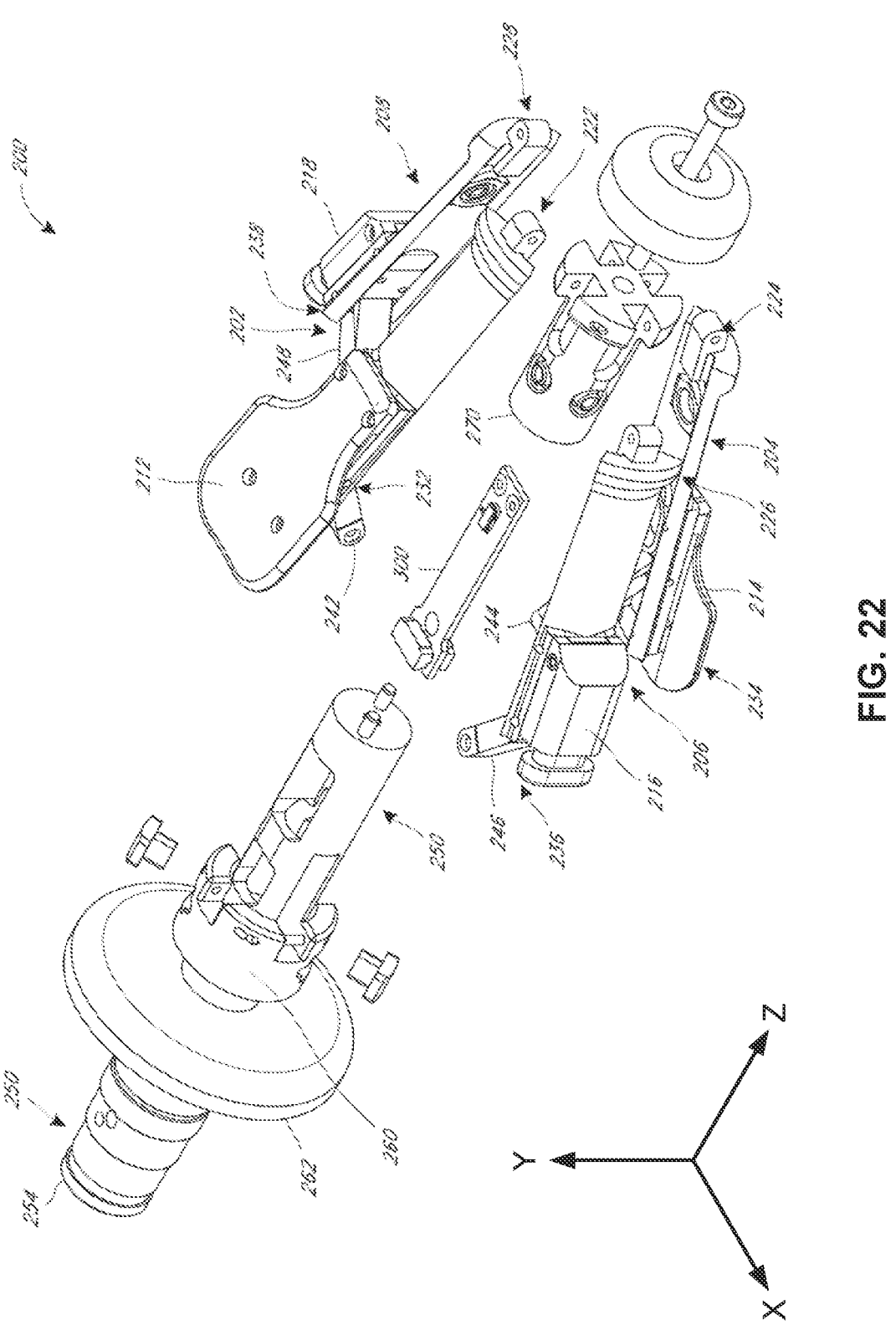
FIG. 22 illustrates the input device of FIGS. 21A-21B in an exploded view in accordance with some embodiments.

FIGS. 21A-21B illustrate an embodiment of a handle or grasper 200 that can be used as part of a input system such as the input system described above with reference to FIG. 19. FIG. 21A illustrates the grasper 200 in an open configuration, while FIG. 21B illustrates the grasper 200 in a closed configuration. FIG. 22 illustrates the grasper of FIGS. 21A-21B in an exploded view. The grasper 200 can include a plurality of links and in the illustrated embodiment the grasper 200 includes four links 202, 204, 206, 208. In some configurations, the grasper can include at least two links. In some configurations, the grasper 200 can include at least three links. In some examples, the grasper 200 can have any number of links, such as anywhere between 2-12 links. In some embodiments, the plurality of links can be arranged circumferentially around the grasper 200. In some configurations, the plurality of links can be equally spaced from one another. In some configurations, the plurality of links can be spaced less than 180 degrees from one another about a central axis. Although the configurations described below include four links, any number of links can be included.

As illustrated in FIGS. 21A-21B, the grasper 200 includes four links comprising a first link 202, a second link 204, a third link 206, and a fourth link 208. The four links 202, 204, 206, 208 can be spaced about the circumference of the grasper 200. The four links 202, 204, 206, 208 can be spaced evenly from each other. The four links can be arranged radially symmetrically. In some embodiments, the four links 202, 204, 206, 208 can each be spaced less than 180 degrees from the adjacent links. The four links 202, 204, 206, 208 may be each spaced approximately 90 degrees from one another as shown in the illustrated arrangement. The plurality of links 202, 204, 206, 208 can be arranged circumferentially about the grasper 200 as illustrated.

The links 202, 204, 206, 208 can be arranged in pairs. For example, the grasper 200 can include a first pair of opposing links 202, 204 and a second pair of opposing links 206, 208. In the illustrated arrangement, the first pair of opposing links can include the first link 202 and the second link 204 spaced approximately 180 degrees from one another. In the illustrated arrangement, the second pair of opposing links can include the third link 206 and the fourth link 208 spaced approximately 180 degrees from one another. In modified arrangements, the links 202, 204 of the first pair of opposing links can be spaced less than 180 degrees from each the links 206, 208 of the second pair of opposing links.

With reference to FIG. 22, the grasper 200 can include a central shaft 250. The central shaft 250 can be called a longitudinal shaft, longitudinal member, central member, shaft, or member. The central shaft can include a circuit 300, such as a printed circuit board, to connect to other components of the grasper 200 or other components of the robotic system. In the illustrated arrangement, the circuit 300 can be placed inside the central shaft 250.

The central shaft 250 can support the plurality of links 202, 204, 206, 208. Each of the first pair of opposing links 202, 204 and each of the second pair of opposing links 206, 208 can be coupled to the central shaft 250. The first link 202 can have a proximal end 232 and a distal end 222. The second link 204 can have a proximal end 234 and a distal end 224. The third link 206 can have a proximal end 236 and a distal end 226. The fourth link 208 can have a proximal end 238 and a distal end 228. The plurality of links 202, 204, 206, 208 can be connected or operatively connected at their respective proximal ends 232, 234, 236, 238 and/or at their respective distal ends 222, 224, 226, 228.

The first pair of opposing links 202, 204 can each include a finger grip or pad 212, 214. The second pair of opposing links 206, 208 can each include a secondary input 216, 218. Each of the plurality of links 202, 204, 206, 208, can include a secondary link 242, 244, 246, 248 to attach the proximal ends 232, 234, 236, 238 of the links 202, 204, 206, 208 to the central shaft 250.

Each of the plurality of links can be configured to move from an open position where proximal ends 232, 234, 236, 238 of each of the plurality of links 202, 204, 206, 208 are positioned radially away from the central shaft 250 to a closed position where the proximal ends 232, 234, 236, 238 of each of the plurality of links 202, 204, 206, 208 are positioned radially close to the central shaft 250. With reference again to FIG. 21A, the grasper 200 is shown in an open position with the proximal ends 232, 234, 236, 238 of the plurality of links 202, 204, 206, 208 positioned away from the central shaft 250 of the grasper 200. Each of the plurality of links 202, 204, 206, 208 can be connected to the grasper 200 at each of its respective distal ends 222, 224, 226, 228, such that each link can extend or pivot at an angle away from a central shaft 250. The proximal ends 232, 234, 236, 238 of each of the first pair of opposing links 202, 204 and each of the second pair of opposing links 206, 208 are configured to radially move relative to the central shaft 250.

With reference again to FIG. 21B, the grasper 200 is shown in a closed position with the proximal ends 232, 234, 236, 238 of the plurality of links 202, 204, 206, 208 positioned close to the central shaft 250 of the grasper 200. In the closed position, each of the proximal ends 232, 234, 236, 238 can be positioned close to the central shaft 250, such that the each of plurality of links 202, 204, 206, 208 can be parallel in length to the central shaft 250.

Each of the plurality of links 202, 204, 206, 208 can be biased in an open position. In some configurations, each link can be spring-loaded in an open position. In some configurations, there are at least two springs (not shown) for each link with a first spring providing the majority of the force to bias the link in an open position. A second spring can provide a slight haptic feedback when the link reaches a certain degree of closure to indicates to the user when the grasper is closed and that further motion to close the grasper will result in an increase of clamping force of the surgical instrument.

For example, the first pair of opposing links 202, 204 and/or the second pair of opposing links 206, 208 can be maneuvered in a pinching motion, which can be translated to movement of the surgical instrument inside the body. For example, opening and closing the first pair of opposing links 202, 204 would correspond to opening and closing of a scissor tool or jaws of a medical instrument. The facilitated pinching motion can make grasper actuation natural and easy for the user.

The plurality of links 202, 204, 206, 208 on the grasper 200 can measure the input angle of the user's fingers. For example, the angle at which any one or more of the plurality of links 202, 204, 206, 208 are positioned relative to the central shaft 250 can be translated to the desired angle of a component of the instrument, such as one or more jaws of an end effector of the instrument.

The grasper 200 can have an increased number of links (such as four links as shown in FIGS. 21A-21B and 22) and/or links that are positioned closer to each other. The grasper 200 can also be radially symmetrical, in particular at the most distal end.

By having such a radially symmetric configuration of the grasper, a user can advantageously be capable of performing certain movements with ease (e.g., a roll maneuver) that would otherwise be challenging. If a user wants to do a roll-intensive task (e.g., suturing) with a grasper unlike those described herein, the user can only rotate the grasper approximately 180 degrees before their wrist runs out of range of motion without repositioning the user's hand. To continue rolling the grasper, they have to release their current position of the grasper, rotate their wrist and regrip the grasper to continue.

The radially symmetric grasper with the plurality of links spaced less than 180 degrees from each other allows the physician to roll the grasper between their finger-tips while maintaining the desired orientation of the grasper (such as in the closed position or in maintaining the closure angle). This is possible since the user's fingers always make contact with at least two links because of the increased number of plurality of links and reduction of the dead zones that can exist between the plurality of links.

Some users may choose to work outside of the finger pads 212, 214, to hold the plurality of links 202, 204, 206, 208 closer to their distal ends 222, 224, 226, 228 of the plurality of links 202, 24, 206, 208. The grasper 200 advantageously is able to accommodate this and allow for comfortable use both in and out of the finger pads 212, 214. Additionally, when working outside of the finger pads 212, 214 (such as at the distal ends 222, 224, 226, 228 of one or more of the plurality of links 202, 204, 206, 208), the grasper 200 can have radial symmetry, such that the physician can close the grasper 200 (such as closing the first pair of opposing links 202, 204 and/or closing the second pair of opposing links 206, 208) and then roll the grasper 200 between their fingers. When executing this roll maneuver of the grasper 200, it can be desirable to have the grasper 200 remain in the closed position. The first pair of opposing links 202, 204 and/or the second pair of opposing links 206, 208 can be identical and symmetrical at their distal ends 222, 224, 226, 228, allowing the user to use any of the plurality of links 202, 204, 206, 208 to close the grasper 200.

The radial symmetry at the distal end can advantageously be more forgiving of misalignment of the user's hand when operating the grasper 200. Furthermore, the increased number of links being spaced closely together (such as, less than 180 degrees from one another) allows the user to more easily position their fingers to maintain contact with one or more of the plurality of links as they maneuver the grasper 200. For example, when working outside the finger pads 212, 214, the user can use any combination of the plurality of links to actuate the grasper 200. The plurality of links can increase the number of points of contacts for a user to actuate the grasper 200. This can allow the user to maintain contact with the actuators of the grasper more easily, to decrease difficultly of positioning and readjusting of the user's hand. The plurality of links and radial symmetry can give a user more freedom to manipulate the grasper 200.

The first pair of opposing links 202, 204 can be longer in length than the second pair of opposing links 206, 208. The plurality of links can be arranged such that the longer links 202, 204 oppose each other, with the shorter links 206, 208 located between the two. The two longer links 202, 204 can serve as the main grasping links. The longer links 202, 204 can have finger grips, pads, loops such as the finger pads 212, 214 of the illustrated arrangement.

In other examples, the first pair of opposing links 202, 204 and the second pair of opposing links 206, 208 can be of equal length. In other examples, the second pair of opposing links 206, 208 can be longer in length than the first pair of opposing links 202, 204.

Figure 23:
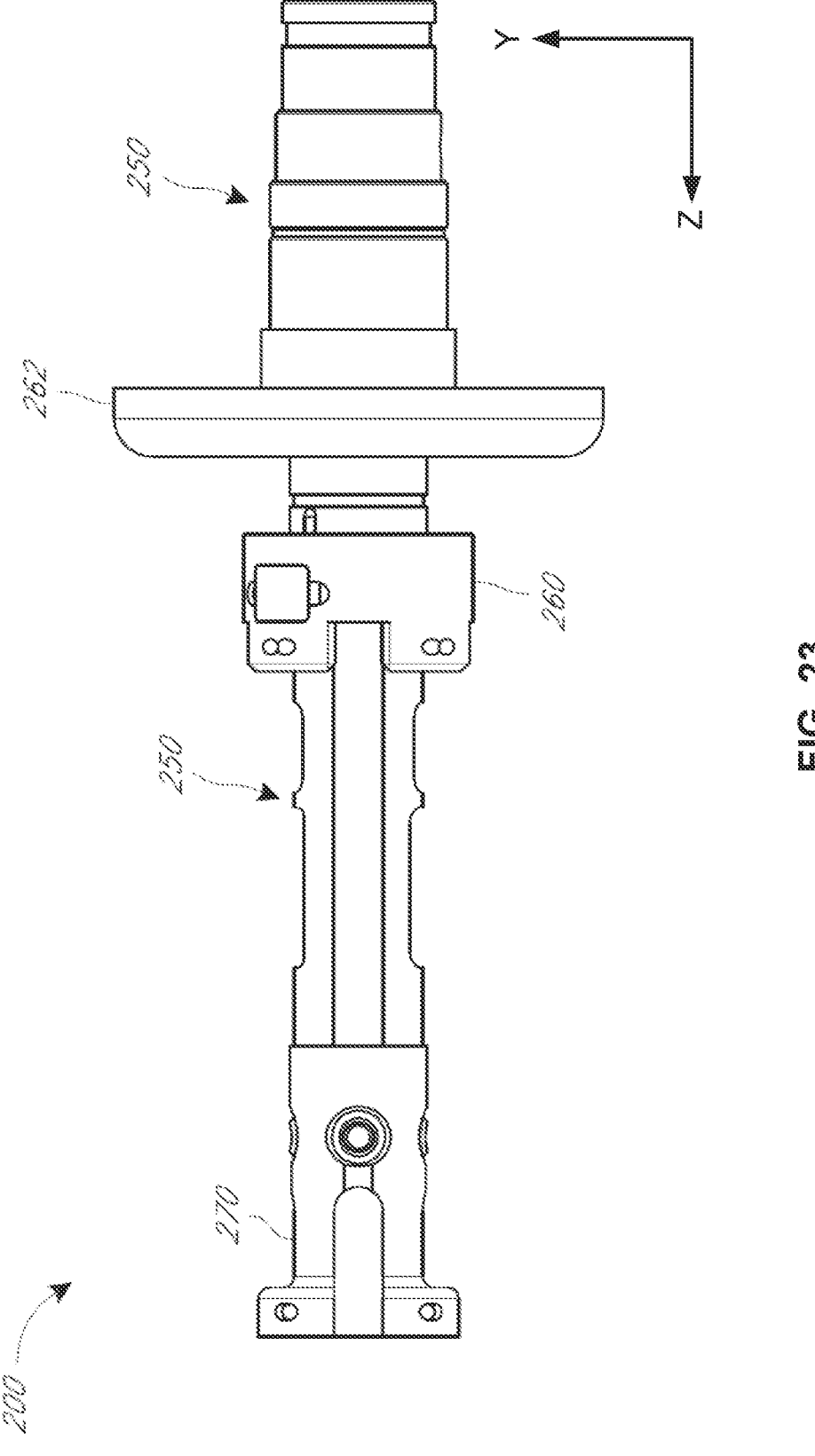
FIG. 23 illustrates the input device of FIGS. 21A-21B and 22 without a plurality of links in accordance with some embodiments.
Figure 24A:
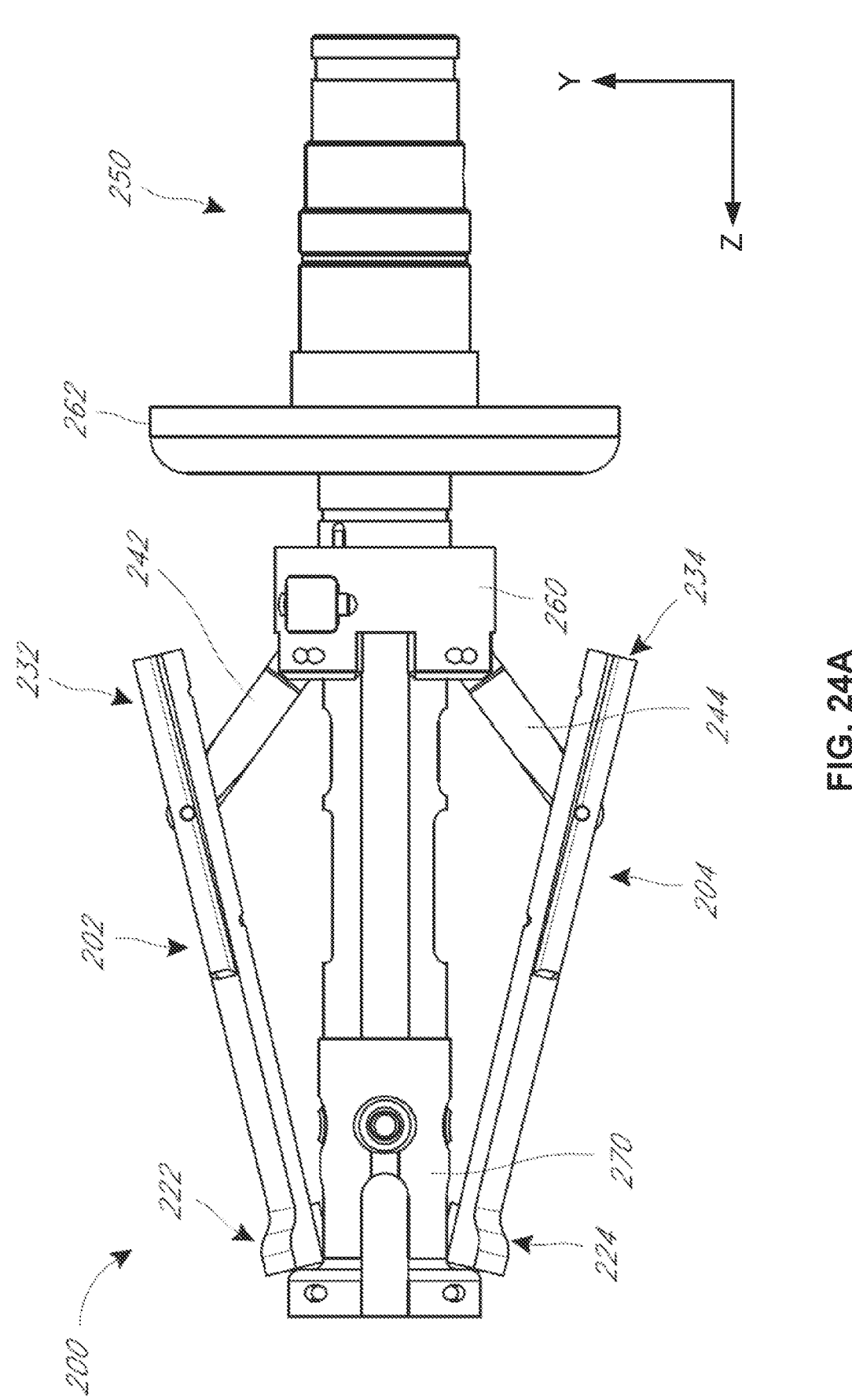
FIG. 24A illustrates the input device of FIGS. 21A-21B and 22-23 without a second pair of links in an open position in accordance with some embodiments.

FIG. 23 illustrates the grasper of FIGS. 21A-21B and 22 without the plurality of links, to show the central support shaft 250 and a sliding support 260 in more detail. The main support shaft 250 can serve as a bearing surface for the sliding support 260. The slide or a sliding support 260 can be connect to the plurality of links 202, 204, 206, 208 as shown in FIG. 24A. The main support shaft 250 can engage with or connect to the sliding support 260 to constrain of links 202, 204, 206, 208 relative to the central support shaft 250 while still allowing translation of the rotation of the plurality of links 202, 204, 206, 208 relative to the central support shaft 250. For example, the central support shaft 250 can have slots or recesses to receive portions of the sliding support 260 or receive keys that connect to the sliding support 260. Additionally, the keys can serve as stops to limit the translation of the sliding support 260. In some examples, the limit of translation can be approximately 5 mm.

Figure 24B:
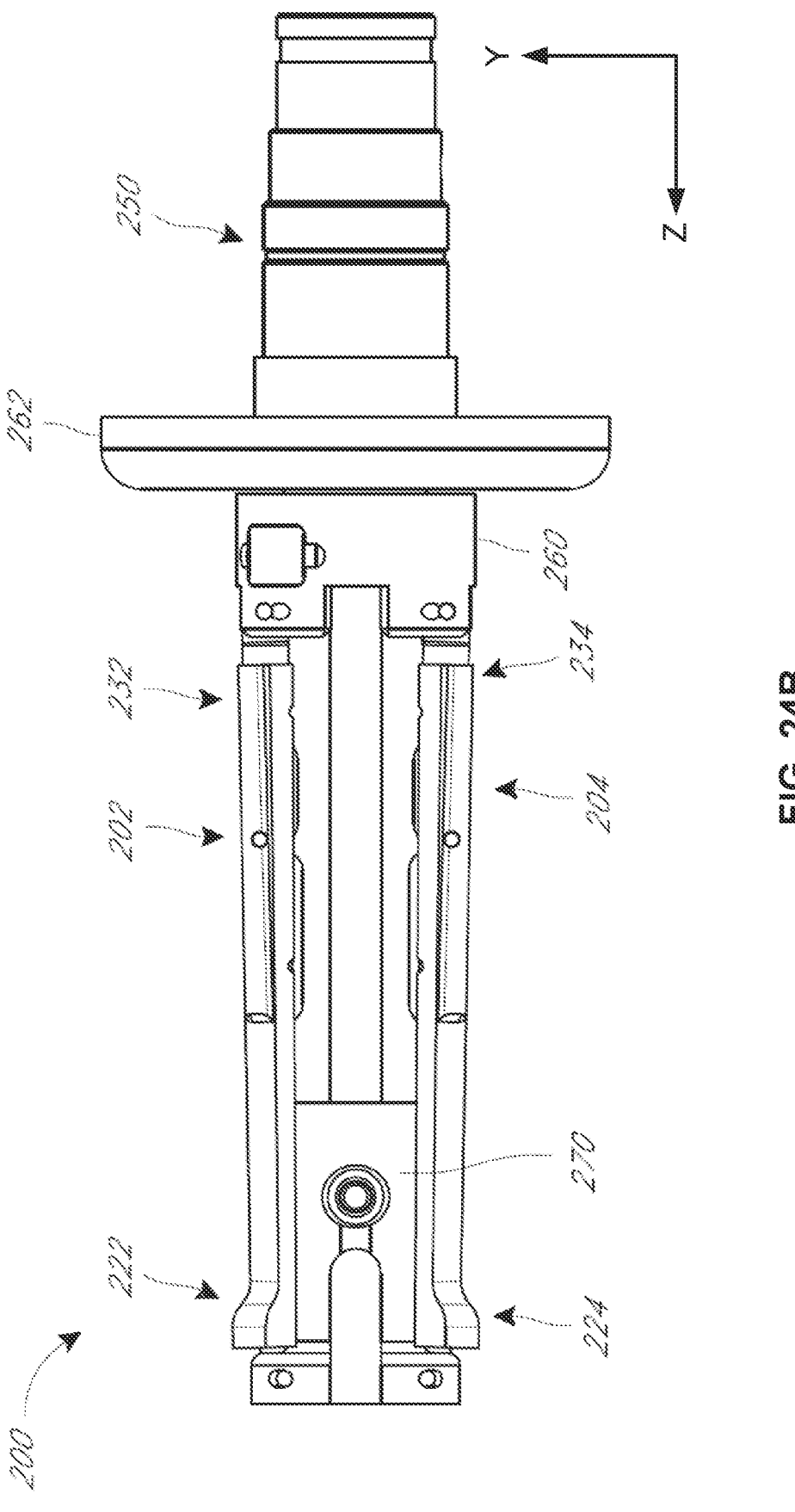
FIG. 24B illustrates the input device of FIG. 24A in a closed position in accordance with some embodiments.

FIGS. 24A and 24B illustrate the grasper without the second pair of links 206, 208 for clarity. FIG. 24A illustrates the grasper with the first pair of links 202, 204 in the open position. FIG. 24B illustrates the grasper with the first pair of links 202, 204 in the closed position. As illustrated, the first pair of links 202, 204 can be connected at their respective proximal ends 232, 234 to the sliding support 260. For example, each of the plurality of links 202, 204, 206, 208 can be connected to the sliding support 260 with secondary links 242, 244, respectively. The secondary links 242, 244, can be free to pivot to change an angular displacement of the respective link 202, 204 into an axial translation of the sliding support 260 along the central shaft 250. In the open position as shown in FIG. 24A, the sliding support 260 can be positioned towards the proximal end of the grasper 200, such that the secondary links 242, 246 and the first pair of links 202, 204 are each angled away from the central shaft 250. As the sliding support 260 is moved in a distal direction, the secondary links 242, 244 are angled farther away from the central shaft 250, which in turn moves the proximal ends 232, 234, 236, 238 away from the central shaft 250. In the closed position as shown in FIG. 24B, the sliding support 260 can be positioned more proximally along the central shaft 250, such that the first pair of links 202, 204 and the secondary links 242, 248 are extended and angularly positioned closer to the central shaft 250. In the open position, the sliding support 260 can be positioned such that the first pair of links 202, 204 and/or the secondary links 242, 244 are fully extended in length and substantially parallel to the central support 250. In this configuration, axial displacement in one of the links 202, 204 causes the same displacement in the other link 202, 204. In this configuration, the motion of the first pair of links 202, 204 are constrained together. Each of the first pair of opposing links 202, 204 can be configured to move together, such that proximal ends 232, 234 of the first pair of opposing links 202, 204 are positioned equally distant from the central shaft 250.

In some of the configurations, the first pair of opposing links 202, 204 are configured to move together. In some configurations, the second pair of opposing links 206, 208 are configured to move together. In some of the configurations, the first pair of opposing links 202, 204 and the second pair of opposing links 206, 208 are configured to move together. In some of the configurations, the first pair of opposing links 202, 204 and the second pair of opposing links 206, 208 are configured to move independently. In some configurations, each of the plurality of links is configured to move independently. In some configurations, each of the plurality of links is configured to move together.

Although not shown in FIG. 24A-24B for clarity, the second pair of links 206, 208 can similarly be connected at their respective proximal ends 236, 238 can be connected to the sliding support 260 with secondary links 246, 248, respectively. In the illustrated arrangement, all four links 202, 204, 206, 208 can be connected to the same sliding support 260. In this configuration, axial displacement in one of the plurality of links 202, 204, 206, 208 causes the same displacement in the remaining three of the plurality of links 202, 204, 206, 208. In this configuration, the motion of the plurality of links 202, 204, 206, 208 are constrained together.

The grasper 200 can include a proximal plate 262. The proximal plate 262 can be attached to or integral with the central support shaft 250. The proximal plate 262 can be positioned about the central support shaft 250 towards the proximal end of the central support shaft 250. The proximal plate 262 can act as a stop to limit axial translation of the sliding support 260. In some examples, the proximal plate 262 can be positioned to prevent the sliding support 260 from extending the plurality of links 202, 204, 206, 208 past the lengths of the plurality of links 202, 204, 206, 208 and/or the secondary links 242, 244, 246, 248. In some examples, the proximal plate 262 can also serve as an additional surface to support the user's hand.

The plurality of links 202, 204, 206, 208 can be connected or operatively connected at their respective distal ends 222, 224, 226, 228. For example, the plurality of links 202, 204, 206, 208 can be connected or operatively connected at their respective distal ends 222, 224, 226, 228 to the distal link support 270. The plurality of links 202, 204, 206, 208 can be connected or operatively connected at their respective proximal ends 232, 234, 236, 238.

Figures 25A, 25B:
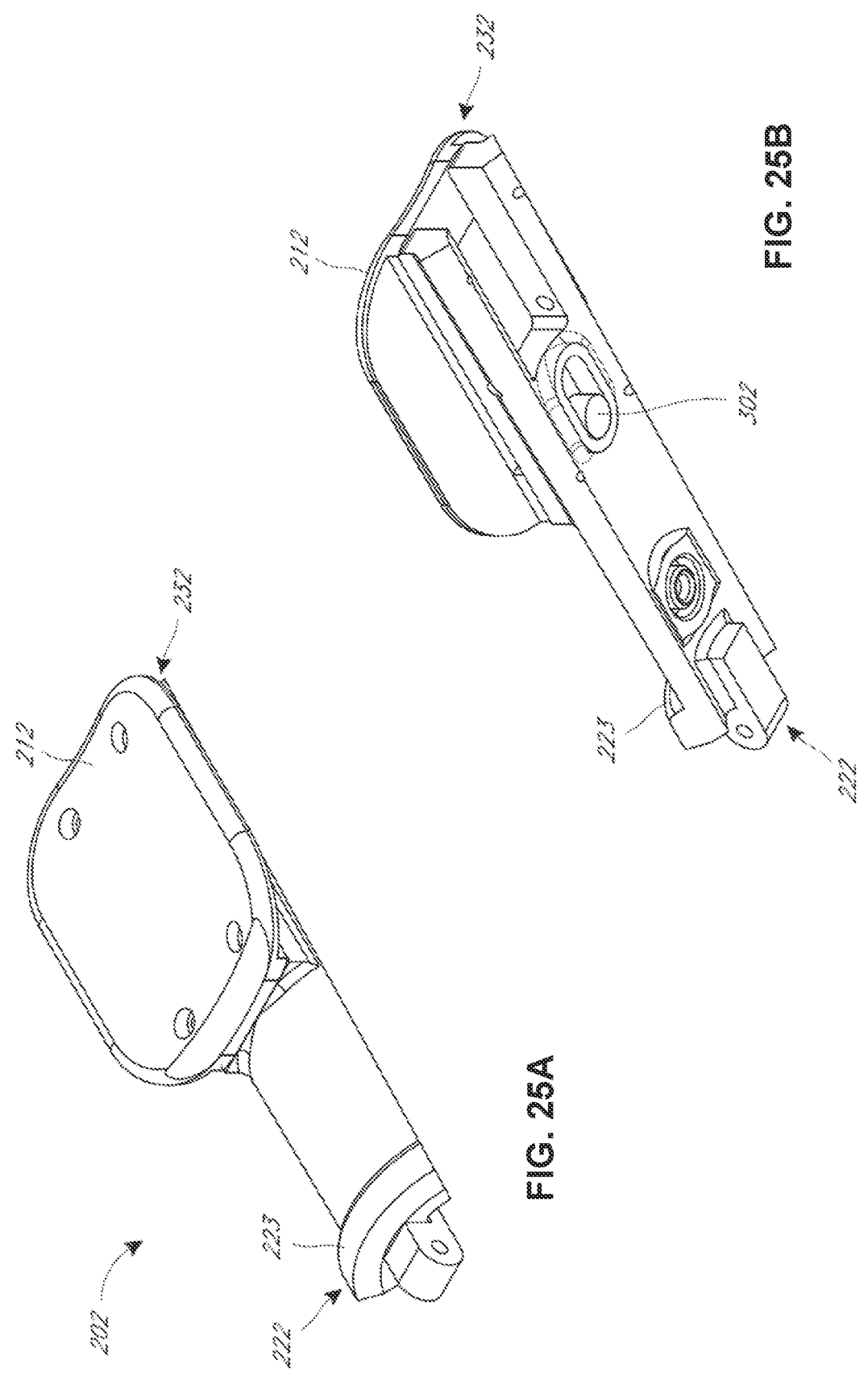
FIG. 25A illustrates a top view of a first link with a finger pad in accordance with some embodiments.
FIG. 25B illustrates a bottom view of the first link of FIG. 25A in accordance with some embodiments.
Figure 26:
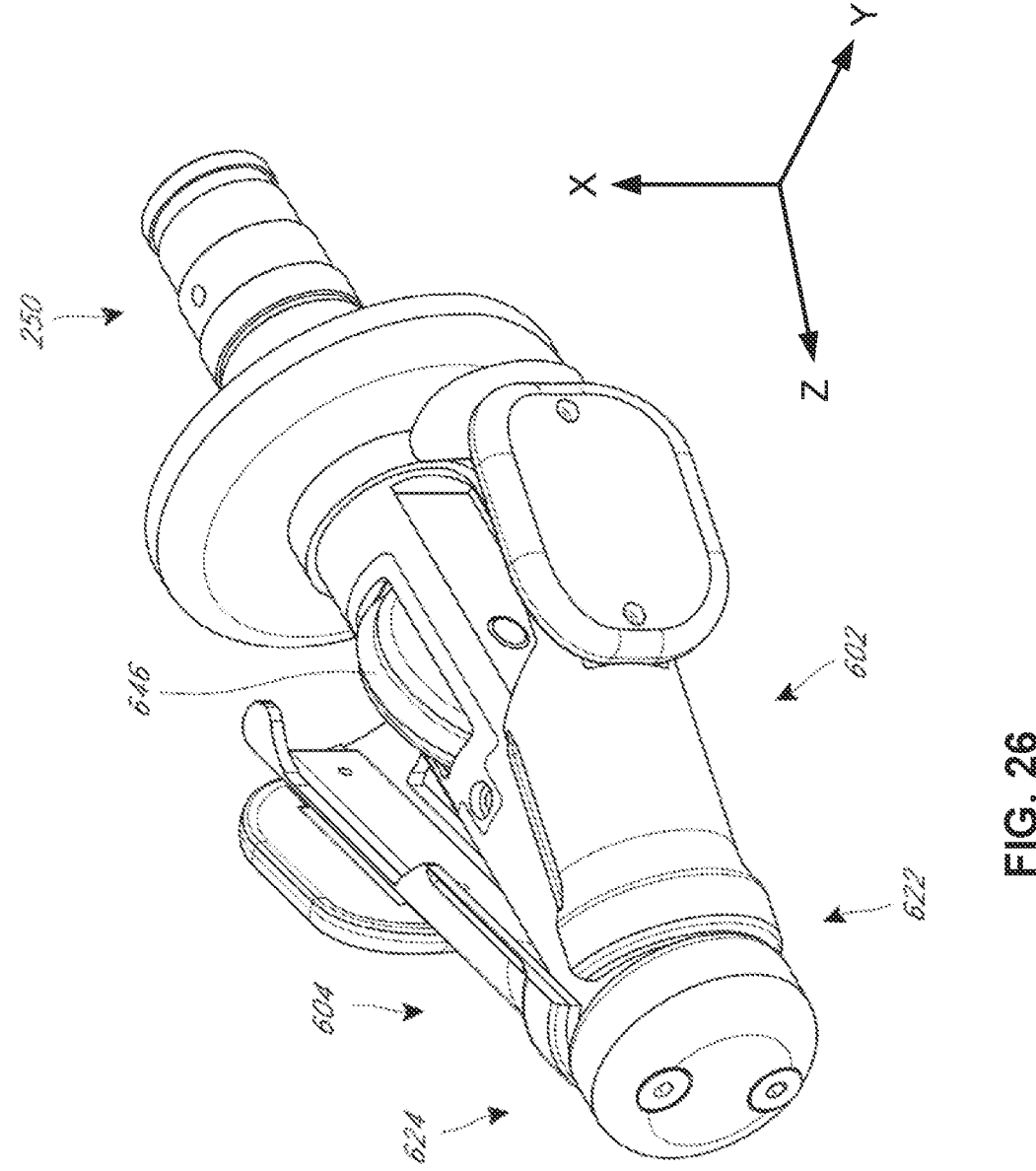
FIG. 26 illustrates yet another example of a third link with secondary input in accordance with some embodiments.
Figure 27:
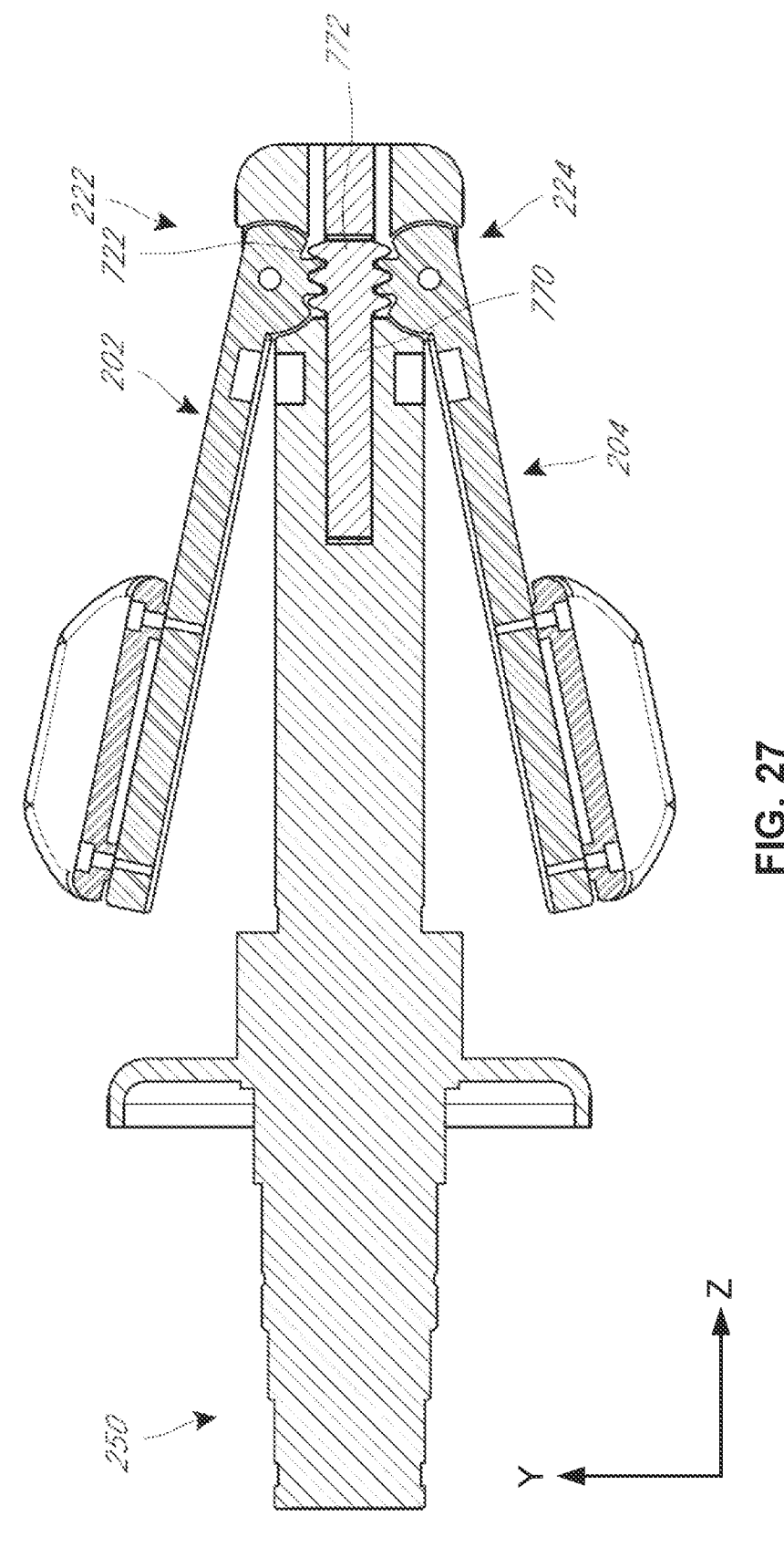
FIG. 27 illustrates another example of an input device in accordance with some embodiments.
Figure 28:
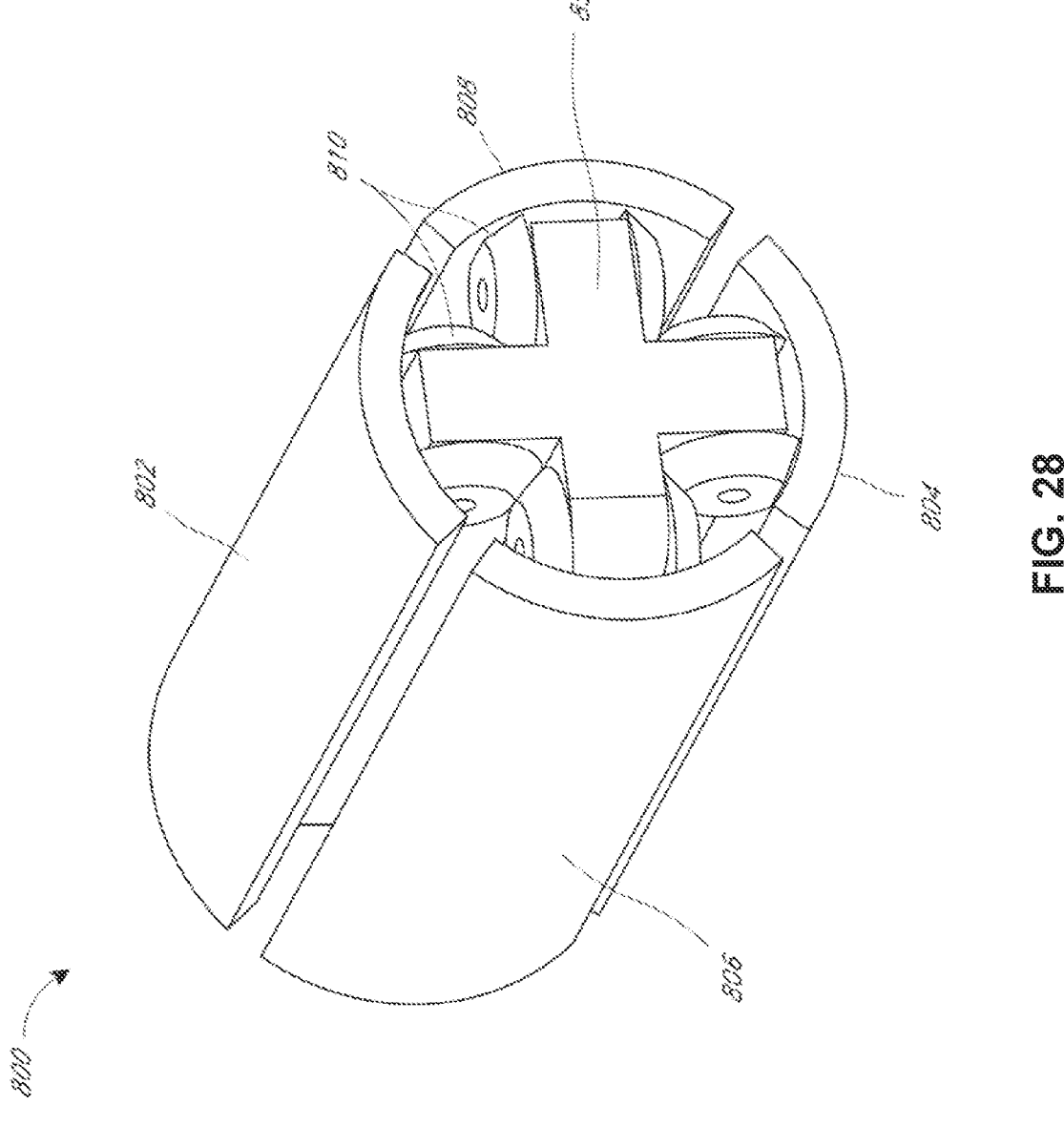
FIG. 28 illustrates a cross sectional view of another example of an input device in accordance with some embodiments.

FIG. 25A illustrates a top view of a first link 202 with a finger pad 212. FIG. 25B illustrates a bottom view of the first link 202 with the finger pad 212 of FIG. 25A. Although only the first link 202 of the first pair of links 202, 204 is shown in FIGS. 25A-25B, the second link 204 and figure pad 214 can be substantially similar. The first pair of opposing links 202, 204 can each include a finger pad 212, 214, respectively. The finger pads 212, 214 can facilitate manipulation of the finger links 202, 204 by increasing the surface area by which the user can contact and maneuver the opposing links. The finger pads 212, 214 can be attached to the respective links 202, 204 by bolts. A Velcro loop (not shown) can be positioned between the finger pads 212, 214 and the respective links 202, 204 to secure around a user's finger when in use.

The first pair of links 202, 204 can each include a distal ridge 223, 243 located at the distal ends 222, 224 of the first pair of links 202, 204, The distal ridges 223, 243 can each follow the contour of the respective link 202, 204. The distal ridges 223, 243 can be ergonomic features that allows the physician to easily grip and maneuver the grasper 200 at the distal end. For example, the distal ridges 223, 243 can act as a surface to enable a user to pull the grasper 200 towards them when working outside the finger pads 212, 214.

The first pair of links 202, 204 can each include a magnet 302, 304 used to sense the position of the respective pair of links 202, 204. As shown in FIG. 25B, a magnet 302 can be positioned or mounted on the bottom of the link 202. Angular displacements of the link 202 can be sensed by a hall effect sensor. The hall effect sensor can be positioned on or in the central shaft 250. The hall effect sensor can be used to measure the magnitude or changes in the magnetic field. As the plurality of links changes angles, the one or more sensors can be used to detect the change in magnetic field due to the motion of the magnets 302, 304, which occurs through motion of the respective links 202, 204. In some configurations, the hall effect sensor can be used to detect the distance of the magnet 302, 304 and thus the links 202, 204 with respect to the central shaft 250, which can be used by the input device to transmit control signals. Similarly, the second pair of links 206, 208 can also each include a magnet. Additionally, other sensors can be used, such as resistance sensors and/or optical sensors.

As described above, as the user maneuvers the plurality of links of the grasper, the user's fingers can adjust the angle of the plurality of links. The plurality of links can be oriented or angled relative to the central axis or central shaft. The plurality of links on the grasper can measure the input angle of the user's fingers. For example, the angle at which any one or more of the plurality of links are positioned relative to the central shaft can be translated to the desired angle of a component of the instrument, such as one or more jaws of an end effector of the instrument. The grasper 200 can include one or more sensors to measure the angle of the plurality of links and thus the input angle of the user's fingers. Also described above, the secondary input state can also be measured by one or more sensors.

The grasper can include one or more sensors in various locations. In some configurations, one or more sensors can be located in or coupled to one or more of the plurality of links. In some configurations, one or more sensors can be located in or coupled to the central shaft. The one or more sensors in the central shaft can be advantageous in that there is limited space on each of the plurality of links. The one or more sensors in the central shaft can also advantageously position the sensor away from motion of the links and from contact by the user, which can reduce risk of damaging the sensor.

In some configurations, the one or more sensors can include a hall effect sensor, such as a 3D hall effect sensor. The one or more sensors can include 3 different sensors in orthogonal orientations to each other. Using these sensor readings, an algorithm can be developed to determine both the angle of the plurality of links and detect a secondary input state. The position of the one or more sensors in the central shaft can also advantageously remove the need to run wires and package sensors on the links.

The one or more sensors can detect one or more magnets included in the plurality of link and/or one or more magnets in a secondary input. For example, each link can include one or more magnets in fixed locations. As the plurality of links changes angles, the one or more sensors can be used to detect the change in magnetic field due to the motion of these magnets.

Similarly, the secondary input can include or be operatively connected to one or more magnets, such that change or movement in the secondary input can change the position or orientation of the one or more magnets, which can be detected by the sensor. In some examples, the change of the magnetic field due to the secondary input can be coupled with the motion of the grasper or with one or more components of the grasper. In some examples, the angle of the plurality of links can be decoupled from the secondary input state.

In some configurations, the one or more sensors can be a 3 degrees-of-freedom sensor with physical electrical connections to the plurality of links and secondary inputs.

In some instances, the input device (e.g., the grasper) may not always be under the control of the operator. In addition, the input device may receive an input that is not intended by the user (e.g., unintended motion), which may be caused by the user or some other personnel in the operating room applying a disturbance to the input device or from gravity compensation errors (e.g., a user overcompensating for the gravity). In these instances, there may be a need to modify teleoperation and suppress or reduce movement of the robotic arms and its associated instruments. By detecting the unintended motion, the robotic system can respond to the user input to modify teleoperation and reduce, suppress, or stop movement of the robotic arms and associated instruments.

B. Capacitive Sensors

Figure 29A:
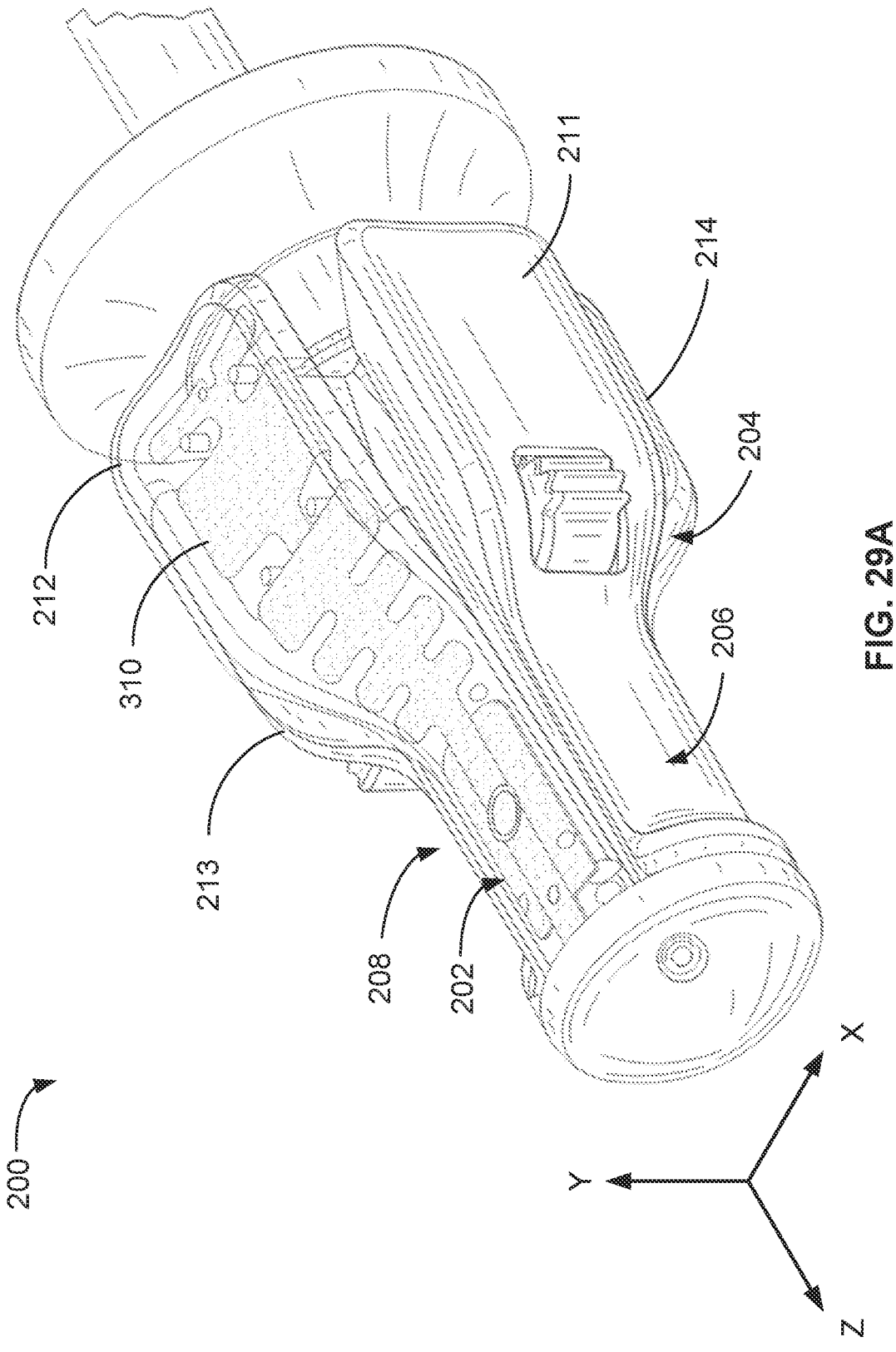
FIGS. 29A and 29B illustrate a sensor at the input device of FIG. 21A for sensing a user presence in accordance with some embodiments.
Figure 29B:
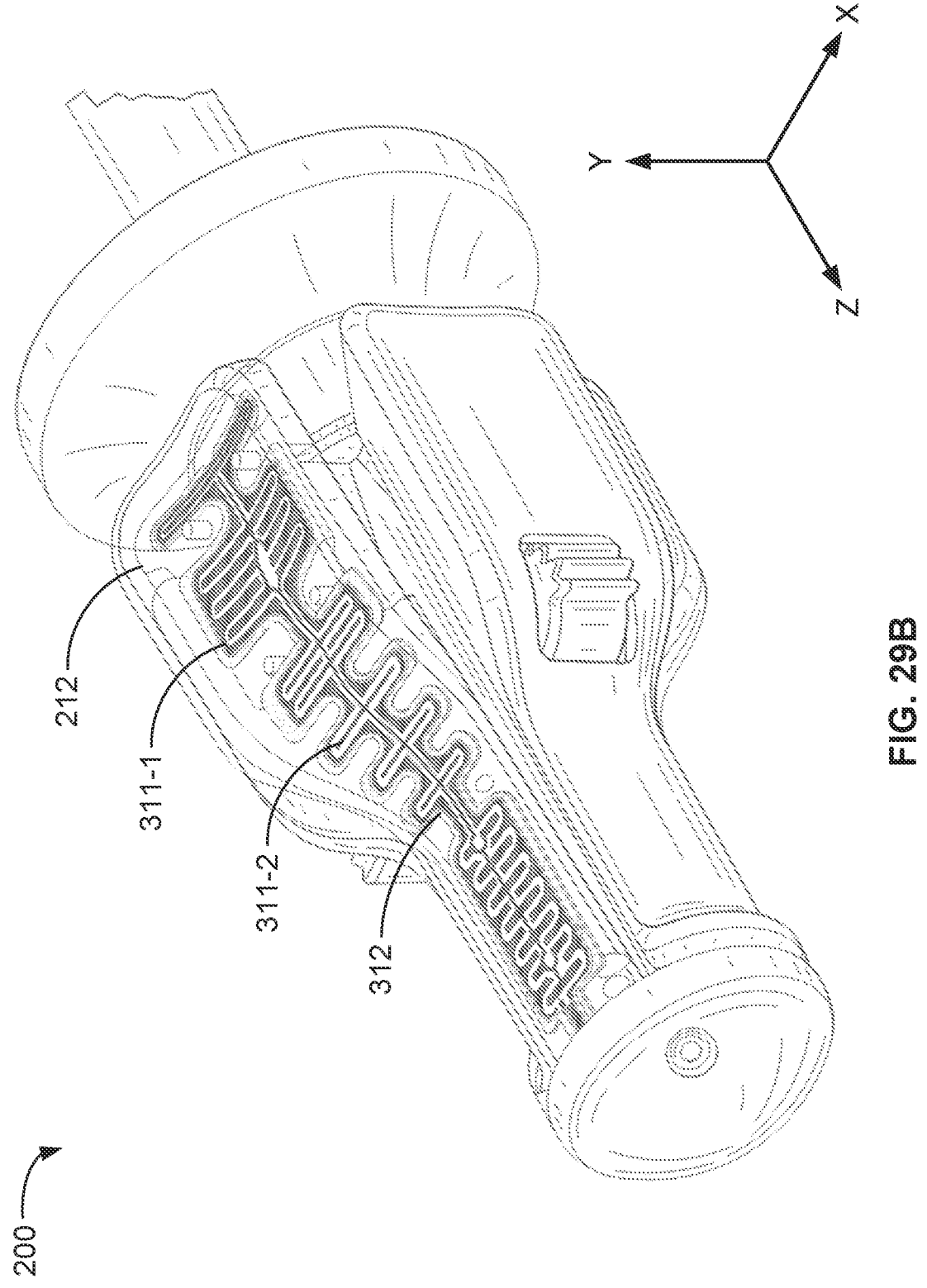

FIGS. 29A and 29B illustrate a sensor at the grasper 200 of FIG. 21A for sensing a user presence in accordance with some embodiments.

As shown in FIG. 29A, the grasper 200 includes one or more sensors 310 that are configured to generate a signal in response to a user being in proximity to the sensor. In some embodiments, a first sensor of the one or more sensors 310 is embedded in the finger pad 212. In some embodiments, the one or more sensors 310 include a second sensor that is embedded in the finger pad 214. In some embodiments, the grasper 200 also includes a finger pad 211 that is part of opposing link 206 and a finger pad 213 that is part of opposing link 208. The finger pad 213 may include a third sensor of the one or more sensors 310, and the finger pad 213 may include a fourth sensor of the one or more sensors 310.

In some embodiments, as shown in FIG. 29B, a sensor of the one or more sensors 310 includes one or more electrodes 311 (e.g., a metallic electrode and/or a conductive electrode). In some embodiments, the one or more electrodes 311 are connected to an integrated circuit (e.g., integrated circuit 328 shown in FIG. 34A). The integrated circuit is configured to measure a capacitance that changes when a user's body part (such as a user's hand, finger, or palm) is in proximity to the one or more electrodes. In some embodiments, the sensor includes the integrated circuit. In some embodiments, the integrated circuit is separate from the sensor (although the integrated circuit is electrically connected to the sensor).

Figure 30A:
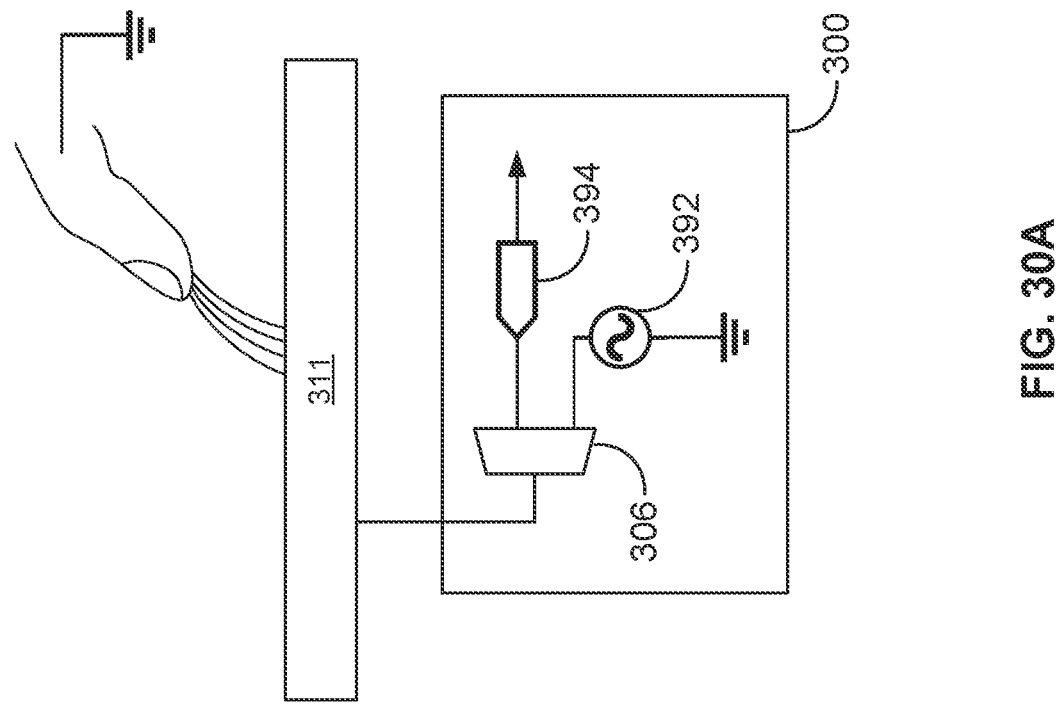
FIG. 30A illustrates measuring a self-capacitance of an electrode of the sensor shown in FIG. 29B in accordance with some embodiments.

In some embodiments, at least one sensor (e.g., sensor 310) of the one or more sensors 310 includes one electrode 311 (only), and the integrated circuit includes circuit 300 for measuring a self-capacitance of the electrode 311 (e.g., the capacitance between the electrode 311 and the earth), as shown in FIG. 30A. The self-capacitance changes when a user's body part is in proximity to the electrode 311. In some embodiments, the circuit 300 includes an excitation signal source 392 (e.g., an oscillator or an alternating current source) and an analog-to-digital converter 394 coupled to the (same) electrode 311 via a multiplexer 306.

Figures 30B, 30C:
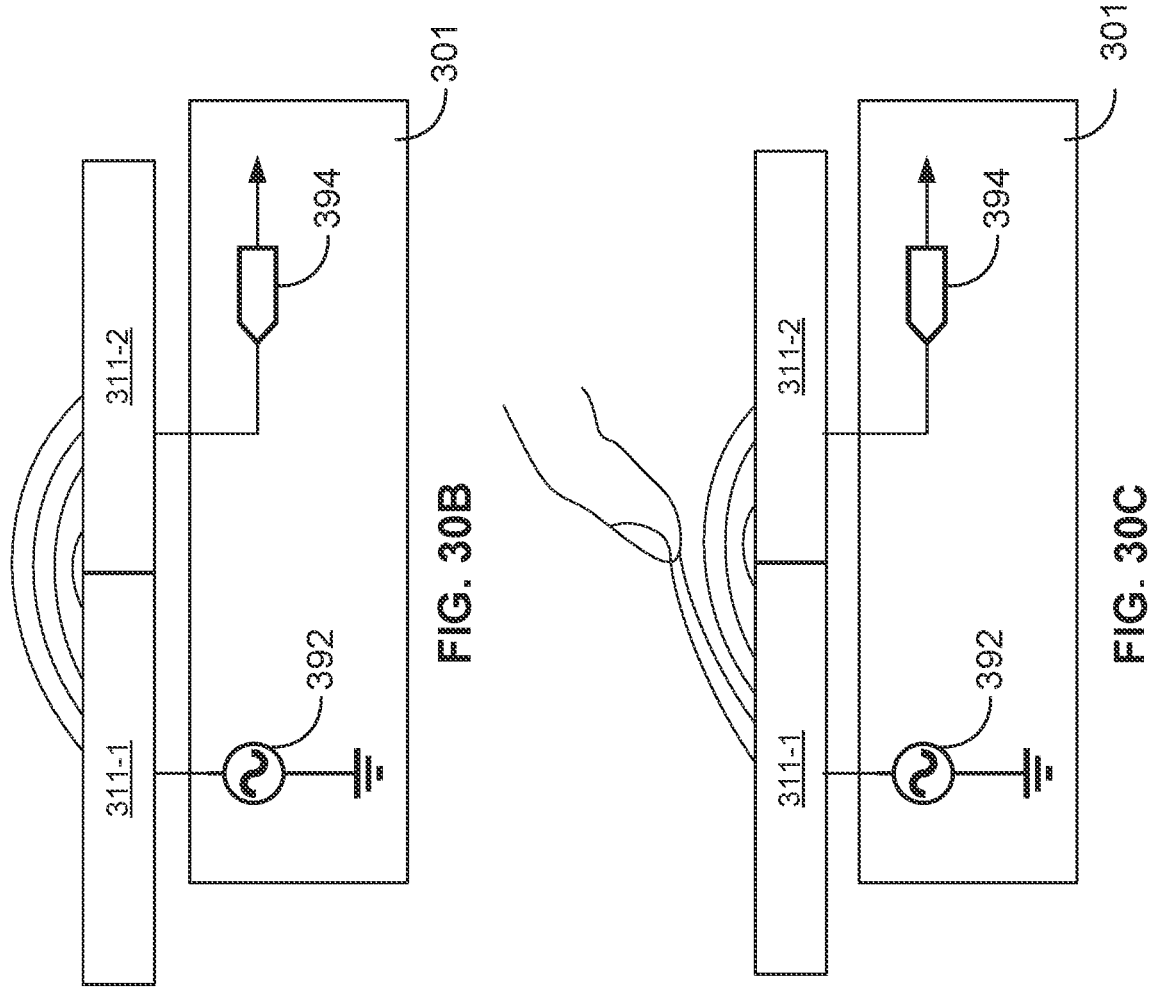
FIGS. 30B and 30C illustrate measuring capacitance between the electrodes of the sensor shown in FIG. 29B in accordance with some embodiments.

In some embodiments, at least one sensor (e.g., sensor 310) of the one or more sensors 310 includes two or more electrodes 311-1 and 311-2, and the integrated circuit includes circuit 301 for measuring a mutual-capacitance between the two electrodes 311-1 and 311-2, as illustrated in FIGS. 30B and 30C. As shown in FIGS. 30B and 30C, the mutual-capacitance changes when a user's body part is in proximity to the electrode 311-1 or 311-2, or between the two electrodes 311-1 and 311-2. In some embodiments, the circuit 301 includes the excitation signal source 392 (e.g., an oscillator or an alternating current source) coupled to a first electrode of the two or more electrodes (e.g., the electrode 311-1) and the analog-to-digital converter 394 coupled to a second electrode of the two or more electrodes (e.g., the electrode 311-2) that is distinct from the first electrode.

Figures 30D, 30E:
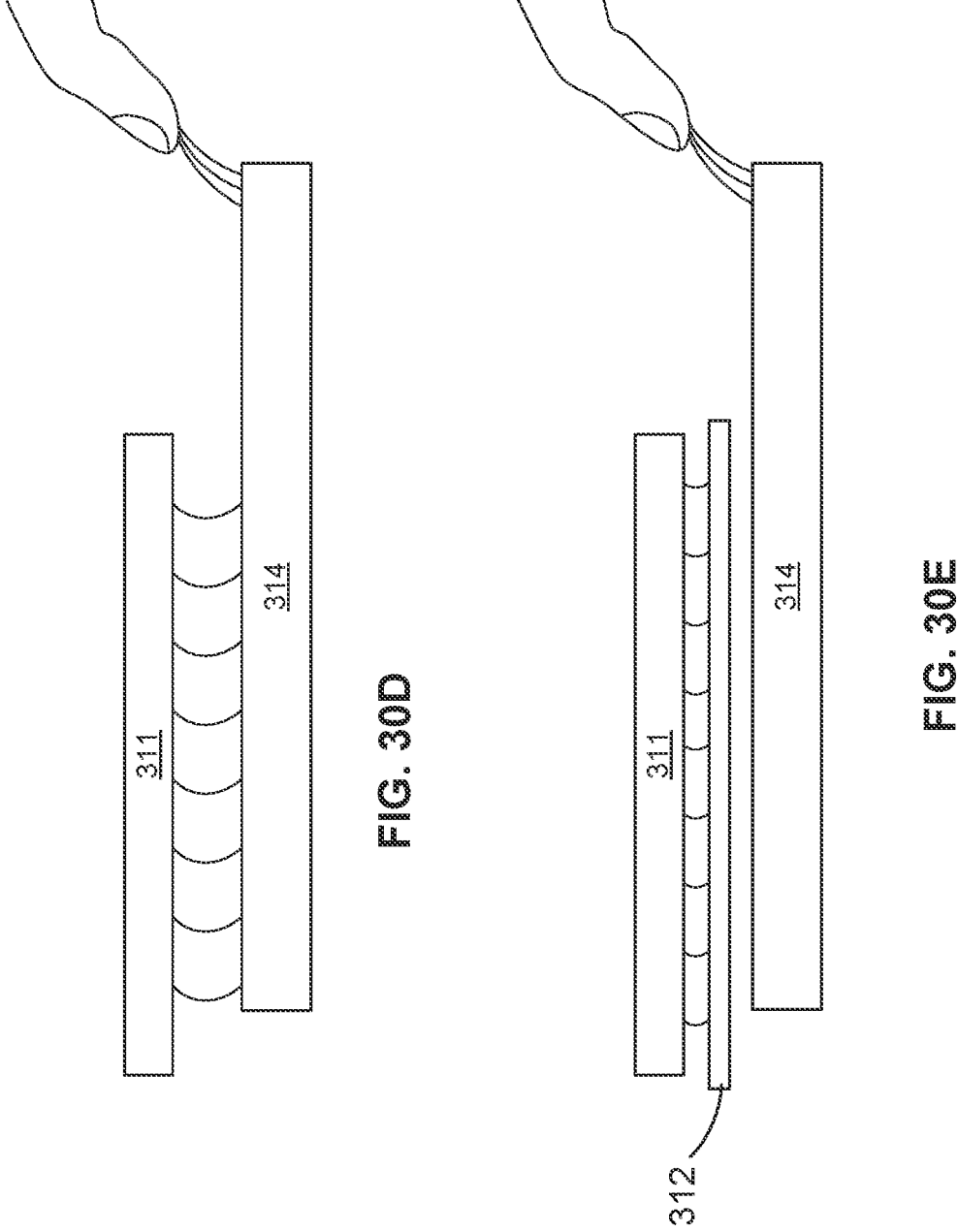
FIG. 30D illustrates cross-talk between the electrode shown in FIG. 30A with other components of the input device of FIG. 21A in accordance with some embodiments.
FIG. 30E illustrates a shield that reduces cross-talk between the electrode shown in FIG. 30A and other components of the input device of FIG. 21A in accordance with some embodiments.

FIG. 30D illustrates that, in some configurations, a sensor may detect a change in capacitance due to placement of a user's body part in proximity to components 314 (e.g., a metallic component) located adjacently to one or more electrodes 311 of the sensor. In addition, since the links 202, 204, 206, and 208 of grasper 200 are movable with respect to a central support 250 of the grasper 200, the distance between the one or more electrodes 311 of a sensor 310 and other components 314 of the grasper 200, such as the central support 250 and other components disposed on the central support, may change during operation of the grasper 200. Thus, even when the user's body part is not in proximity to the one or more electrodes 311, the capacitance can change, which can be interpreted incorrectly to indicate that the user's body part is in proximity to the one or more electrodes 311.

FIG. 30E illustrates that, in some embodiments, at least one sensor (e.g., sensor 310) of the one or more sensors 310 includes an electrode layer that includes the one or more electrodes 311, and a shield layer 312 for reducing capacitance between the one or more electrodes 311 and components 314 of the grasper 200. The shield layer 312 of the sensor 310 is disposed between the one or more electrodes 311 of the sensor 310 and other components 314 of the grasper 200. This reduces (and ideally, eliminates) changes in the measured capacitance due to a change in position of the one or more electrodes 311 of the sensor 310 relative to a position of the other components 314 of the grasper 200. Thus, the shield layer 312 reduces the effect that the other components 314 of the grasper 200 can have on the capacitance measured by the sensor with the one or more electrodes 311.

Figure 31:
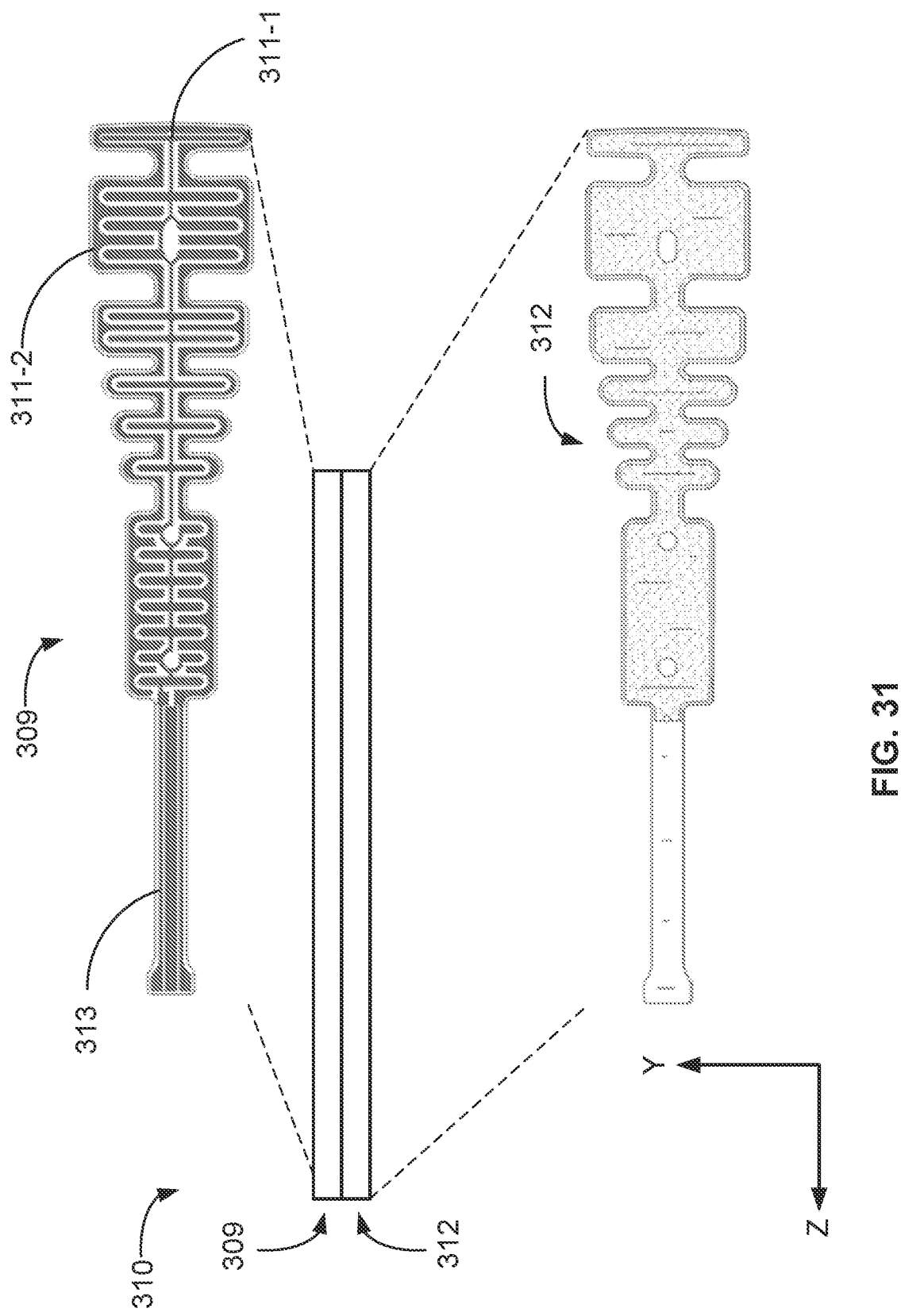
FIG. 31 illustrates an example of the sensor shown in FIGS. 29A and 29B that includes an electrode layer and a shield layer in accordance with some embodiments.

FIG. 31 illustrates an example of the sensor 310 shown in FIGS. 29A and 29B that includes an electrode layer 311 and a shield layer 312. In this example, the sensor 310 includes the electrode layer 309 and the shield layer 312. The electrode layer 309 includes a first electrode 311-1 that is surrounded by a second electrode 311-2. In some embodiments, the electrodes 311-1 and 311-2 are insulated from the shield layer 312 (e.g., the shield layer 312 may include a conductive material and the electrodes 311-1 and 311-2 are insulated from the shield layer 312 to reduce (and ideally, prevent or eliminate) any conductive effects between the electrodes 311 and the shield layer 312). In some embodiments, the sensor 310 is positioned in the grasper 200 with the shield layer 312 facing toward inward (e.g., toward the central support 250 of the grasper 200) and the electrode layer 309 facing outward (e.g., away from the central support 250 of the grasper 200).

In some embodiments, the sensor 310 includes an extension 313, which is used for electrically connecting the sensor 310 to an integrated circuit (e.g., the integrated circuit 328).

In some embodiments, the sensor 310 is made flexible (e.g., the sensor 310 is made of a flexible material). For example, the sensor 310 includes a multi-layer flex circuit. In some embodiments, the flex circuit is embedded in the finger pad (e.g., FIG. 29A). In some embodiments, the flex circuit is formed, molded, or machined into the finger pad. For example, in some embodiments, the flex circuit is injection molded in the finger pad. In some embodiments, the entire sensor 310 is made flexible. In some embodiments, only a portion of the sensor 310 is made flexible (e.g., a first portion of the sensor 310 is rigid while a second portion of the sensor 310 is flexible). For example, in some embodiments, the extension 313 is flexible, while the rest of the sensor 310 (called herein a sensing portion) is rigid.

Figures 32A, 32B:
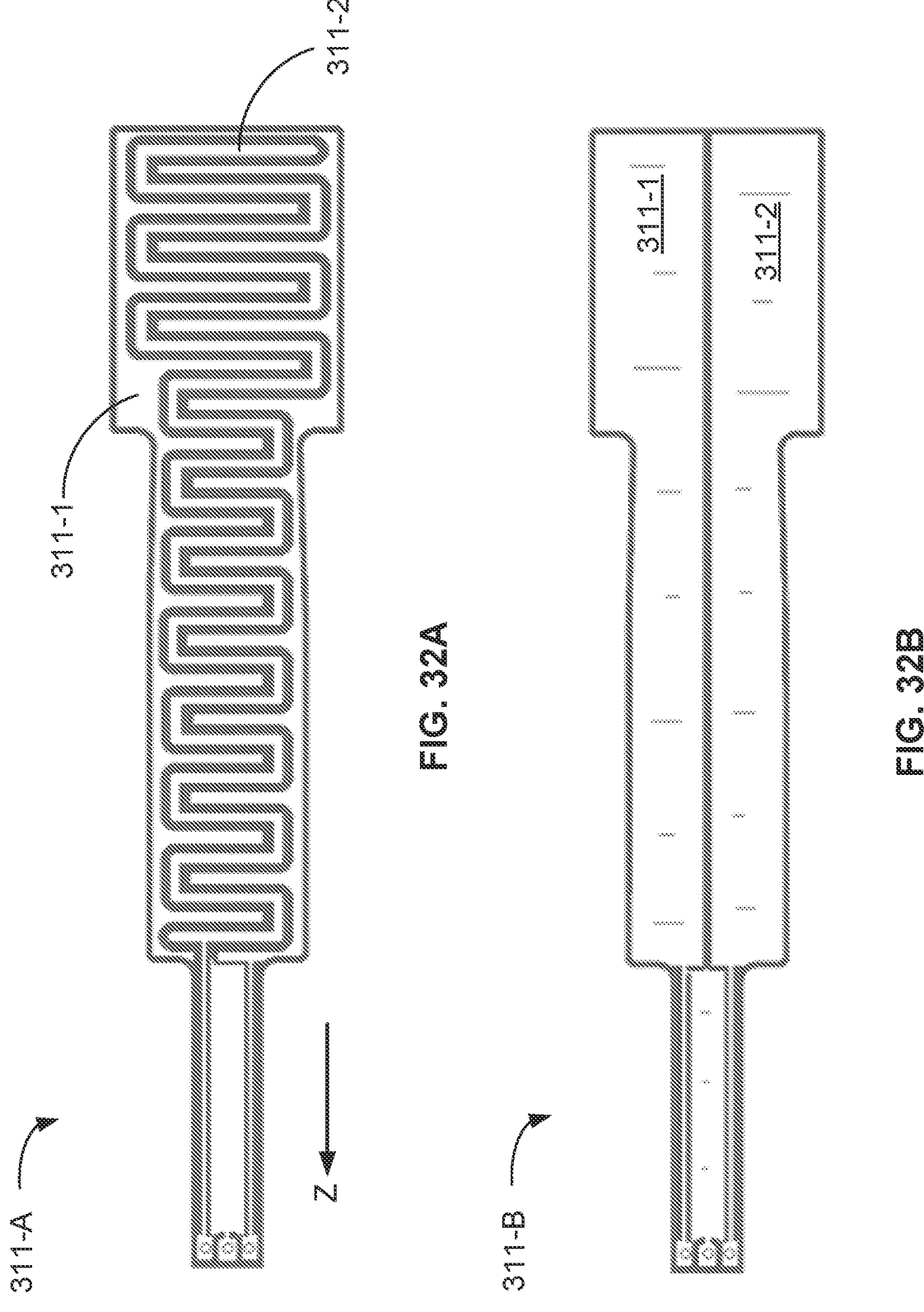
FIGS. 32A and 32B illustrate examples of electrode configurations for the sensor shown in FIG. 29 in accordance with some embodiments.

FIGS. 32A and 32B illustrate examples of electrode configurations for the sensor shown in FIG. 29A. FIG. 32A illustrates an electrode configuration 311-A that includes a first electrode 311-1 that is interleaved with a second electrode 311-2. In some implementations, the electrode configuration 311-A provides consistent sensitivity across its surface area. FIG. 32B illustrates another electrode configuration 311-B that includes the first electrode 311-1 being disposed side-by-side to the second electrode 311-2. In some implementations, the electrode configuration 311-B provides electrodes with large surface areas, thereby providing high sensitivity.

Figure 33:
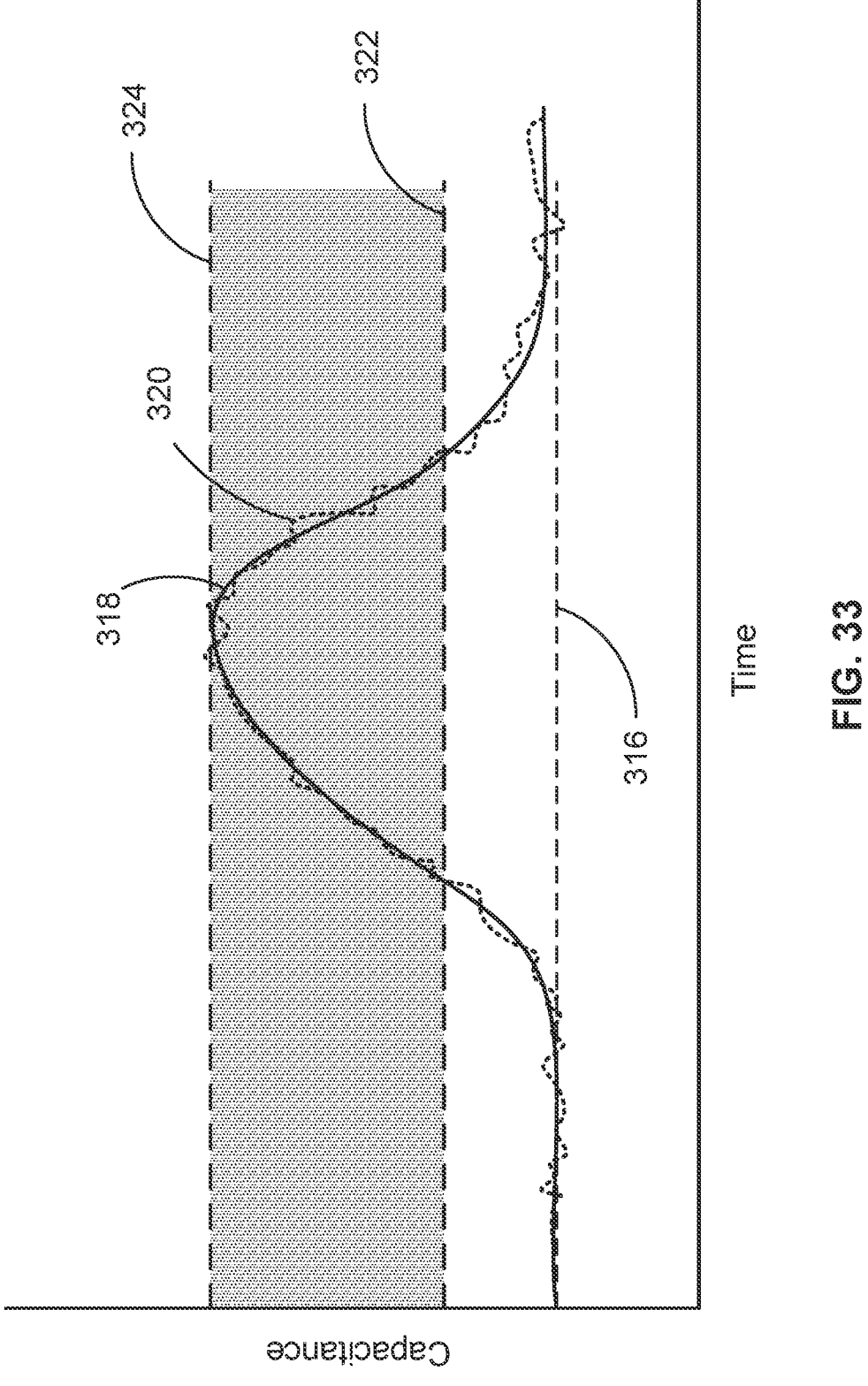
FIG. 33 illustrates an example measurement for sensing a user presence using the sensor shown in FIGS. 29A and 29B in accordance with some embodiments.

FIG. 33 illustrates an example measurement for sensing a user presence using the sensor shown in FIGS. 29A and 29B. FIG. 33 illustrates an example graph showing a signal 318 corresponding to a measured capacitance between two electrodes 311-1 and 311-2 of a sensor 310 over time in response to a user's body part changing its distance to the electrodes 311-1 and 311-2. As shown, the signal 318 increases from a baseline value 316 (e.g., a background capacitance value when a user's body part is not proximate to the electrodes 311-1 and 311-2) in response to a user's body part approaching the electrodes 311-1 and 311-2 of the sensor 310. The signal 318 increases above a detection threshold value 322 until it reaches a maximum capacitance value 324. The detection threshold value 322 corresponds a capacitance value above which a user presence is deemed to be present. In some embodiments, the detection threshold value 322 is selected in a way so that the difference between the detection threshold value 322 and the baseline value 316 is greater than a representative value of noise 320 (e.g., 3, 4, 5, 6, 7, 8, 9, or 10 times greater than a root-mean-squared amplitude of the noise 320 detected by the electrodes 311-1 and 311-2).

In some embodiments, the signal 318 is processed (e.g., by the integrated circuit 328) before determining the user presence. For example, the signal 318 is filtered to remove or reduce the noise 320 (e.g., based on the rate of change by using, for example, a frequency domain filter, such as a Fourier filter or a derivative integral filter).

Figure 34A:
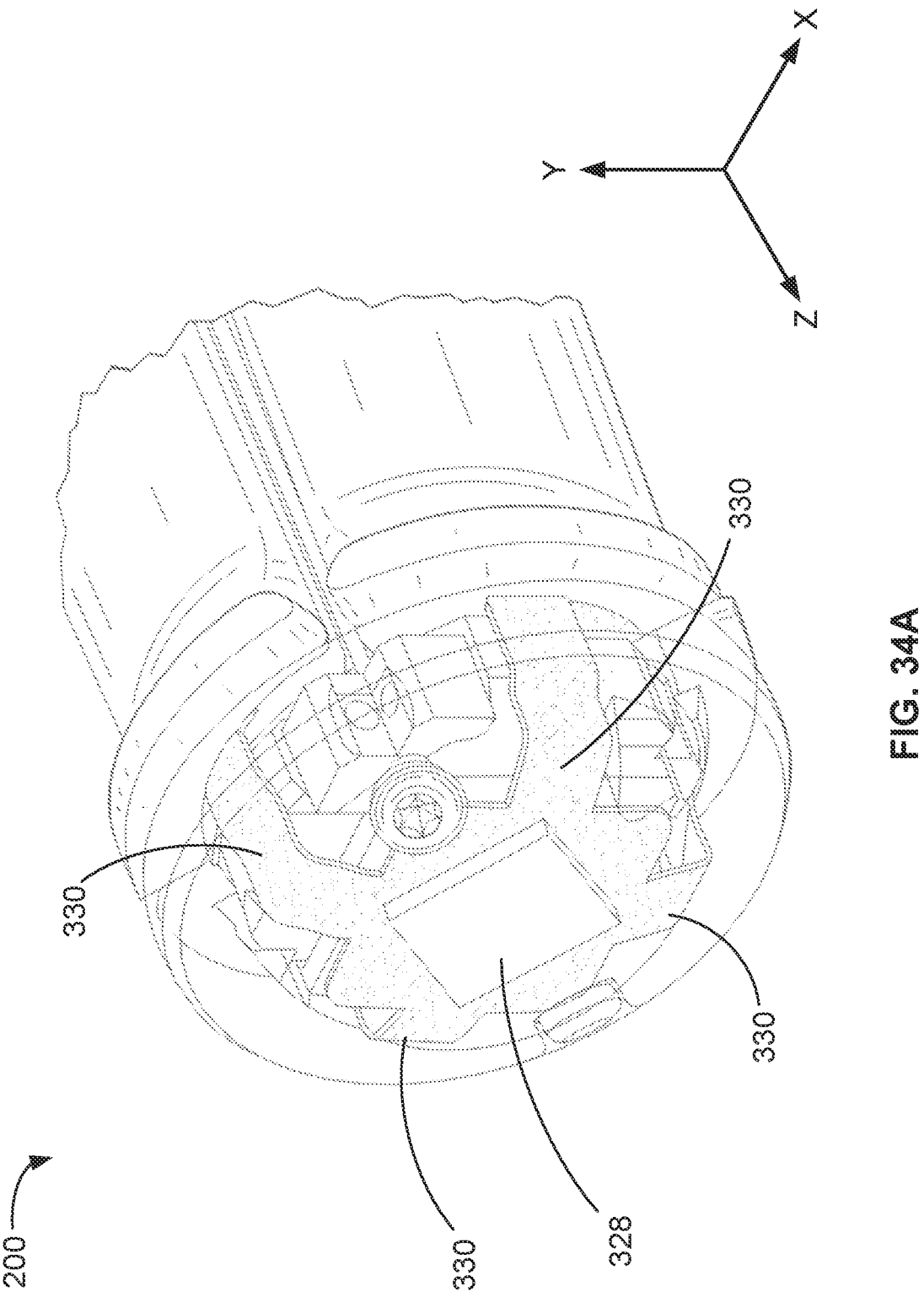
FIGS. 34A and 34B illustrate coupling of the sensor shown in FIGS. 29A and 29B to an integrated circuit for sensing a user presence in accordance with some embodiments.

FIG. 34A illustrates coupling of the sensor shown in FIGS. 29A and 29B to an integrated circuit 328 for sensing a user presence. The sensor includes a flexible connector 330 (corresponding to the extension 313) for electrical connection to the integrated circuit. This allows the relative movement (e.g., a rotational movement) of the sensing portion of the sensor to the integrated circuit 328 while maintaining the electrical contact between the sensing portion of the sensor to the integrated circuit 328, which may be located at the tip of the grasper 200.

Figure 34B:
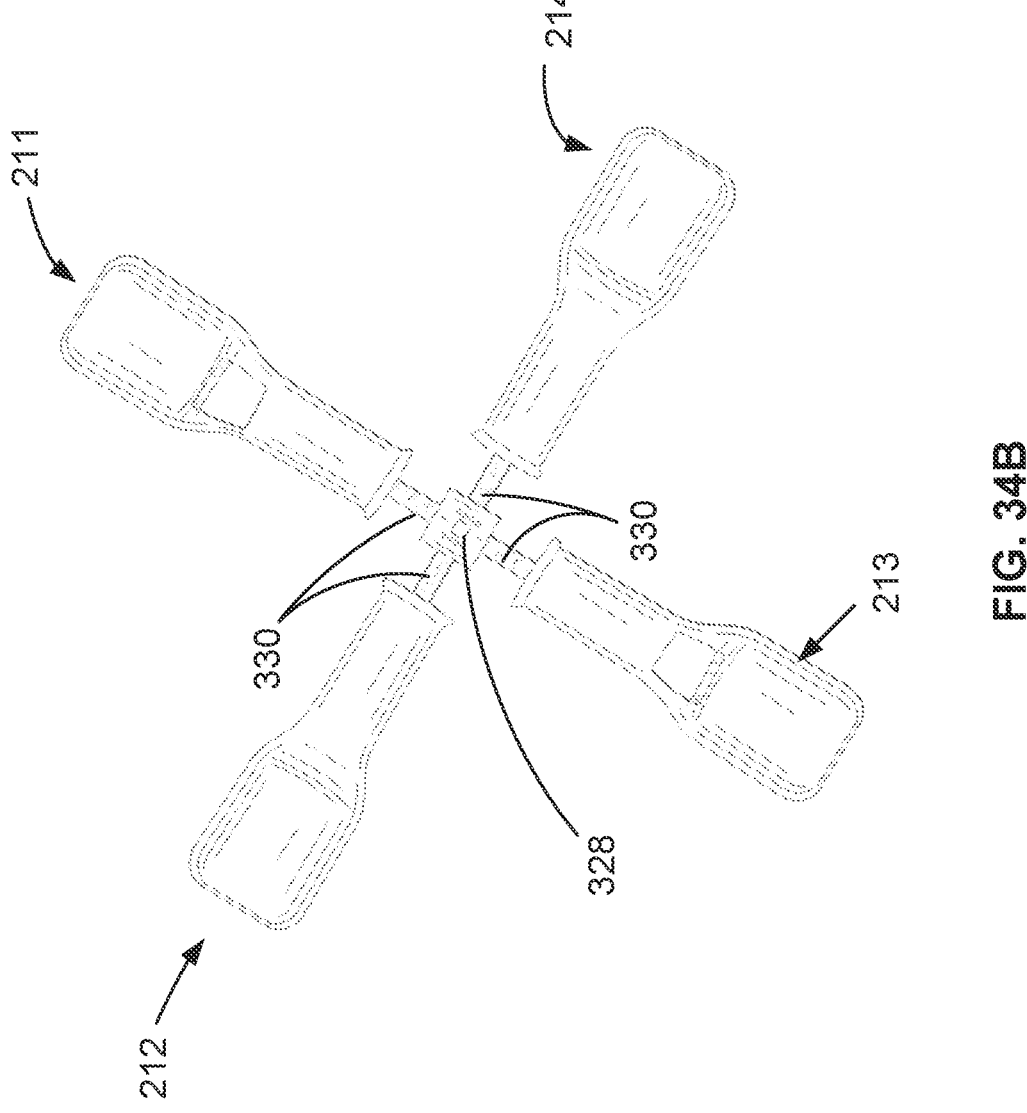

In some embodiments, each finger pad of the grasper 200 includes a sensor and the sensor of each finger pad is electrically coupled to the integrated circuit 328 through the flexible connector 330. For example, when the grasper 200 includes four finger pads (and hence at least four sensors), the integrated circuit 328 is electrically coupled to the four sensors via four flexible connectors 330 (e.g., one flexible connector 330 for each sensor). FIG. 34B illustrates four flexible connectors 330 electrically coupling the four sensors embedded in the four finger pads 211 through 214 to the integrated circuit 328.

C. Optical Sensors

Figure 35A:
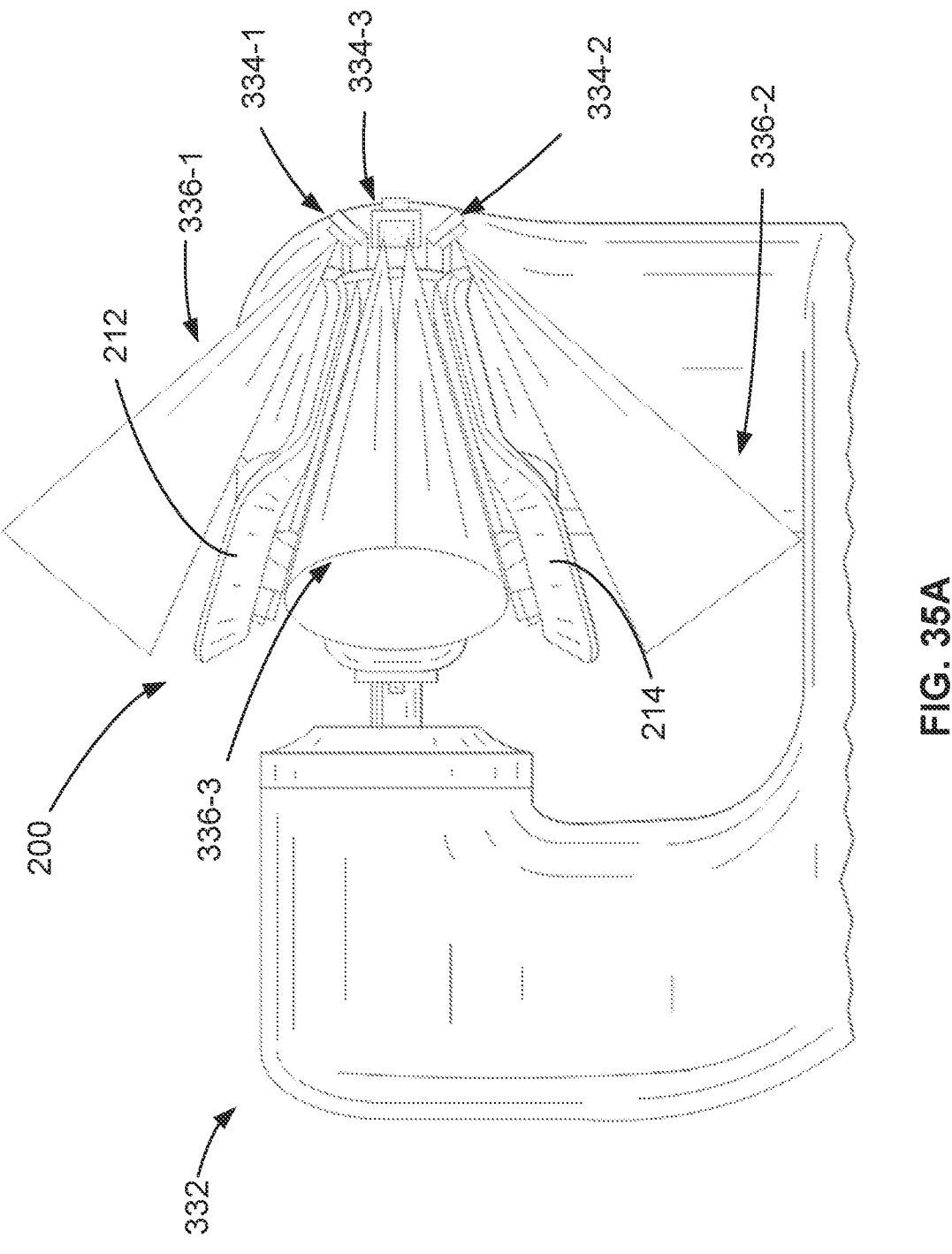
FIGS. 35A and 35B illustrate examples of light curtain configurations generated by optical sensors located at the input device of FIG. 21A for sensing a user presence in accordance with some embodiments.
Figure 35B:
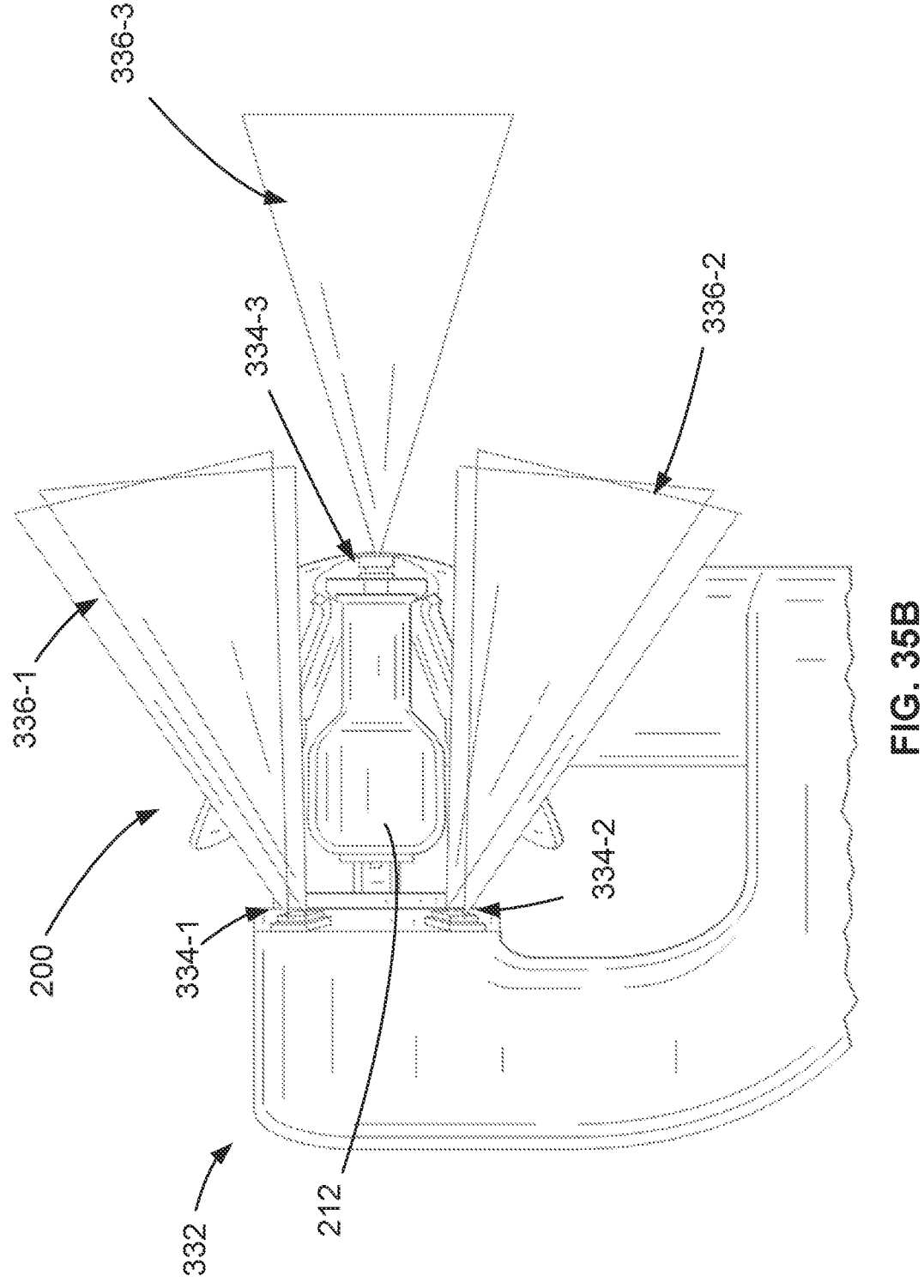

FIGS. 35A and 35B illustrate examples of light curtain configurations generated by optical sensors located at the input device of FIG. 21A for sensing a user presence.

In FIG. 35A, the grasper 200, mounted on a gimbal 332, is coupled with one or more optical sensors 334 (e.g., optical sensors 334-1 through 334-3). The one or more optical sensors 334 detect optical signals from a user's body part to determine the user presence. In some embodiments, the one or more optical sensors 334 are coupled with, or include, a light source for providing illumination light and the one or more optical sensors detect light that has been reflected or scattered by the user's body part, such as finger(s). In some embodiments, each of the one or more optical sensors 334-1 through 334-3 is coupled with, or includes, a light source for providing light curtains 336-1 through 33-6, respectively. In some embodiments, the one or more optical sensors 334 include a time-of-flight sensor for determining a distance from the time-of-flight sensor to an object (e.g., the user's body part) that comes into a corresponding light curtain. In some embodiments, each of the one or more optical sensors 334 is a time-of-flight sensor. In some embodiments, the one or more optical sensors 334 include other types of optical sensors (e.g., beam break sensors, LIDAR, cameras, etc.). In some embodiments, the one or more optical sensors 334 are amounted adjacent to one end of the grasper 200 toward the gimbal 332 toward to the opposite end of the grasper 200, as shown in FIG. 35A. This configuration allows placing the one or more optical sensors 334 so that fingers are placed within the field of view of the one or more optical sensors 334.

In FIG. 35B, at least a subset of the one or more optical sensors 334 (e.g., the optical sensors 334-1 and 334-2) is mounted on the gimbal 332 facing toward the grasper 200 (e.g., the one end of the grasper 200 that is not directly coupled to the gimbal 332). In some embodiments, the optical sensors 334-1 and 334-2 are placed to avoid occlusion by the finger pads. In some embodiments, the one or more optical sensors 334 also include at least one optical sensor 334-3 mounted on the one end of the grasper 200 (facing away from the opposite end of the grasper 200 coupled to the gimbal 332). This optical sensor may be used to detect a presence of a user's palm, which can provide additional information for determining the user presence.

Although FIGS. 35A and 35B show three optical sensors, in some embodiments, additional or fewer optical sensors may be used (e.g., 1, 2, 4, 5, 6, 7, 8, 9, 10, or more optical sensors).

In addition, although FIGS. 35A and 35B are used to describe placement of optical sensors, other types of sensors (e.g., ultrasonic sensors, radar, sonar, pressure sensors, etc.) may be used instead of, or in addition to, the optical sensors.

Figure 36A:
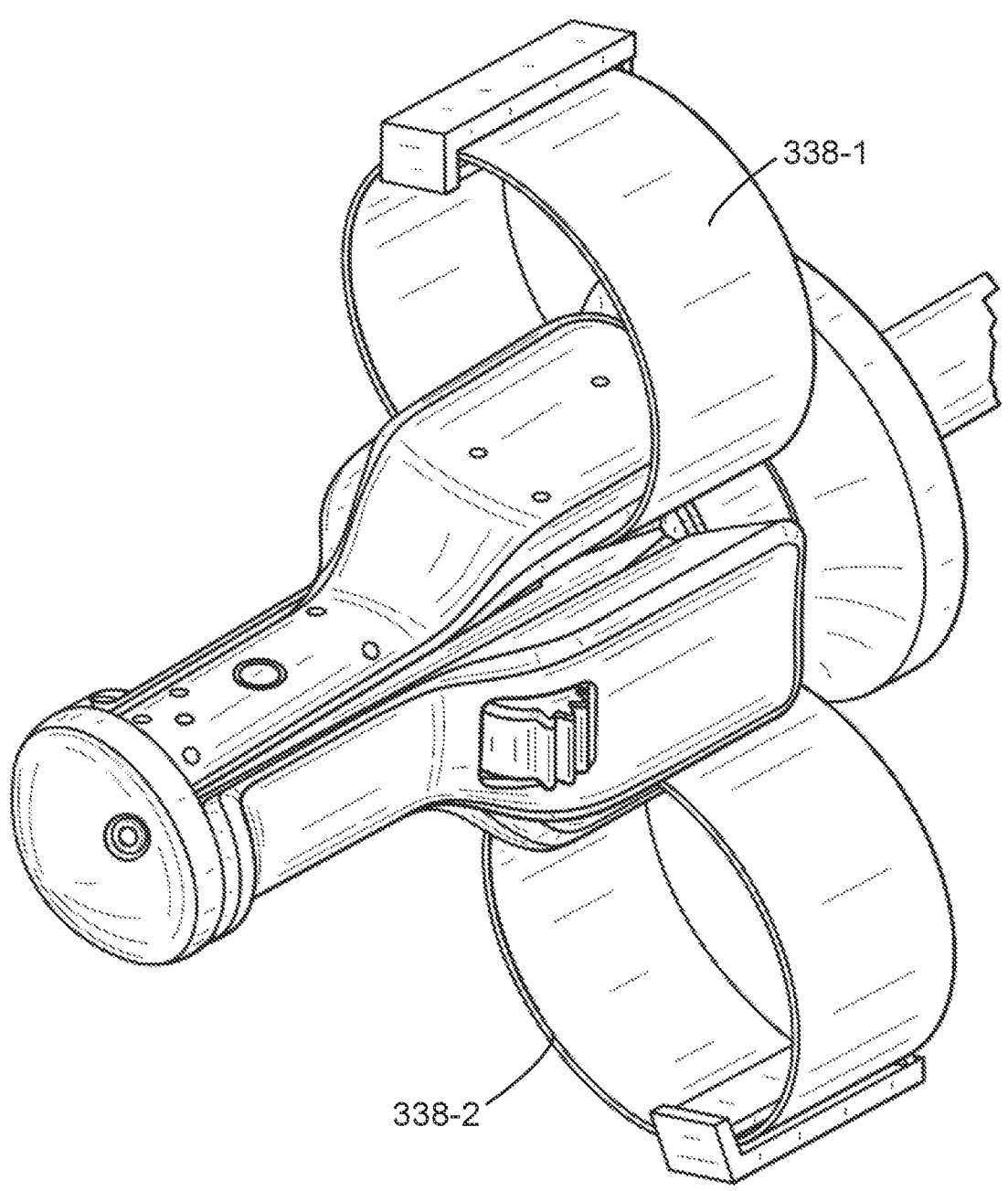
FIGS. 36A and 36B illustrate examples of finger loops for use in conjunction with time-of-flight sensors at the input device of FIG. 21A in accordance with some embodiments.
Figure 36B:
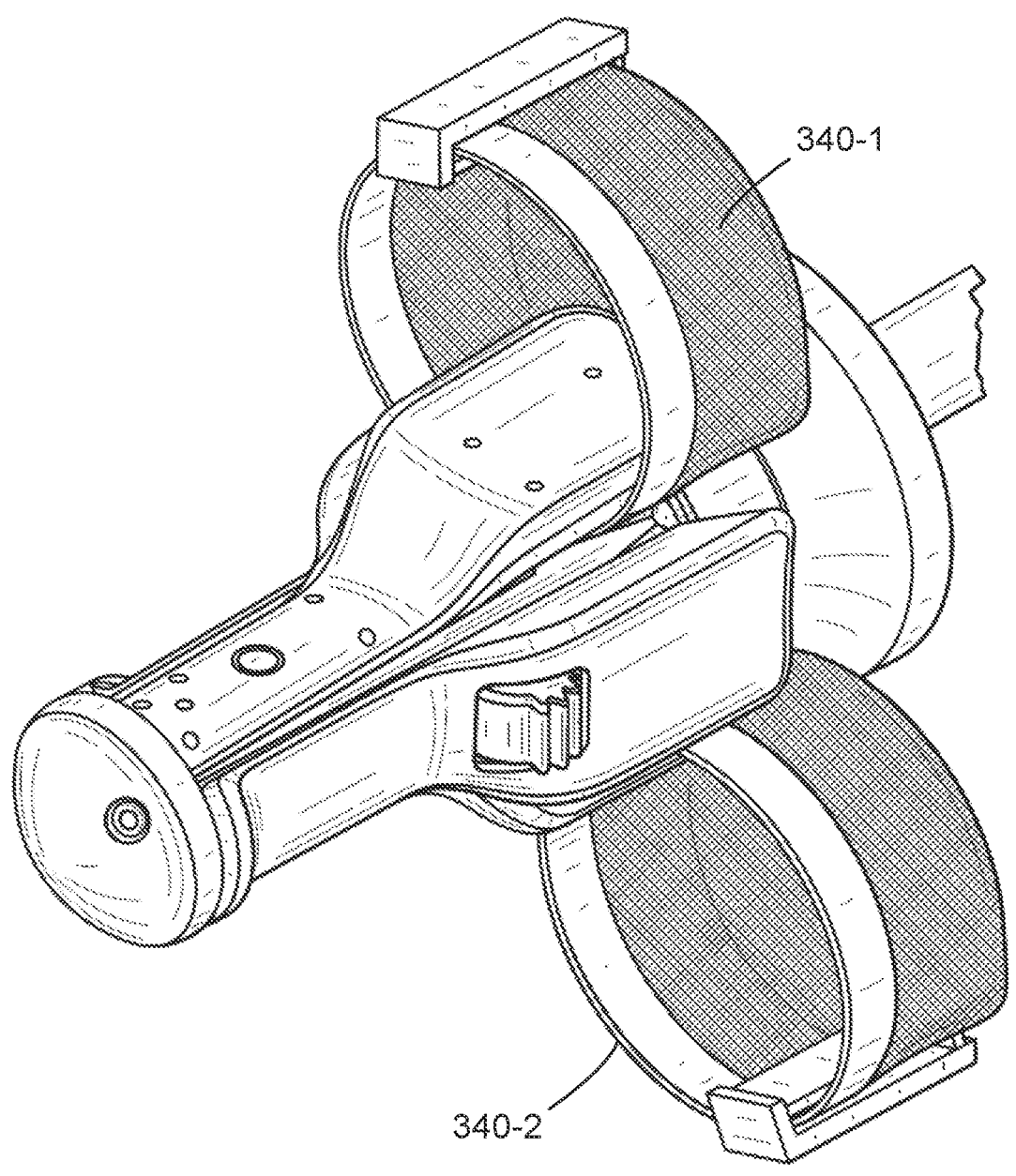

FIGS. 36A and 36B illustrate examples of finger loops for use in conjunction with optical sensors at the input device of FIG. 21A. FIG. 36A shows finger loops 338-1 and 338-2 (with open ends) and FIG. 36B shows finger loops 340-1 and 340-2 (with closed ends, in which case the finger loops may be called finger cups). The finger loops 338 provide a secure connection between the user and the grasper. In some embodiments, the integrated circuit 328 is configured to distinguish the finger loops from the user's body parts (e.g., using threshold windows to differentiate signals from the user's body parts and signals from the finger loops) In some implementations, the wall of the finger cups 340 facilitate distinguishing the user's body parts from the finger cups 340.

As described herein, the sensors (e.g., capacitance sensors, optical sensors, etc.) are used to determine the user presence, which can be used to reduce or eliminate unintended movements of the robotic arms or surgical tools. It is also helpful to determine the user control even when the user contact is not detected on the grasper 200. For example, when the user uses the finger loops or finger cups (shown in FIGS. 36A and 36B) to control the grasper (e.g., during the opening of the grasper 200), the user is still in control of the grasper 200, although the user may not be in contact with (or in proximity to) the sensors within the finger pads as the fingers are lifted away from the finger pads.

D. Enhanced Determination of User Presence or Absence

In some embodiments, user control is determined by combining, information from the one or more sensors described above (e.g., capacitance sensors and/or optical sensors) with additional information (also called herein secondary information). In some embodiments, the movement of the robotic arms or surgical tools is controlled based on the information from the one or more sensors (e.g., capacitance sensors and/or optical sensors) and the secondary information, thereby enhancing operation of medical robotic systems.

In some embodiments, the additional information includes a grasper angle (e.g., an angle defined by the central axis of the grasper and a link, such as link 202). In some configurations, the grasper is at a fully-open angle (e.g., as shown in FIG. 24A) when no external force is applied (e.g., no user input). Thus, a grasper angle other than, or less than, a predefined grasper angle threshold (e.g., the fully-open angle) indicates that the user is in control.

Figure 37:
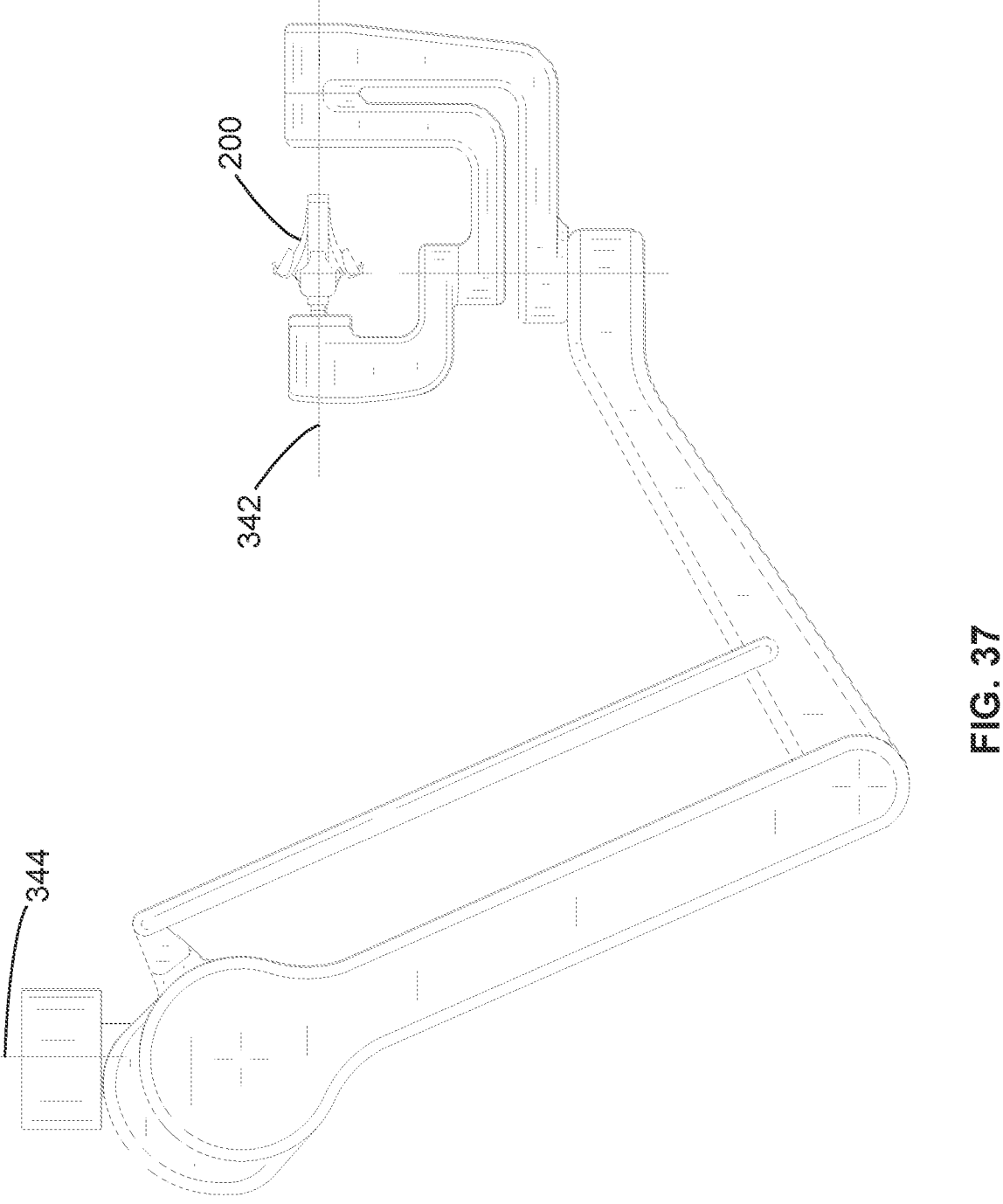
FIG. 37 illustrates robotic joints of a gimbal supporting the input device of FIG. 21A in accordance with some embodiments.

In some embodiments, the additional information includes a velocity or movement of one or more joints supporting the input device. FIG. 37 illustrates robotic joints supporting the input device of FIG. 21A in accordance with some embodiments. For example, as shown in FIG. 37, a gimbal roll axis 342 extends through a roll joint that is rotatably coupled with the grasper 200 along the axis of the grasper 200. The roll joint is designed to have passively zero velocity (e.g., there is no gravity compensation), so there cannot be any gravity compensation error. As such, it has no movement (and hence, zero velocity) when there is no user input to the grasper 200 (e.g., when the user is not operating the grasper 200). Thus, a rotational movement (or a rotational velocity) of the rolling joint along the gimbal roll axis 342 indicates that the user is in control (e.g., the user is rotating the grasper 200 about the gimbal roll axis 342). In another example, a rotational joint extending through a shoulder yaw axis 344 is coupled to the grasper 200. The rotational joint extending through the shoulder yaw axis 344 has no movement (and hence, zero velocity) when there is no user input to the grasper 200 (e.g., when the user is not operating the grasper 200). Thus, a rotational movement (or a rotational velocity) of the rotational joint extending through the shoulder yaw axis 344 can also indicate that the user is in control (e.g, the user is moving the grasper 200 about the shoulder yaw axis 344).

In some embodiments, the additional information includes a time period or duration from the most recent detection of user presence. By providing a time duration as an additional input, the system can advantageously account for when a user might be present, but temporarily withdraws his or her hand from the grasper for a short period (e.g., 0.01-0.04 seconds). In such a situation, the system may not want to halt movement of the robotic arms or surgical tools, as this may cause unnecessary interruptions, despite the presence of the user. Accordingly, in some embodiments, the system can incorporate different temporal thresholds to help refine the determination of user presence and control. For example, a first time threshold can be provided (e.g., 0.05-1 second or greater) as a debounce, whereby if a user is not detected by the system within the first time threshold, movement may be reduced or halted and/or monitored for unintended movement above a distance threshold. A second time threshold (e.g., 60 seconds, 90 seconds, 120 seconds, or greater) can be provided as a timeout, whereby if a user is not detected by the system within the second time threshold, movement may be automatically halted regardless of the distance of the unintended movement. Note that the time periods provided above for the first threshold and the second threshold are exemplary and not meant to be limiting.

In some embodiments, the additional information includes information indicating a change in the movement of robotic arms or surgical tools that is inconsistent with a user input. Such information can come from encoders (e.g., position sensors) and/or from derived information based on changes to velocity, acceleration, jerking, etc. For example, a bump or impulse in a motion profile of the robotic arms or surgical tools or information from mechatronic sensors, such as current, back electromotive force, torque, or force, could indicate movement of the robotic arms or surgical tools that are different from the movement of the robotic arms or surgical tools caused by the user input. In another example, gravity drift is detected based on the information from mechatronic sensors (e.g., an error in gravity compensation may result in a constant acceleration in a constant direction).

Figure 38A:
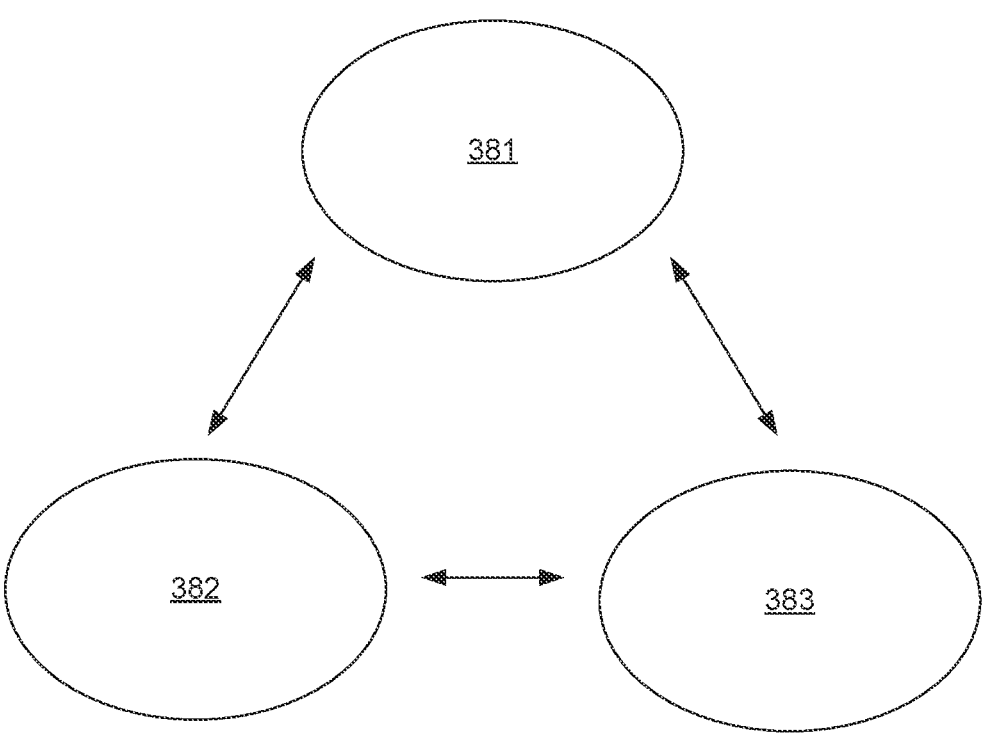
FIG. 38A is a state diagram illustrating states of a medical system in accordance with some embodiments.

FIG. 38A illustrates a state diagram for the medical robotic system in accordance with some embodiments. The state diagram includes a (unmodified) teleoperation mode 381, a modified teleoperation mode 382, and a safe mode 383.

In some embodiments, in accordance with a determination that user control is detected, the medical robotic system enters or remains in the (unmodified) teleoperation mode 381. In some embodiments, while the medical robotic system is in the (unmodified) teleoperation mode 381, the medical robotic system moves robotic arms and/or surgical instruments in accordance with a user input without any damping (or with a first damping that is less than a second damping provided while the medical robotic system is in the modified teleoperation mode 382).

In some embodiments, in the event that lack of user control is detected in conjunction with movement of the robotic arms or surgical tools, the medical robotic system can transition into the safe mode 383. While the medical robotic system is in the safe mode 383, teleoperation is halted or cut off between the input device and the robotic arm or surgical instrument. In some embodiments, to avoid unnecessary disruptions, the medical robotic system monitors the movement of the input device, and transition into the safe mode 383 if the position of the input device has changed by an unsafe distance in comparison to when the user was last detected to be in active control. Additionally or alternatively, the medical robotic system can transition into the safe mode 383 if the motion (velocity, acceleration, etc.) of the input device is considered unsafe (e.g., the velocity of the input device exceeds a velocity threshold or the acceleration of the user acceleration exceeds an acceleration threshold) while the user is not detected to be in active control.

In some implementations, the medical robotic system, prior to entering the safe mode 383, still modifies control algorithms to decrease the likelihood of hazardous unintended motion via (i) changing motion scaling so the input device motion results in smaller tool tip motion; (ii) adjusting damping on the input device to increase the load required to create input device motion; (iii) command haptic feedback to maintain a current position of the input device; and (iv) saturate commanded velocity from the input device at a lower value than during normal operation. For example, any of the foregoing (i) to (iv) can also be provided while the medical robotic system is in the modified teleoperation mode 382. The advantage of (i) to (iv) is that the teleoperation is not interrupted unnecessarily. For example, a situation may occur where though a user presence/control might not be detected, it may not be warranted to enter into a safe mode whereby teleoperation is halted. In such a scenario, the system can, for example, dampen the motion of the input device, instead of immediately halting teleoperation of the system.

Although the system diagram shown in FIG. 38A includes state transitions between the (unmodified) teleoperation mode 381 and the modified teleoperation mode 382, state transitions between the modified teleoperation mode 382 and the safe mode 383, and state transitions between the (unmodified) teleoperation mode 381 and the safe mode 383, in some implementations, one or more state transitions may be omitted or blocked (e.g., in some implementations, state transitions between the modified teleoperation mode 382 and the safe mode 383 may not be allowed).

Although the system diagram shown in FIG. 38A has three states, in some embodiments, the system diagram may include additional or fewer states (e.g., the system diagram may have only two states, such as the (unmodified) teleoperation mode 381 and the safe mode 383)

Figure 38B:
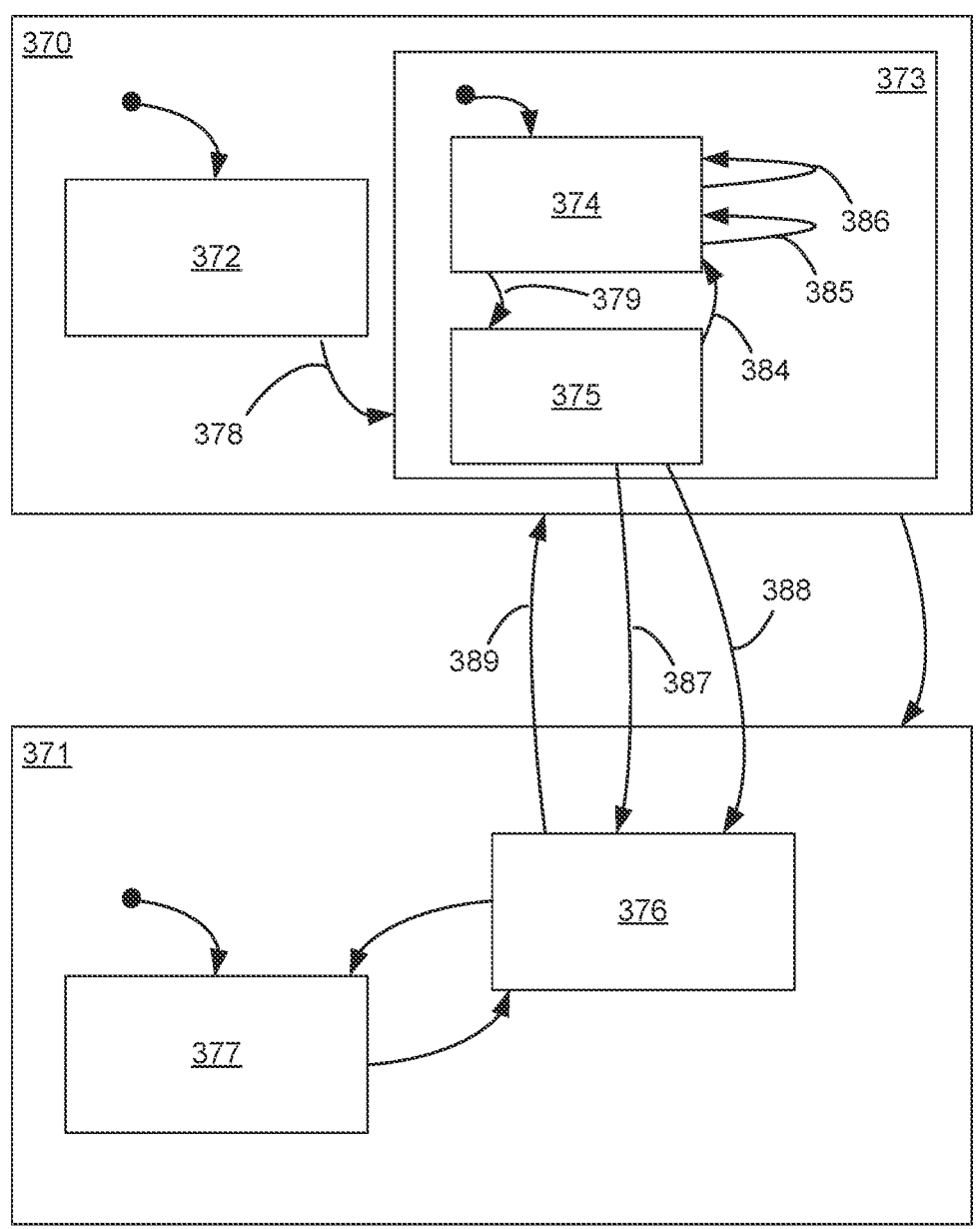
FIG. 38B illustrates transitions among different states of a medical system in accordance with some embodiments.

FIG. 38B illustrates transitions among different states of a medical system in accordance with some embodiments.

The states illustrated in FIG. 38B include engaged state 370 and disengaged state 371. In some embodiments, the engaged state 370 includes substates, such as "not driving" state 372, which indicates that a user is not in control, and driving state 373, which indicates that a user is in control. In some embodiments, the driving state 373 includes also includes substates, such as "user detected" state 374, which indicates that a user is detected (e.g., using a capacitance sensor) and "user not detected" state 375 (e.g., using a capacitance sensor). Thus, a user may be in control (e.g., the medical system is in the driving state 373) even though the user is not detected (the "user not detected" state 375, which is a substate of the driving state 373). In some embodiments, the disengaged state 371 includes substates, such as "head in" state 376 and "head out" state 377.

In some embodiments, the medical system (378) transitions from the "not driving" state 372 to the driving state 373 in accordance with a determination that a gripper is matched. In some embodiments, the medical system unlocks a haptic input device in conjunction with transitioning from the "not driving" state 372 to the driving state 373. In some embodiments, the medical system (379) transitions from the "user detected" state 374 to the "user not detected" state 375 in accordance with a determination that user presence is not detected (e.g., no sensor has detected user presence, or less than a certain number (e.g., two, three, or four) of sensors have detected user presence and a grasper angle is greater than a first threshold angle (e.g., 30°, 40°, 45°, etc.) and the shoulder yaw axis 344 has a rotational speed below a first threshold speed (e.g., less than 0.1 rad/s, 0.2 rad/s, 0.3 rad/s, 0.4 rad/s, 0.5 rad/s, 0.6 rad/s, 0.7 rad/s, 0.8 rad/s, 0.9 rad/s, 1 rad/s, 2 rad/s, 3 rad/s, 4 rad/s, 5 rad/s, or 10 rad/s, etc.)). In some embodiments, the medical system (384) transitions from the "user not detected" state 375 to the "user detected" state 374 in accordance with a determination that any sensor has detected user presence. For example, the medical system may transition to the "user detected" state 374 in accordance with a determination that a certain number of sensors (e.g., capacitance sensors), such as two or more sensors, have detected user presence, or a grasper angle is closed (e.g., less than a second threshold angle, such as 15°, 10°, 5°, etc.), or the shoulder yaw axis 344 has a rotational speed above a second threshold speed (e.g., greater than 0.1 rad/s, 0.2 rad/s, 0.3 rad/s, 0.4 rad/s, 0.5 rad/s, 0.6 rad/s, 0.7 rad/s, 0.8 rad/s, 0.9 rad/s, 1 rad/s, 2 rad/s, 3 rad/s, 4 rad/s, 5 rad/s, or 10 rad/s, etc.).

In some embodiments, the medical system resets a timer (and/or restarts the timer) in conjunction with transitioning to the "user detected" state 374 (e.g., the timer is used to determine whether the medical system should transition to the "user not detected" state 375). In some embodiments, the medical system, while in the "user detected" state 374, detects user presence (e.g., any sensor has detected user presence), and in response, (385) remains in the "user detected" state 374 and resets a timer (and/or restarts the timer) (e.g., for determining whether the medical system should transition to the "user not detected" state 375). In some embodiments, the medical system, while in the "user detected" state 374, does not detect user presence (e.g., no sensor has detected user presence), and in response, (386) remains in the "user detected" state 374 and resets a timer (and/or restarts the timer) (e.g., for determining whether the medical system should transition to the "user not detected" state 375). In some embodiments, the medical system (387) transitions from the "user not detected" state 375 to the "head in" state in accordance with a determination that the timer has elapsed a threshold duration (e.g., 5, 6, 7, 8, 9, 10, 11, 12, 13, 14, 15, 16, 17, 18, 19, 20, 25, 30, 40, 50, or 60 seconds or within an interval between any two of the aforementioned values). In some embodiments, the medical system locks the haptic input device (e.g., stops movement of the robotic arm or the surgical tool in response to movement of the haptic input device) in conjunction with transitioning to the "head in" state. In some embodiments, the medical system (388) transitions from the "user not detected" state 375 to the "head in" state in accordance with a determination that a robotic arm or a surgical tool has drifted more than a distance threshold (e.g., 5, 6, 7, 8, 9, 10, 11, 12, 13, 14, 15, 16, 17, 18, 19, 20, 25, 30, 40, 50, or 60 mm or within an interval between any two of the aforementioned values). In some embodiments, the medical system locks the haptic input device in conjunction with transitioning to the "head in" state. In some embodiments, the medical system (389) transitions from the disengaged state 371 to the engaged state 370 in accordance with a determination that any sensor has detected user presence. In some embodiments, the medical system resets a timer (and/or restarts the timer) in conjunction with transitioning from the "head in" state 376 to the engaged state 370.

In some embodiments, the medical system resets a timer (and/or restarts the timer) in conjunction with transitioning to the "user not detected" state 375. In some embodiments, the timer can serve as secondary information (e.g., in addition to sensing via capacitance) to help determine when the system can properly transition back to a "user detected" state 374. For example, in some embodiments, when the system is in the "user not detected" state 375, it may take a certain amount of time before the system transitions back to the "user detected" state 374, even beyond the initial contact between the user and the graspers and the associated capacitance sensors.

In another embodiment, the secondary information (with or without the sensor information) is used to determine criteria for a state transition. In some embodiments, the medical system resets a timer (and/or restarts the timer) in conjunction with transitioning to the "user not detected" state 375. In some embodiments, the timer can serve as secondary information (e.g, in addition to sensing via capacitance) to help determine the criteria for when the system can properly transition back to a "user detected" state 374. For example, in some embodiments, when the system is in the "user not detected" state 375 for longer than a pre-defined duration (e.g., 1 second), the system may require specific criteria based on the contact sensing and/or secondary information to transition back to "user detected" state 374. This criteria could be different than the criteria to re-establish "user detection" if the user has not been detected for less than that duration. For example, the system may require only 1 sensor to indicate presence if the system was in "user not detected" state 375 for less than 1 second, and require at least 2 sensors to indicate presence if the system was in "user not detected" state 375 for more than 1 second. Alternatively, the system may allow secondary information such as G6 motion to indicate presence if the system was in "user not detected" state 375 for less than 1 second, but require contact sensors to indicate presence if the system was in "user not detected" state 375 for more than 1 second. Providing a timer as secondary information in the "user not detected" state can advantageously help determine what criteria from the information warrants the transition back to "user detected".

In some embodiments, the medical system resets a timer (and/or restarts the timer) in conjunction with transitioning to the disengaged state 371 (e.g., "head in" state 376). In some embodiments, the timer can serve as secondary information (e.g., in addition to sensing via capacitance) to help determine when the system can properly transition back to the engaged state 370 (e.g., the driving state 373, and in particular the "user detected" state 374). For example, in some embodiments, when the system is in the disengaged state 371 (e.g., "head in" state 376), it may take a certain amount of time before the system transitions back to the engaged state 370 (e.g., the driving state 373, and in particular "user detected" state 374), even beyond the initial contact between the user and the graspers and the associated capacitance sensors. This is because the system may want to account for the initial touch by the user with the grasper pads prior to actual teleoperated driving. In other words, the system may not want to go straight to the driving state 373 upon the user's initial contact with the graspers. Providing a timer as secondary information in the disengaged state 371 can advantageously help determine whether a user's contact has been made with the graspers long enough to warrant actual driving. In some embodiments, the medical system resets the timer (and/or restarts the timer) in response to detecting the user presence (so that a certain period of time (e.g., 0.2, 0.3, 0.4, 0.5, 0.6, 0.7, 0.8, 0.9, or 1 second) after the user presence has been detected can elapse before allowing the user to drive the robotic arm).

In some embodiments, the medical system resets a timer (and/or restarts the timer) in conjunction with transitioning to the disengaged state 371 (e.g., "head in" state 376). In some embodiments, the timer can serve as secondary information (e.g., in addition to sensing via capacitance) to help determine the criteria for when the system can properly transition back to a the engaged state 370 (e.g., the driving state 373, and in particular the "user detected" state 374). For example, in some embodiments, when the system is in the disengaged state 371 for longer than a pre-defined duration (e.g., 1 second), the system may require specific criteria based on the contact sensing and/or secondary information to transition back to the engaged state 370 (e.g., the driving state 373, and in particular the "user detected" state 374) This criteria could be different than the criteria to re-establish "user detection" if the user has not been detected for less than the pre-defined duration. For example, the system may require only 1 sensor to indicate presence if the system was in the disengaged state 371 for less than 1 second, and require at least 2 sensors to indicate presence if the system was in the disengaged state 371 for more than 1 second. Alternatively, the system may allow secondary information such as a rotational movement (or a rotational velocity) of a rotational joint extending through the shoulder yaw axis 344 to indicate user presence if the system was in the disengaged state 371 for less than 1 second, but also require contact sensors to indicate user presence if the system was in the disengaged state 371 for more than 1 second. Providing a timer as secondary information in the disengaged state 371 can advantageously help determine what criteria from the information warrants the transition back to the engaged state 370 (e.g., the driving state 373, and in particular, the "user detected" state 374) and actual driving.

In some embodiments, the secondary information includes an end effector pose or information indicating a change in the end effector pose. For example, in some embodiments, the secondary information includes (i) the end effector pose or the information indicating a change in the end effector pose, and (ii) a rotational movement (or a rotational velocity) of a rotational joint extending through the shoulder yaw axis 344 so that the user control is determined based on the change in the end effector pose and the rotational movement, even when no user contact is detected (e.g., using a capacitance sensor). In some embodiments, the change in the end effector pose is used to select the criteria for the state transition. For example, in accordance with a determination that a movement, of the end effector, that is associated with user control (e.g., continuous or semi-continuous movement of the end effector, movement of the end effector at a speed below a threshold speed, movement of the end effector that includes a change in a direction of the end effector) is detected, first criteria (e.g., less stringent criteria, such as requiring detection of contact by a single sensor) are used for a state transition. In accordance with a determination that a movement, of the end effector, that is not associated with user control (e.g., gravity drift or bump), second criteria (e.g., more stringent criteria, such as requiring detection of contact by multiple sensors) are used for a state transition.

FIGS. 39A and 39B are a flowchart illustrating a method 400 for operating a surgical tool via the input device of FIG. 21.

The method 400 includes, while operating a robotic arm in response to information from an input device, (4010) receiving first information from a first set of two or more electrodes (e.g., electrodes 311-1 and 311-2).

In some embodiments, the method 400 also includes (4020) determining, by an integrated circuit (e.g., integrated circuit 328), a mutual capacitance between the two or more electrodes of the first set of two or more electrodes (e.g., the integrated circuit includes circuit 301 electrically coupled to the electrode as shown in FIGS. 30B and 30C). The user presence is determined based at least in part on the mutual capacitance (e.g., a change in the mutual capacitance, above a threshold value, indicates the user presence).

The method 400 also includes (4030) determining a user presence at a first finger pad based on the first information. The first finger pad includes the first set of two or more electrodes. The method 400 further includes (4040) modifying operation (e.g., teleoperation) of the robotic arm in response to the information from the input device in accordance with a determination of the user presence at the first finger pad. In some embodiments, the method 400 further includes modifying operation (e.g., teleoperation) of the robotic arm in response to the information from the input device in accordance with a determination of lack of the user presence at the first finger pad.

In some embodiments, modifying teleoperation of the robotic arm includes (4042) ceasing movement of the robotic arm in response to the information from the input device (e.g., regardless of any input provided to the input device the robotic arm may not move).

In some embodiments, modifying teleoperation of the robotic arm includes (4044) reducing a velocity of the robotic arm in response to the information from the input device (e.g., the robotic arm moves at a first velocity before the modification, and the robotic arm moves at a second velocity less than the first velocity after the modification).

In some embodiments, modifying teleoperation of the robotic arm includes (4046) reducing motion scaling between the input device and the robotic arm. (e.g., reducing an amount of movement of the robotic arm with respect to an amount of movement of the input device). For example, the robotic arm may move by a first distance in response to movement of an input device by a particular input distance before the modification and the robotic arm may move by a second distance less than the first distance in response to movement of the input device by the particular input distance after the modification.

In some embodiments, the method 400 also includes (4050) receiving second information from a second set of two or more electrodes, and (4052) determining a user presence at a second finger pad based at least in part on the second information. The second finger pad includes the second set of two or more electrodes.

In some embodiments, the method 400 also includes (4054) receiving third information from a third set of two or more electrodes, and (4056) determining a user presence at a third finger pad based at least in part on the third information. The third finger pad includes the third set of two or more electrodes. The method 400 further includes (4058) receiving fourth information from a fourth set of two or more electrodes, and (4060) determining a user presence at a fourth finger pad based on the fourth information. The fourth finger pad includes the fourth set of two or more electrodes.

In some embodiments, the method 400 also includes (4070) modifying the operation of the robotic arm in response to the information from the input device in accordance with a determination of the user presence at the second finger pad. In some embodiments, the method 400 also includes modifying the operation of the robotic arm in response to the information from the input device in accordance with a determination of lack of the user presence at the second finger pad. In some embodiments, the method 400 includes modifying the operation of the robotic arm in response to the information from the input device in accordance with a determination of the user presence at the first finger pad and the user presence at the second finger pad. In some embodiments, the method 400 includes modifying the operation of the robotic arm in response to the information from the input device in accordance with a determination of lack of the user presence at the first finger pad and lack of the user presence at the second finger pad. In some embodiments, the method 400 includes modifying the operation of the robotic arm in response to the information from the input device in accordance with a determination of the user presence at the first finger pad, the user presence at the second finger pad, and the user presence at the third finger pad. In some embodiments, the method 400 includes modifying the operation of the robotic arm in response to the information from the input device in accordance with a determination of the user presence at the first finger pad, the user presence at the second finger pad, the user presence at the third finger pad, and the user presence at the fourth finger pad.

In some embodiments, the method 400 is performed by a medical system that includes an input device (e.g., the input system 182) for controlling (e.g., movement, function) operation (e.g., teleoperation) of a robotic arm. The input device includes a grasper (e.g., the grasper 200) that includes a first finger pad. The first finger pad includes a first set of two or more electrodes (e.g., electrodes 311-1 and 311-2) for determining a user presence at the first finger pad (e.g., user proximity to the first finger pad, or user contact with the first finger pad). The medical system also includes a processor (e.g., processor(s) 280) for modifying operation of the robotic arm in response to information (e.g., one or more electrical signals corresponding to a user input) from the input device in accordance with a determination of the user presence at the first finger pad (e.g., transition the medical system into a safe mode (e.g, safe mode 383) in accordance with (based at least in part on) a determination that the user is not present at the first finger pad, and transitioning the medical system out of the safe mode (e.g., to the teleoperation mode 381) in accordance with (based at least in part on) a determination that the user is present at the first finger pad). In some embodiments, the medical system also includes memory (e.g., memory 282) storing instructions for execution by the processor. The stored instructions include instructions for modifying the operation of the robotic arm in response to the information from the input device in accordance with the determination of the user presence at the first finger pad.

In some embodiments, the two or more electrodes include a first electrode and a second electrode that is interdigitated (e.g., coiled) with the first electrode.

In some embodiments, the two or more electrodes include a first electrode and a second electrode that is disposed adjacent to the first electrode. In some embodiments, the first electrode and the second electrode extend substantially in a same direction.

In some embodiments, the grasper includes a second finger pad distinct and separate from the first finger pad. The second finger pad includes a second set of two or more electrodes for determining a user presence (e.g., user proximity to the finger pad) at the second finger pad. The user presence at the second finger pad is determined independently of the user presence at the first finger pad.

In some embodiments, the grasper further includes a third finger pad and a fourth finger pad. In some embodiments, the grasper includes additional finger pads (e.g., a fifth finger pad, a sixth finger pad, etc.).

In some embodiments, the third finger pad includes a third set of two or more electrodes for determining a user presence (e.g., user proximity to the finger pad) at the third finger pad, and the fourth finger pad includes a fourth set of two or more electrodes for determining a user presence (e.g., user proximity to the finger pad) at the fourth finger pad. The user presence at the first finger pad, the user presence at the second finger pad, the user presence at the third finger pad, and the user presence at the fourth finger pad are determined independently of each other.

In some embodiments, in accordance with a determination of a lack of the user presence (e.g., user is not proximate to the finger pad or user is not in contact with any of the finger pads, all of the finger pads, or a predefined number of finger pads), the processor ceases operation (e.g., teleoperation, movement) of the robotic arm in response to the information from the input device. In some embodiments, the memory stores instructions for execution by the processor, the stored instructions including instructions for, in accordance with the determination of the lack of the user presence, ceasing the operation of the robotic arm in response to the information from the input device.

In some embodiments, in accordance with a determination of a lack of the user presence (e.g., user is not proximate to the finger pad or user is not in contact with any of the finger pads, all of the finger pads, or a predefined number of finger pads), the processor reduces a velocity of the robotic arm in response to the information from the input device. In some embodiments, the memory stores instructions for execution by the processor, the stored instructions including instructions for, in accordance with the determination of the lack of the user presence, reducing the velocity of the robotic arm in response to the information from the input device.

In some embodiments, in accordance with a determination of a lack of the user presence (e.g., user is not proximate to the finger pad or user is not in contact with any of the finger pads, all of the finger pads, or a predefined number of finger pads), the processor reduces motion scaling between the input device and the robotic arm (e.g., reducing an amount of movement of the robotic arm with respect to an amount of movement of the input device). In some embodiments, the memory stores instructions for execution by the processor, the stored instructions including instructions for, in accordance with the determination of the lack of the user presence, reducing the motion scaling between the information from the input device and the movement of the robotic arm.

In some embodiments, the grasper further includes an integrated circuit for measuring a mutual capacitance between the two or more electrodes of the first set of two or more electrodes. The user presence is determined based at least in part on the mutual capacitance.

In some embodiments, the grasper includes a static handle that is coupled to the first finger pad, the first finger pad configured to move relative to the static handle. The integrated circuit is disposed in the static handle.

In some embodiments, the first set of two or more electrodes is embedded within the first finger pad.

In some embodiments, the first set of two or more electrodes includes an electrode layer comprising the two or more electrodes; and a shield layer for reducing capacitance between the two or more electrodes with components of the grasper.

FIG. 40 is a flowchart illustrating a method 410 of operating a medical system for controlling a medical instrument using the input device of FIG. 21.

The method 410 includes (4110) receiving, from a sensor coupled to (e.g., embedded in) a grasper of the input device, sensor information related to a user presence at the grasper; (4120) receiving secondary information associated with the grasper (e.g., a configuration of the grasper, such as grasper angle or velocity, motion of a passively stationary joint, and/or a time point of last grasper movement or last-detected user presence); and (4130) determining user control at the grasper based on the sensor information and the secondary information. As used herein, in some cases, the term "user control" refers to an input intentionally (or deliberately) provided a user for controlling movement of a robotic arm, as compared to an input unintentionally provided by the user (e.g., due a slip of a finger, slow drift, etc.).

In some embodiments, the secondary information includes a time threshold. Determining the user presence at the grasper includes (4132) comparing duration over which the sensor information indicates a lack of the user presence and the time threshold.

In some embodiments, the secondary information includes information indicating a change in a configuration (e.g, position and/or orientation) of the input device at a first time and a second time that is subsequent to the first time (e.g., current time). Determining the user presence at the grasper includes (4134) comparing the change in the configuration of the input device and a configuration change threshold (e.g., a predefined distance and/or angle difference).

In some embodiments, the information indicating the change in the configuration of the input device is obtained by determining a configuration (e.g., a position and/or orientation) of the input device at the first time, determining a configuration of the input device at the second time, and determining the change in the configuration of the input device based on the configuration of the input device at the first time and the configuration of the input device at the second time.

In some embodiments, the secondary information includes information indicating a change in a configuration (e.g., position and/or orientation) of the medical instrument at a first time and a second time that is subsequent to the first time (e.g., current time). Determining the user presence at the grasper includes (4136) comparing the change in the configuration of the medical instrument and a configuration change threshold (e.g., a predefined distance and/or angle difference).

In some embodiments, the information indicating the change in the configuration of the medical instrument is obtained by determining a configuration (e.g., a position and/or orientation) of the medical instrument at the first time, determining a configuration of the medical instrument at the second time, and determining the change in the configuration of the medical instrument based on the configuration of the medical instrument at the first time and the configuration of the medical instrument at the second time.

In some embodiments, the method 410 is performed by a medical system that includes an input device (e.g., the input system 182) for controlling (e.g., movement, function) operation (e.g., teleoperation) of a robotic arm. The input device includes a grasper (e.g., the grasper 200) that includes a first finger pad. The first finger pad includes a first set of two or more electrodes. The medical system also includes an integrated circuit (e.g., the integrated circuit 328) for measuring a mutual capacitance between the two or more electrodes of the first set of two or more electrodes for determining a user presence at the first finger pad (e.g., user proximity to the first finger pad, or user contact with the first finger pad).

FIG. 41 is a flowchart illustrating a method 420 of operating a medical system that includes the input device of FIG. 21.

The method 420 includes (4210) receiving, from a sensor coupled to (e.g., embedded in) a grasper of the input device, sensor information related to a user presence at the grasper; (4220) receiving secondary information from the input device; (e.g., a configuration of the grasper, such as grasper angle or velocity, and/or a time point of last grasper movement or last-detected user presence); (4230) determining whether a user is in control of the input device based on the sensor information and the secondary information (e.g., although a capacitance sensor can detect lack of user presence, this alone is not sufficient to transition into a safe mode-instead, transition to the safe mode may not be triggered until a certain amount of time has passed or a certain drift distance has been detected. This helps reducing disruptions by cutting off teleoperation. If neither of these criteria is met, then the system can enter a "modified teleoperation" mode by, for example, changing motion scaling of the teleoperation, damping the input device, etc.); and (4240) in accordance with a determination that the user is not in control of the input device, transitioning the medical system into a safe mode.

In some embodiments, the robotic arm is coupled to a medical instrument comprising a tool tip. Prior to transitioning the medical system into the safe mode, the medical system operates (4202) in a modified teleoperation mode whereby motion scaling between the input device and the medical instrument is changed such that movement of the tool tip in response to movement of the grasper is reduced. Such modified teleoperation mode allows a user to stay in uninterrupted teleoperation, but reduces likelihood of the user losing control when the user is transiently not in contact with the grasper (or the capacitance sensors).

In some embodiments, prior to transitioning the medical system into the safe mode, the damping of the robotic arm is adjusted (4204) in response to information from the input device.

In some embodiments, prior to transitioning the medical system into the safe mode, haptic feedback is provided (4206) to a user (e.g., via the grasper) to maintain a position of the input device.

In some embodiments, transitioning the medical system into the safe mode includes (4242) halting operation of the robotic arm in response to information from the input device.

In some embodiments, the method 420 also includes transitioning the medical system into an (unmodified) teleoperation mode in accordance with a determination that the user is in control of the input device.

In some embodiments, the method 420 further includes (4250) transitioning the medical system out of the safe mode (e.g., transitioning the medical system into the (unmodified) teleoperation mode or the modified teleoperation mode) based on the sensor information and the secondary information. The second information includes information indicating a duration of time the medical system has been in the safe mode. For example, the medical system may wait for a certain period of time after user presence has been detected (e.g., using a capacitance sensor) before moving a robotic joint in accordance with user input. This reduces or eliminates movement of a robotic joint due to an inadvertent contact.

In some embodiments, the method 420 further includes transitioning the medical system out of the modified teleoperation mode (e.g., transitioning the medical system into the (unmodified) teleoperation mode) based on the sensor information and the secondary information. The second information includes information indicating a duration of time the medical system has been in the safe mode.

In some embodiments, the method 420 further includes, (4260) when the medical system has been in the safe mode for a duration of time less than a predefined threshold, transitioning the medical system out of the safe mode (e.g., transitioning the medical system into the (unmodified) teleoperation mode or the modified teleoperation mode) based on first criteria; and when the medical system has been in the safe mode for a duration of time longer than the predefined threshold, transitioning the medical system out of the safe mode (e.g., transitioning the medical system into the (unmodified) teleoperation mode or the modified teleoperation mode) based on second criteria distinct from the first criteria. For example, the medical system may transition out of the safe mode in response to detecting user presence on one sensor if the medical system has been in the safe mode for a duration of time less than the predefined threshold (e.g., one second), but may require detecting the user presence on two or more sensors if the medical system has been in the safe mode for a duration of time greater than the predefined threshold, before transitioning out of the safe mode.

In some embodiments, the method 420 further includes, when the medical system has been in the modified teleoperation mode for a duration of time less than a predefined threshold, transitioning the medical system out of the modified teleoperation mode (e.g., transitioning the medical system into the (unmodified) teleoperation mode) based on third criteria; and when the medical system has been in the modified teleoperation mode for a duration of time longer than the predefined threshold, transitioning the medical system out of the modified teleoperation mode (e.g., transitioning the medical system into the (unmodified) teleoperation mode) based on fourth criteria distinct from the third criteria.

In some embodiments, the method 420 is performed by a medical system that includes an input device (e.g., the input system 183) for controlling a medical instrument (e.g., surgical tool). The input device includes a grasper (e.g., the grasper 200) for receiving user input; and a sensor (e.g., one or more capacitance sensors) coupled to the grasper for generating sensor information related to a user presence at the grasper. The medical system also includes a processor (e.g., processor(s) 280) and memory (e.g., computer readable storage medium 282) storing instructions for execution by the processor. The stored instructions include instructions for receiving secondary information associated with the grasper (e.g., a configuration of the grasper, such as grasper angle or velocity, and/or a time point of last grasper movement or last-detected user presence) and determining user control at the grasper based on the sensor information and the secondary information.

In some embodiments, the sensor comprises any of a capacitance-based sensor or a light-based sensor.

In some embodiments, the grasper includes a finger pad forming a grasper angle with respect to a reference axis of the grasper, the finger pad being moveable relative to the reference axis. The secondary information includes the grasper angle.

In some embodiments, the input device includes a joint. The secondary information includes a position and/or velocity of the joint.

In some embodiments, the joint comprises a passively stationary joint of the input device.

In some embodiments, the joint comprises a roll joint of the input device.

In some embodiments, the secondary information includes a time threshold for comparison with a duration over which the sensor detects a lack of a user presence.

In some embodiments, the memory also stores instructions for determining the user presence based in part on a comparison of a duration over which the sensor does not detect the user presence and a time threshold.

In some embodiments, the secondary information includes information indicating a change in a configuration (e.g., position and/or orientation) of the input device at a first time and a second time that is subsequent to the first time (e.g., current time).

In some embodiments, the memory also stores instructions for determining the user presence based in part on a comparison of the configuration of the input device at the first time and a configuration of the input device at the second time. In some embodiments, the first time corresponds to a time point when the user presence was detected.

In some embodiments, the secondary information includes information indicating a change in a configuration (e.g., position and/or orientation) of the medical instrument at a first time and a second time that is subsequent to the first time (e.g., current time).

In some embodiments, the memory also stores instructions for determining the user presence based in part on a comparison of the configuration of the medical instrument at the first time and a configuration of the medical instrument at the second time. In some embodiments, the first time corresponds to a time point when the user presence was detected.

3. Implementing Systems and Terminology.

Figure 42:
FIG. 42 is a schematic diagram illustrating electronic components of a medical system that includes the input device of FIG. 21A in accordance with some embodiments.

FIG. 42 is a schematic diagram illustrating electronic components of a medical system that includes the input device of FIG. 21A.

The robotic medical system includes one or more processors 280, which are in communication with a computer readable storage medium 282 (e.g., computer memory devices, such as random-access memory, read-only memory, static random-access memory, and non-volatile memory, and other storage devices, such as a hard drive, an optical disk, a magnetic tape recording, or any combination thereof) storing instructions for performing any methods described herein (e.g., operations described with respect to FIGS. 33, 39A-39B, 40, and 41). The one or more processors 280 are also in communication with an input/output controller 284 (via a system bus or any suitable electrical circuit). The input/output controller 284 receives user input from input device 286 (e.g., the input system 182, or in particular, the grasper 200) and sensor data from one or more sensors (e.g, sensors 287, such as capacitance sensors, optical sensors, grasper angle sensor, etc. as described herein, which are coupled to the input device 286), and relays the sensor data to the one or more processors 280. In some embodiments, the sensors 287 include the integrated circuit 328. In some embodiments, the integrated circuit 328 is integrated with the one or more processors 280 (or vice versa). The input/output controller 284 also receives instructions and/or data from the one or more processors 280 and relays the instructions and/or data to one or more actuators, such as first motors 292-1 and 292-2, etc. In some embodiments, the input/output controller 284 is coupled to one or more actuator controllers 290 and provides instructions and/or data to at least a subset of the one or more actuator controllers 290, which, in turn, provide control signals to selected actuators 292. In some embodiments, the one or more actuator controller 290 are integrated with the input/output controller 284 and the input/output controller 284 provides control signals directly to the one or more actuators 292 (without a separate actuator controller). Although FIG. 39 shows that there is one actuator controller 290 (e.g., one actuator controller for the entire medical platform, in some embodiments, additional actuator controllers may be used (e.g., one actuator controller for each actuator, etc.).

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical system comprising:
an input device for controlling a medical instrument, wherein the input device comprises:
a gimbal;
a grasper for receiving user input, the grasper coupled to the gimbal; and
an optical sensor coupled to the grasper for generating sensor information related to a user presence at the grasper, the optical sensor facing toward the gimbal;
a processor; and
memory storing instructions for execution by the processor, the stored instructions including instructions for:
receiving secondary information associated with the grasper; and
determining user control at the grasper based on the sensor information and the secondary information.

2. The medical system of claim 1, wherein:
the grasper includes a finger pad forming a grasper angle with respect to a reference axis of the grasper, the finger pad being moveable relative to the reference axis; and
the secondary information includes the grasper angle.

3. The medical system of claim 1, wherein:
the input device includes a joint; and
the secondary information includes at least one of a position or a velocity of the joint.

4. The medical system of claim 3, wherein the joint comprises at least one of:
a passively stationary joint of the input device; or a roll joint of the input device.

5. The medical system of claim 1, wherein:
the secondary information includes a time threshold for comparison with a duration over which the sensor detects a lack of a user presence.

6. The medical system of claim 1, wherein:
the secondary information includes at least one of:
information indicating a change in a configuration of the input device at a first time and a second time that is subsequent to the first time; or
information indicating a change in a configuration of the medical instrument at a first time and a second time that is subsequent to the first time.

7. The medical system of claim 1, wherein:
the input device is configured to control the medical instrument via a robotic arm; and
the stored instructions include instructions for:
receiving the secondary information from the input device;
determining whether a user is in control of the input device based on the sensor information and the secondary information; and
in accordance with a determination that the user is not in control of the input device, transitioning the medical system into a safe mode.

8. The medical system of claim 7, wherein the safe mode comprises halting operation of the robotic arm in response to information from the input device.

9. The medical system of claim 7, wherein:
the robotic arm is coupled to the medical instrument, the medical instrument comprising a tool tip; and
the stored instructions include instructions for, prior to transitioning the medical system into the safe mode, changing motion scaling between the input device and the medical instrument such that movement of the tool tip in response to movement of the grasper is reduced.

10. The medical system of claim 7, wherein, prior to transitioning the medical system into the safe mode, damping of the robotic arm is adjusted in response to information from the input device.

11. The medical system of claim 7, wherein the safe mode comprises providing haptic feedback to a user to maintain a position of the input device.

12. The medical system of claim 1, wherein:
the grasper comprises a first end coupled to the gimbal and a second end opposite the first end; and
the optical sensor is mounted to the second end of the grasper facing toward the first end.

13. The medical system of claim 12, wherein:
the grasper comprises a central support and a pair of opposing finger pads coupled to the central support;
the central support is coupled to the gimbal at the first end; and
the pair of opposing finger pads are coupled to the central support at the second end.

14. The medical system of claim 1, wherein the grasper comprises a pair of opposing finger pads and a pair of finger loops coupled to the pair of opposing finger pads.

15. The medical system of claim 14, wherein the processor is configured to distinguish, in the sensor information, the finger loops from a user's body parts.

16. The medical system of claim 1, wherein:
the grasper comprises a first finger pad, a second finger pad opposing the first finger pad, and a second sensor;
the optical sensor includes a first light source configured to provide a first light curtain directed towards the first finger pad; and
the second sensor includes a second light source configured to provide a second light curtain directed towards the second finger pad.

17. The medical system of claim 16, wherein:

the grasper comprises a third finger pad and a third sensor; and the third sensor includes a third light source configured to provide a third light curtain directed towards the third finger pad.

18. The medical system of claim 1, wherein:

the input device further comprises a positioning platform coupled to the gimbal such that the positioning platform and the gimbal permit six degrees of freedom of movement of the grasper in accordance with a determination that a user is in control of the input device; and the processor is configured to provide haptic feedback to the input device that restricts the six degrees of freedom of movement in accordance with a determination that the user is not in control of the input device.

\* \* \* \* \*